US005722411A

United States Patent [19]

Suzuki et al.

[11] Patent Number: 5,722,411
[45] Date of Patent: Mar. 3, 1998

[54] ULTRASOUND MEDICAL TREATMENT APPARATUS WITH REDUCTION OF NOISE DUE TO TREATMENT ULTRASOUND IRRADIATION AT ULTRASOUND IMAGING DEVICE

[75] Inventors: Takuji Suzuki, Kanagawa-ken; Satoshi Aida, Tokyo; Katsuhiko Fujimoto; Mariko Shibata, both of Kanagawa-ken; Yoshiharu Ishibashi, Tokyo; Mamoru Izumi, Tokyo; Shiroh Saitoh, Tokyo; Kazuya Okamoto, Saitama-ken, all of Japan

[73] Assignee: Kabushiki Kaisha Toshiba, Kawasaki, Japan

[21] Appl. No.: 681,451

[22] Filed: Jul. 23, 1996

Related U.S. Application Data

[63] Continuation of Ser. No. 209,528, Mar. 14, 1994, Pat. No. 5,553,618.

[30] Foreign Application Priority Data

| Mar. 12, 1993 | [JP] | Japan | 5-052683 |
| Aug. 5, 1993 | [JP] | Japan | 5-194359 |
| Aug. 5, 1993 | [JP] | Japan | 5-194360 |
| Sep. 14, 1993 | [JP] | Japan | 5-228744 |

[51] Int. Cl.$^6$ .................................... A61B 8/00
[52] U.S. Cl. .................. 128/660.03; 601/3; 128/660.07
[58] Field of Search .................. 128/660.01, 660.03, 128/660.07, 901; 601/2–4; 607/97

[56] References Cited

U.S. PATENT DOCUMENTS

| 3,237,623 | 3/1966 | Gordon | 601/3 |
| 4,554,925 | 11/1985 | Young | 128/653 |
| 4,658,828 | 4/1987 | Dory | 128/660 |
| 4,803,995 | 2/1989 | Ishida et al. | 128/660.01 |
| 4,914,608 | 4/1990 | LeBihan et al. | 364/557 |
| 5,247,935 | 9/1993 | Cline et al. | 128/653.2 |
| 5,291,890 | 3/1994 | Cline et al. | 128/653.2 |
| 5,358,466 | 10/1994 | Aida et al. | 601/4 |

FOREIGN PATENT DOCUMENTS

| 0 170 416 A1 | 2/1986 | European Pat. Off. |
| 62-49843 | 3/1987 | Japan |
| 63-5736 | 1/1988 | Japan |
| 5-42147 | 2/1993 | Japan |
| 5-300910 | 11/1993 | Japan |
| 6-78930 | 3/1994 | Japan |

OTHER PUBLICATIONS

Vallancien et al., "Focussed Extracorporeal Pyrotherapy: Experimental Results", *Eur. Urol.*, vol. 20:211–219, (1991).

Zerhouni et al., "Human Heart: Tagging With MR Imaging—A Method For Noninvasive Assessment of Myocardial Motion", *Radiology*, vol. 169:59–63, (1988).

Hardy et al., "Spatial Localization in Two Dimensions Using NMR Designer Pulses", *Journal of Magnetic Resonance*, vol. 82:647–654, (1989).

Hynynen, "The Threshold For Thermally Significant Cavitation in Dog's Thigh Muscle in vivo", *Ultrasound in Med. & Biol.*, vol. 17:157–169, (1991).

*Primary Examiner*—Ruth S. Smith
*Attorney, Agent, or Firm*—Foley & Lardner

[57] ABSTRACT

An ultrasound medical treatment apparatus includes an ultrasound applicator for applying ultrasound irradiation to a treatment target. The treatment apparatus also includes an ultrasound imaging device that transmits ultrasound pulses to image the treatment target. The treatment apparatus is capable of reducing noises occurring at an ultrasound imaging device due to the ultrasound irradiation generated by the ultrasound application during ultrasound medical treatment. The noises may be reduced by increasing a transmission power of the ultrasound pulses. Alternatively, the noises may be reduced by subtracting pre-recorded noise components from the ultrasound pulses received by the ultrasound imaging device, where the pre-recorded noise components are characteristic of noise occurring at the ultrasound imaging device due to the ultrasound irradiation generated by the ultrasound applicator.

1 Claim, 40 Drawing Sheets

FIG.43
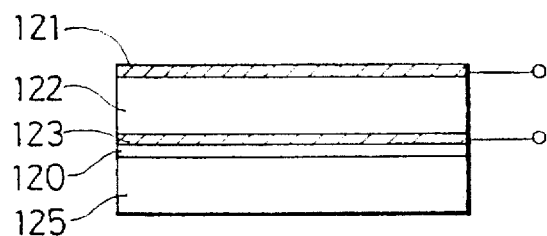
FIG.44
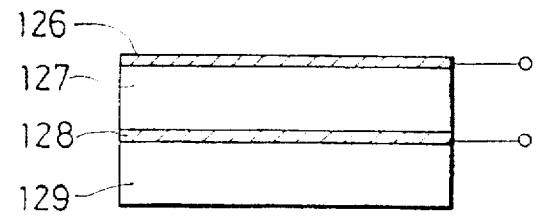
FIG.45
FIG.46
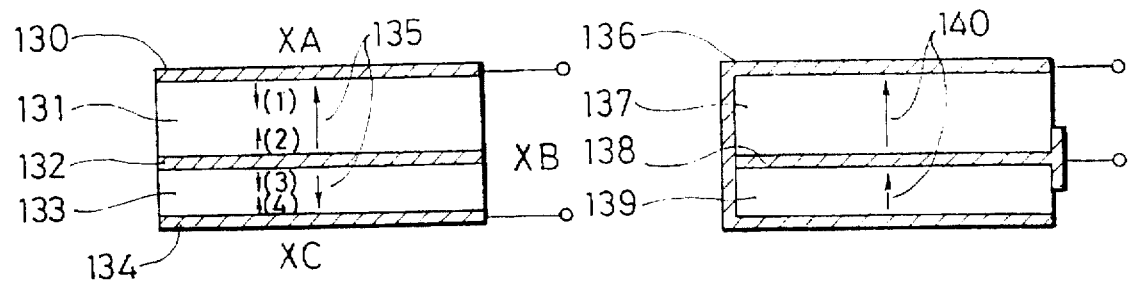
FIG.47
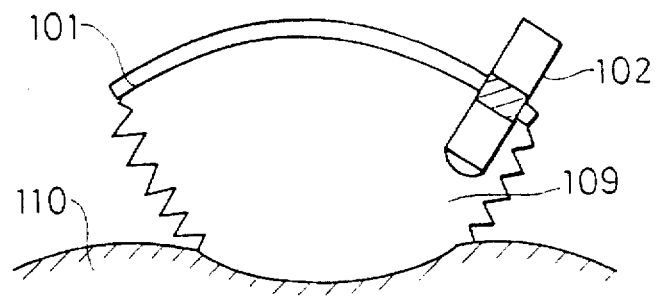

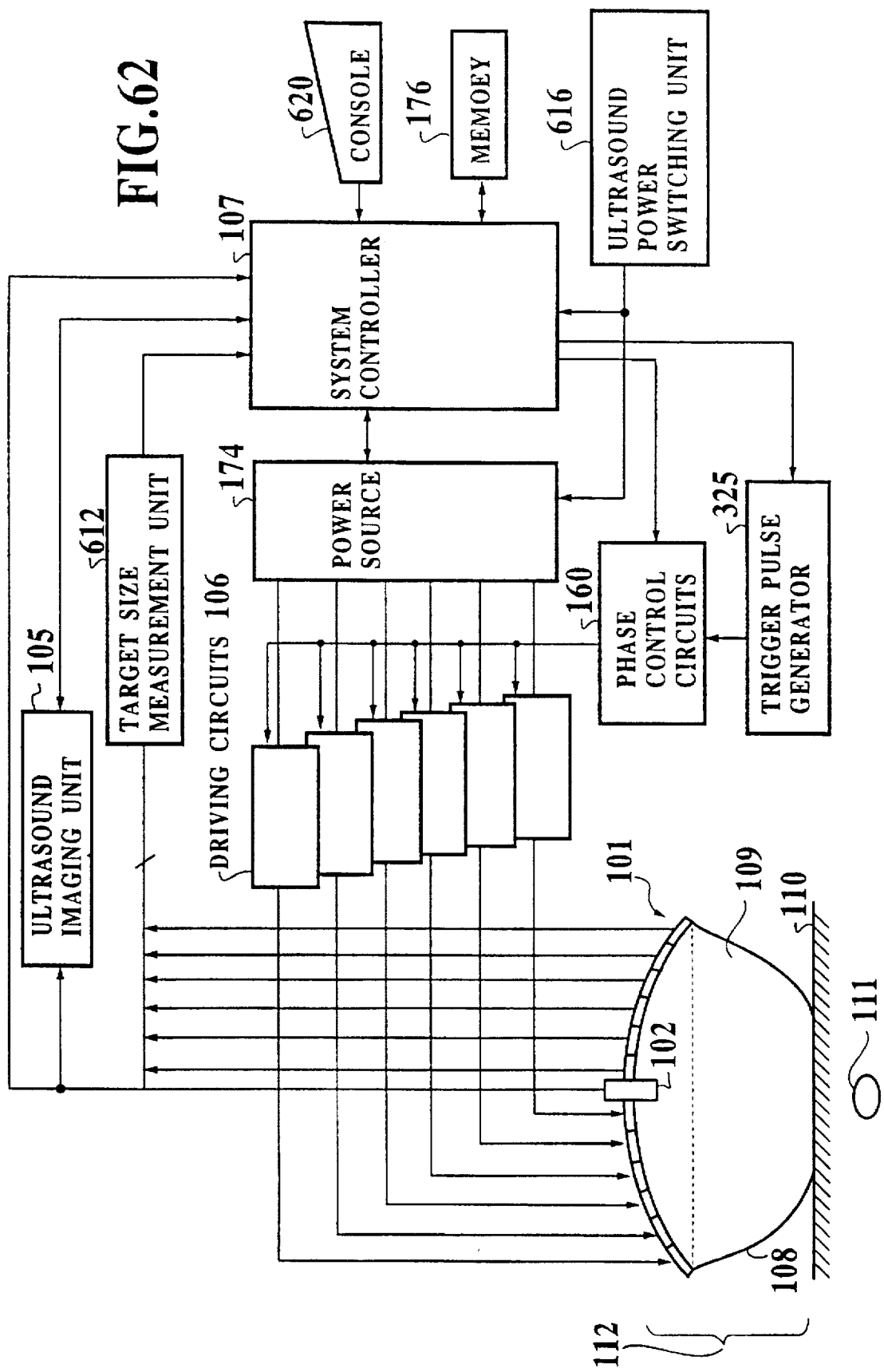

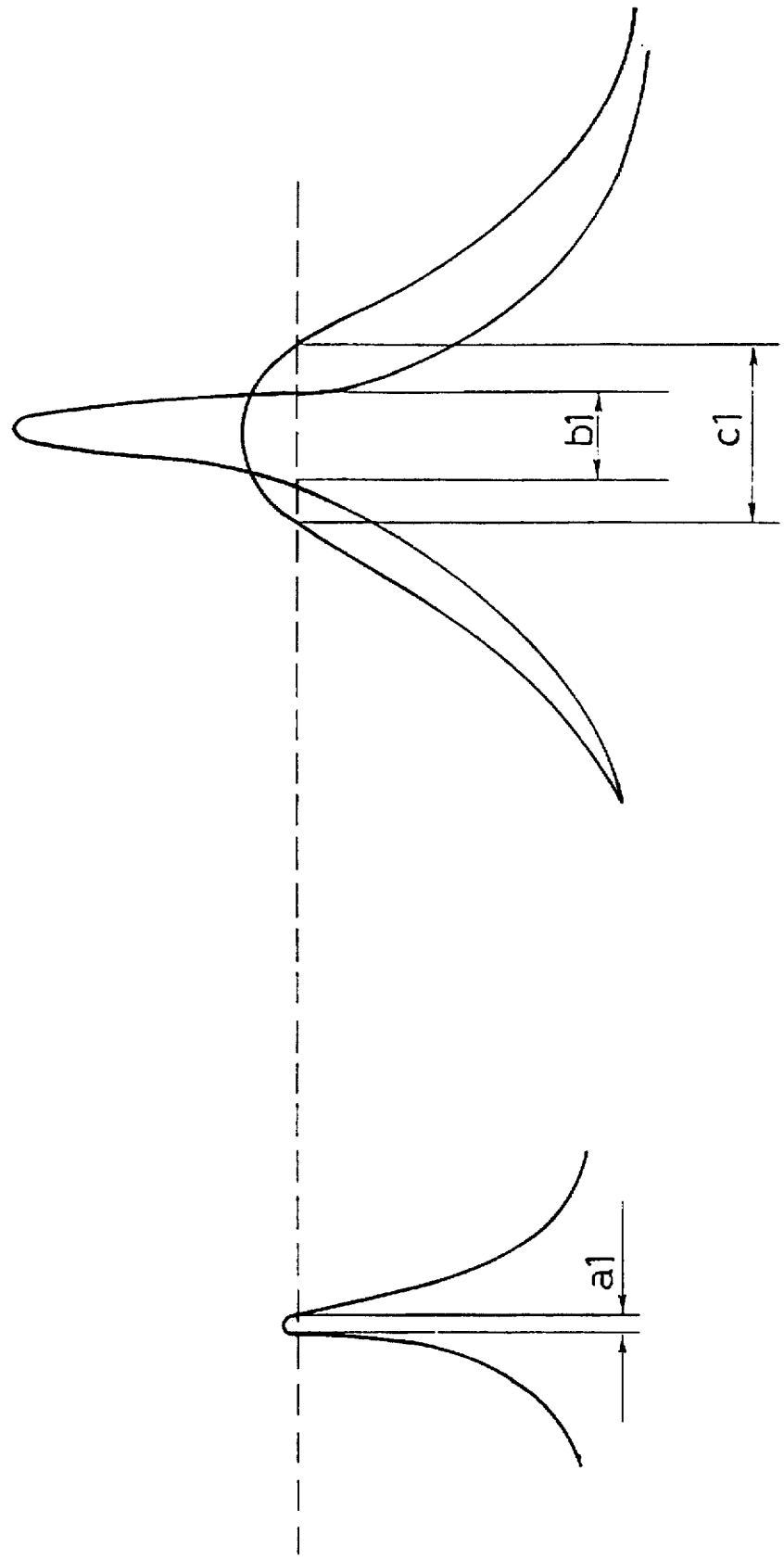

ULTRASOUND MEDICAL TREATMENT APPARATUS WITH REDUCTION OF NOISE DUE TO TREATMENT ULTRASOUND IRRADIATION AT ULTRASOUND IMAGING DEVICE

This application is a continuation of application Ser. No. 08/209,528, filed Mar. 14, 1994 now U.S. Pat. No. 5,553,618.

BACKGROUND OF THE INVENTION

1. Field of the Invention

The present invention relates to an ultrasound medical treatment apparatus for treating a treatment target by irradiating intense focused ultrasound from outside of a patient, and an ultrasonic medical treatment apparatus utilizing an imaging device.

2. Description of the Background Art

The conventional non-invasive temperature measurement for an interior of the patient using temperature dependent magnetic resonance (MR) parameters used in ultrasound medical treatment requires complete data of both the positional relationship of the patient's organs and the temperature coefficients for the organs. Moreover, when precision of the temperature needs to be improved in order to improve the signal/noise ratio, spatial resolution must be sacrificed. Thus, non-invasive temperature measurement has been inappropriate for hyperthermia which requires high spatial and temperature resolutions.

Also, when a temperature change occurs in the measurement target, the measured MR parameters change because of their own temperature dependency. A change of the MR image due to degeneration thus can be obscured, and accurate judgement of the treatment's effect cannot be made. The treatment may be ended prematurely or applied excessively. Moreover, the efficiency of the treatment is lowered, and normal tissues can be affected.

Further, where significant motion occurs such as respiratory motion or heart beat motion, a danger arises because the focal point of the radiation applied to a treatment target during ultrasound medical treatment is displaced, and the normal tissues can be damaged. Moreover, in a case of treating a relatively large treatment target, such as cancerous tissue, by a scanning technique having a very small focal point, the scanning plan (treatment plan) can be spoiled, and the radiation position may be overlooked.

Furthermore, when an ultrasound imaging device is incorporated, real time continuous monitoring of treatment becomes possible. But, the ultrasound imaging device can only provide a two-dimensional tomographic image, so that anything off the tomographic plane cannot be handled. Moreover, the ultrasound imaging device has low resolution so that high precision setting of the focal point is difficult, and it has been very difficult to trace a narrow region accurately.

Now, in an ultrasound medical treatment apparatus, it is important to irradiate only the treatment target with intense ultrasound and not to affect the normal tissues. However, when tissues having different acoustic impedances are present on the ultrasound's irradiation route, refraction and reflection can occur, which displaces the focal point. Also, when an object with considerably different acoustic impedance, such as bone, lung, and clearance (intestinal gas), is present, further propagation of ultrasound to the treatment target can be prevented. Heat generation due to energy absorption occurs at such a position and may cause unexpected tissue degeneration.

Also, a tumor contains more blood vessels than normal tissues, and when irradiation with intense energy occurs, blood vessels can be damaged, and severe loss of blood can be caused.

Moreover, conventional techniques have not taken into account the change of the acoustic characteristic of thermally degenerated tissues.

In addition, during treatment with intense ultrasound radiation, cases have occurred in which the patient abruptly moves by sensing intense pain or heat, or for some other reason. In such a case, the focal point of the intense ultrasound is displaced from the intended position so that there is a danger of damaging normal tissues.

In ultrasound medical treatment, there is a need to monitor the treatment region and the ultrasound transducer. Ultrasound imaging is suitable for this purpose as it can provide real time monitoring. However, ultrasound imaging can be affected by noise due to the ultrasound irradiation used in ultrasound medical treatment so that monitoring during the treatment cannot be made. Even when intermittent ultrasound irradiation is adopted to cope with this problem, the real time feature cannot be realized, and accurate ultrasound irradiation has been difficult due to body movement and respiratory motion.

SUMMARY OF THE INVENTION

It is therefore an object of the present invention to provide a method and an apparatus for ultrasound medical treatment capable of determining a hot spot at high spatial resolution, and preventing the displacement of the hot spot from the focal point.

It is another object of the present invention to provide a method and an apparatus for ultrasound medical treatment capable of separating the change due to temperature from the the change due to degeneration, so that the change due to the degeneration can be obtained accurately.

It is another object of the present invention to provide a method and an apparatus for ultrasound medical treatment capable of tracing the moving treatment portion.

It is another object of the present invention to provide an ultrasound medical treatment apparatus capable of reducing noise due to the ultrasound irradiation used in ultrasound medical treatment, such that a high image quality can be obtained in real time even during the treatment.

It is another object of the present invention to provide a method and an apparatus for ultrasound medical treatment capable of carrying out the treatment safely and efficiently.

According to one aspect of the present invention there is provided a medical treatment apparatus, comprising: an imaging device for obtaining image data of a treatment portion containing a treatment target; irradiation means for applying radiation onto the treatment target; and control means for controlling the imaging device and the irradiation means, the control means controlling the imaging device is to obtain hot spot detection image data after the control means controls the energy irradiation means to apply radiation at a prescribed level, the control means detecting a hot spot indicating a change due to a temperature change caused by the radiation at the prescribed level from the hot spot detection image data, and the control means controlling the irradiation means to apply treatment radiation at a treatment level higher than the prescribed level according to the detected hot spot.

According to another aspect of the present invention there is provided a method of medical treatment, comprising the steps of: applying radiation at a prescribed level onto a treatment target by an irradiation means; obtaining hot spot detection image data of a treatment portion containing the treatment target by an imaging device after the irradiation means applies radiation at the prescribed level; detecting a hot spot indicating a change due to a temperature change caused by the radiation at the prescribed level from the hot spot detection image data; and carrying out a treatment by applying treatment radiation at a treatment level higher than the prescribed level by the irradiation means according to the detected hot spot.

According to another aspect of the present invention there is provided an ultrasound medical treatment apparatus, comprising: ultrasound applicator means for applying ultrasound irradiation to a treatment target; ultrasound imaging device for imaging the treatment target by transmitting ultrasound pulses and receiving the ultrasound pulses reflected by the treatment target, having noise reduction means for reducing noises due to the ultrasound irradiation by the ultrasound applicator means.

According to another aspect of the present invention there is provided an ultrasound medical treatment apparatus, comprising: ultrasound applicator for applying ultrasound irradiation to a treatment target, having first piezoelectric means for generating the ultrasound irradiation at first fundamental frequency; and ultrasound imaging device for imaging the treatment target by transmitting ultrasound pulses and receiving the ultrasound pulses reflected by the treatment target having second piezoelectric means for generating the ultrasound pulses at second fundamental frequency; wherein at least one of the first and second piezoelectric means also generates secondary harmonic at frequency different from the first and second fundamental frequencies.

According to another aspect of the present invention there is provided an ultrasound medical treatment apparatus, comprising: imaging means for obtaining sequential image data of a treatment portion containing a treatment target; simulation means for producing dummy model of the treatment portion according to the image data obtained by the imaging means; condition setting means for setting ultrasound irradiation conditions according to the dummy model produced by the simulation means; and ultrasound irradiation means for applying an ultrasound irradiation onto the treatment target according to the ultrasound irradiation conditions set by the condition setting means.

According to another aspect of the present invention there is provided a method of ultrasound medical treatment, comprising the steps of: obtaining sequential image data of a treatment portion containing a treatment target; simulating the treatment target portion by producing dummy model of the treatment portion according to the image data obtained at the obtaining step; setting ultrasound irradiation conditions according to the dummy model at the simulating step; and applying an ultrasound irradiation onto the treatment target according to the ultrasound irradiation conditions set at the setting step.

According to another aspect of the present invention there is provided an ultrasound medical treatment apparatus, comprising: imaging means for obtaining image data of a treatment portion containing a treatment target; ultrasound irradiation means for applying an ultrasound irradiation onto the treatment target; and control means for dividing the treatment target into a plurality of sections according to the image data, determining an order of treatment for divided sections according to a relative position of each section with respect to the ultrasound irradiation means, and controlling the ultrasound irradiation means to carry out the treatment according to the determined order of treatment.

According to another aspect of the present invention there is provided a method of ultrasound medical treatment, comprising the steps of: obtaining image data of a treatment portion containing a treatment target; dividing the treatment target into a plurality of sections according to the image data obtained at the obtaining step; determining an order of treatment for sections divided at the dividing step, according to a relative position of each section with respect to ultrasound irradiation means; and carrying out the treatment by applying an ultrasound irradiation onto the treatment target from the ultrasound irradiation means, according to the determined order of treatment.

According to another aspect of the present invention there is provided an ultrasound medical treatment apparatus, comprising: ultrasound irradiation means for applying an ultrasound irradiation focused to a focal point set on a treatment target; and imaging means for obtaining image data of a treatment portion containing the treatment target and a tag after the ultrasound irradiation by the ultrasound irradiation means, where the tag is produced by a pulse sequence for tagging a predetermined treatment position located on the focal point at a time of the ultrasound irradiation by the ultrasound irradiation means; and control means for controlling the ultrasound irradiation means to shift the focal point according to a displacement of the tag with respect to the focal point in the image data obtained by the imaging means, before a next ultrasound irradiation by the ultrasound irradiation means.

According to another aspect of the present invention there is provided a method of ultrasound medical treatment, comprising the steps of: applying an ultrasound irradiation focused to a focal point set on a treatment target; obtaining image data of a treatment portion containing the treatment target and a tag, after the ultrasound irradiation by ultrasound irradiation means at the applying step, where the tag is produced by a pulse sequence for tagging a predetermined treatment position located on the focal point at a time of the ultrasound irradiation by the ultrasound irradiation means; and controlling the ultrasound irradiation means to shift the focal point according to a displacement of the tag with respect to the focal point in the image data obtained in real time at the obtaining step, before a next ultrasound irradiation by the ultrasound irradiation means.

According to another aspect of the present invention there is provided an ultrasound medical treatment apparatus, comprising: ultrasound irradiation means for applying an ultrasound irradiation focused to a focal point set on a treatment target; and temperature distribution measurement means for measuring temperature distribution of a treatment portion containing the treatment target to obtain temperature increase point data; and control means for controlling the temperature distribution measurement means and the ultrasound irradiation means, such that the temperature distribution measurement means to obtain the temperature increase point data after the ultrasound irradiation means is controlled to apply an ultrasound irradiation at a prescribed level, and the control means detects a temperature increase point from the temperature increase point data and controls the ultrasound irradiation means to apply a treatment energy irradiation at a treatment level higher than the prescribed level after shifting the focal point according to a displacement of the temperature increase point with respect to the focal point in the temperature distribution data obtained by the temperature distribution measurement means.

According to another aspect of the present invention there is provided a method of ultrasound medical treatment, comprising the steps of: applying an ultrasound irradiation at a prescribed level to a treatment target by an ultrasound irradiation means; measuring temperature distribution of a treatment portion containing the treatment target, to obtain temperature increase point data after the ultrasound irradiation means applies the ultrasound irradiation at the prescribed level; detecting a temperature increase point from the temperature increase point data obtained at the measuring step; and controlling the ultrasound irradiation means to apply a treatment ultrasound irradiation at a treatment level higher than the prescribed level after shifting the focal point according to a displacement of the temperature increase point detected at the detecting step with respect to the focal point in the temperature increase point data obtained at the measuring step.

According to another aspect of the present invention there is provided an ultrasound medical treatment apparatus, comprising: ultrasound irradiation means for applying an ultrasound irradiation focused to a treatment target, to raise a temperature of the treatment target; temperature measurement means for measuring the temperature of the treatment target after the ultrasound irradiation is applied by the ultrasound irradiation means; and imaging device for obtaining image of a treatment portion containing the treatment target only when the temperature of the treatment target measured by the temperature measurement means indicates a normal temperature of the treatment target.

According to another aspect of the present invention there is provided a method of ultrasound medical treatment, comprising: applying an ultrasound irradiation to a treatment target, to raise a temperature of the treatment target; measuring the temperature of the treatment target after the ultrasound irradiation is applied by the ultrasound irradiation means; and obtaining image of a treatment portion containing the treatment target only when the temperature of the treatment target measured by the measuring step indicates a normal temperature of the treatment target.

According to another aspect of the present invention there is provided an ultrasound medical treatment apparatus, comprising: ultrasound irradiation means for applying an ultrasound irradiation to a treatment target, to increase a temperature of the treatment target and cause a degeneration at the treatment target; imaging device for obtaining image of a treatment portion containing the treatment target; and processing means for separating a change of the image due to the degeneration from a change of the image due to a temperature increase by subtracting a predicted change due to the temperature increase alone from the image obtained by the imaging device.

According to another aspect of the present invention there is provided a method of ultrasound medical treatment, comprising the steps of: applying an ultrasound irradiation to a treatment target, to increase a temperature of the treatment target and cause a degeneration at the treatment target; obtaining image of a treatment portion containing the treatment target; and separating a change of the image due to the degeneration from a change of the image due to a temperature increase by subtracting a predicted change due to the temperature increase alone from the image obtained at the obtaining step.

According to another aspect of the present invention there is provided an ultrasound medical treatment apparatus, comprising: ultrasound irradiation means for applying an ultrasound irradiation to a treatment target in a patient; sensor means for detecting a reflective motion of the patient; and controlling means for controlling operation of the ultrasound irradiation means in accordance with a detection of the reflective motion by the sensor means.

Other features and advantages of the present invention will become apparent from the following description taken in conjunction with the accompanying drawings.

BRIEF DESCRIPTION OF THE DRAWINGS

FIGS. 43, 44, 45, and 46 are side views showing four possible configurations for each piezoelectric element used in the apparatus of FIG. 42.

FIG. 47 is a partial diagram showing a possible modification in the apparatus of FIG. 42.

FIG. 62 is a schematic block diagram of a fifteenth embodiment of an ultrasound medical treatment apparatus according to the present invention.

FIGS. 63A and 63B are illustrations of focal point pressure profiles for three cases in the apparatus of FIG. 62.

DETAILED DESCRIPTION OF THE PREFERRED EMBODIMENTS

Figure 1:
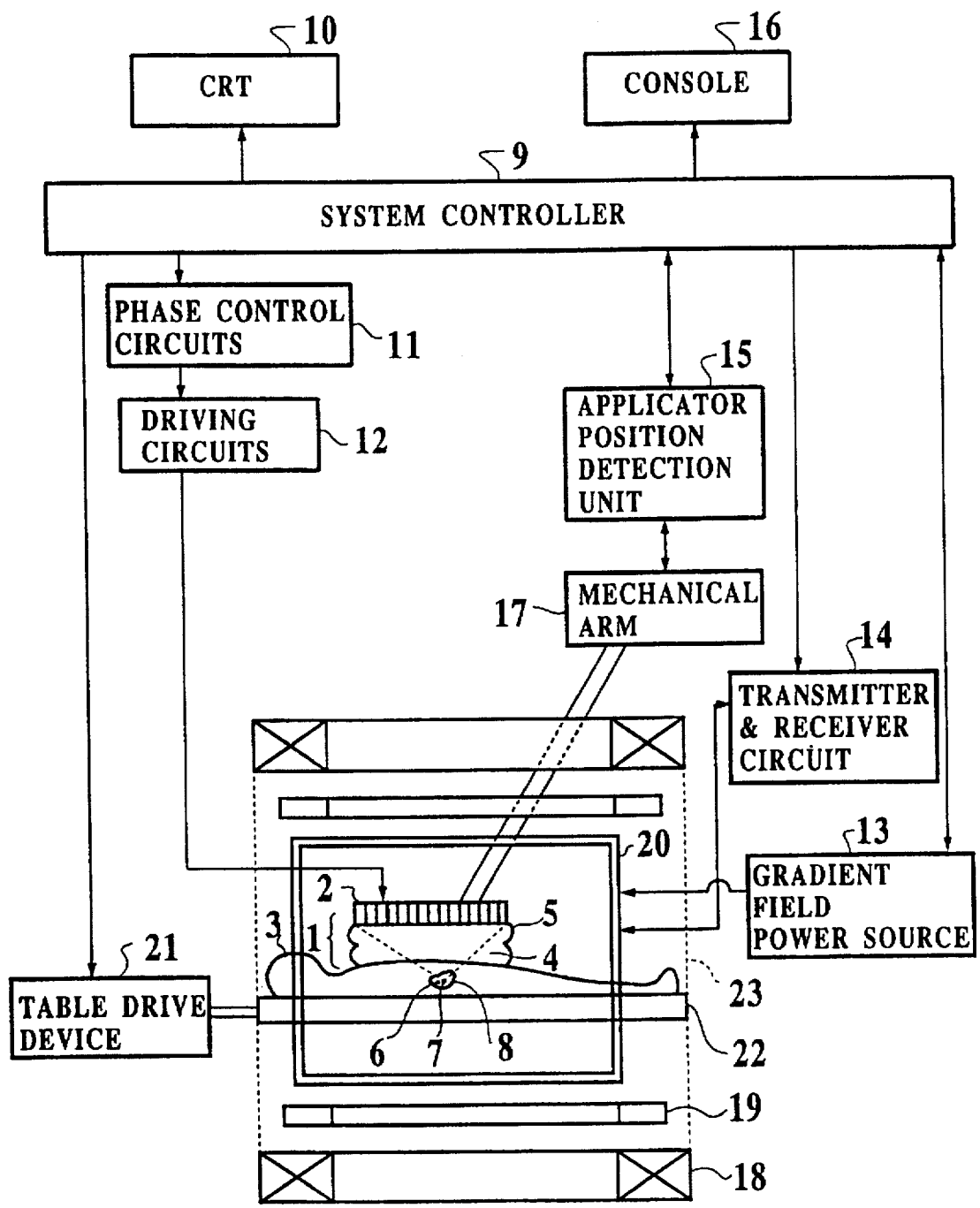
FIG. 1 is a schematic block diagram of a first embodiment of an ultrasound medical treatment apparatus according to the present invention.

Referring now to FIG. 1, the first embodiment of an ultrasound medical treatment apparatus according to the present invention will be described in detail.

The ultrasound medical treatment apparatus of this first embodiment is of a type which incorporates a nuclear magnetic resonance imaging (MRI) apparatus and has a configuration as shown in FIG. 1.

First, an ultrasound treatment portion of the invention as shown in FIG. 1 will be described.

Namely, the ultrasound treatment portion includes an ultrasound applicator 1 which comprises an ultrasound transducer 2 for treating a patient by irradiating intense ultrasound, and a water bag 5 containing a coupling fluid 4 for leading the intense ultrasound from the ultrasound transducer 2 to a patient 3.

Figure 2:
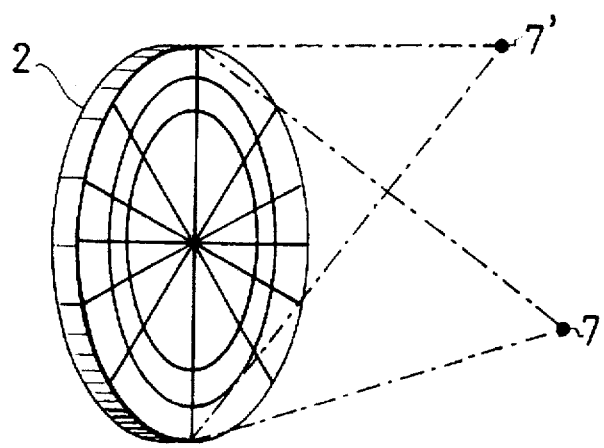
FIG. 2 is a perspective view of a phased array type ultrasound transducer used in the apparatus of FIG. 1.

Here, the ultrasound transducer 2 has a circular disk shaped phased array structure which is divided in radial and circumferential directions as shown in FIG. 2. This ultrasound transducer is connected with driving circuits 12 which drive the ultrasound transducer 2 to irradiate the intense ultrasound during treatment in order to treat the treatment target located at a focal point 7 by heating the treatment target such as a tumor 8 at a high temperature.

In this first embodiment, as the phased array type ultrasound transducer 2 is employed, it is possible to control the driving timings of the driving circuits 12 by phase control circuits 11, such that the focal point position, the acoustic field, and the heated region can be controlled without moving the applicator 1. Here, the driving circuits 12 are divided into a number of channels corresponding to the divided sections of the ultrasound transducer 2, and each channel can be driven independently by independent timing signals obtained at the phase control circuits 11 by applying delays to the control signals from a system controller 9.

In this manner, the focal point of the ultrasound generated by the ultrasound transducer 2 can be set at any desired 3D position, as indicated by points 7 and 7' shown in FIG. 2 for example.

The ultrasound applicator 1 is movably supported by a mechanical arm 17 which is controlled by the system controller 9 through an applicator position detection unit 15. The system controller 9 has functions of a controller for the ultrasound treatment part as well as a sequence controller and a data processing unit for an MRI part to be described below.

Next, the patient positioning part and the MRI part in the configuration of FIG. 1 will be described.

The patient 3 is placed on a treatment table 22, and carried into an MRI gantry 23 in which a magnet 18, gradient coils 19, and an RF coil 20 for MR imaging are provided, by a table drive device 21 controlled by the system controller 9.

Here, in order to prevent the disturbance of the magnetic fields used in the MRI due to the ultrasound applicator 1, there is a need to form the ultrasound applicator 1 by non-magnetic materials as much as possible. For example, the ultrasound applicator 1 and the mechanical arm 17 can be made of materials such as reinforced plastic and austenitic cast iron which has nearly the same mechanical property as the usual east iron while being non-magnetic. It is also possible to make the mechanical arm 17 to be a hydraulic type, rather than an electrical type using an electric motor, to further reduce the amount of magnetic material.

Next, the system controller 9 activates a gradient field power source 13 and a transmitter and receiver circuit 14 according to a prescribed pulse sequence such as that of the T2 weighted imaging scheme which is commanded from a console 16, so as to obtain the 3D MR image data for an interior of the patient 3, which are subsequently stored in a memory (not shown).

Here, according to the MR images of the interior of the patient 3 obtained by the MRI part, it is possible to set up an appropriate treatment plan in advance.

When the MR images are obtained, the system controller 9 controls the mechanical arm 17 to attach the ultrasound applicator 1 on the patient 3. Here, the position of the focal point 7 of the ultrasound to be irradiated from the ultrasound applicator 1 can be calculated and memorized by the system controller 9 according to an applicator position detected by the applicator position detection unit 15 containing potentiometers (not shown) attached on various parts of the mechanical arm 17, and the data on an attachment position of the mechanical arm 17 with respect to the MRI part measured in advance, such that the position of the focal point 7 can be indicated on the MR images displayed by a CRT 10 as shown in FIG. 3A.

Figure 3A:
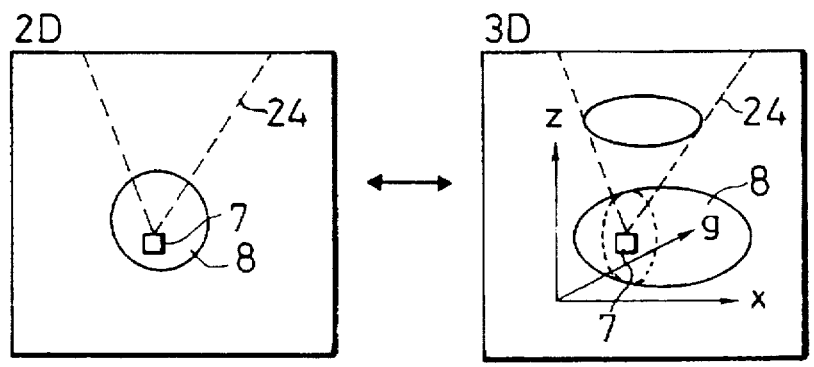
FIGS. 3A and 3B are 2D and 3D images obtained in the apparatus of FIG. 1 before and after the ultrasound irradiation, respectively.
Figure 3B:
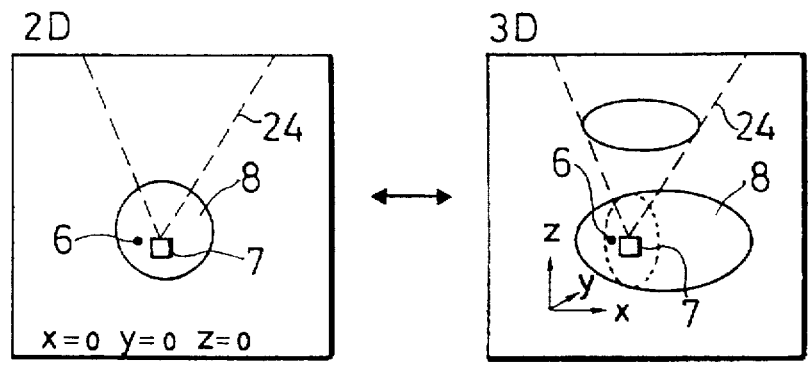

Also, in addition to the focal point 7, the ultrasound incident route 24 can also be indicated on the MR images displayed by the CRT 10 as shown in FIG. 3A. Moreover, as shown in FIGS. 3A and 3B, the x, y coordinates in a case of 2D display or the x, y, z coordinates in a case of 3D display can also be indicated on the MR images displayed by the CRT 10 so as to indicate the positional relationship of the focal point 7 and the tumor 8.

Now, in this ultrasound medical treatment apparatus of FIG. 1, a measurement of a hot spot caused by the irradiation of the ultrasound can be utilized in the treatment procedure as follows.

Namely, the hot spot measurement can be utilized in confirming the coincidence of the treatment target and the treatment position by generating the hot spot before the actual treatment and measuring the position of the hot spot. Here, however, the generated hot spot may be located on a normal tissue, so that the ultrasound irradiation condition such as the ultrasound power to be used in generating the hot spot should be carefully controlled so as not to cause any damage to the tissues.

In this regard, in the field of the hyperthermia, the relationship of the heating temperature and time with respect to the treatment effect (survival rate) for a cell has been established as expressed by the following equation (1):

$$\ln S = -A \int_0^\infty \exp[-Ea/R[T_0 + \Delta T(t)]] dt \tag{1}$$

where $T_0$ is the temperature before the energy irradiation, $\Delta T(t)$ is a time profile of the temperature change, Ea is an empirical activation energy, A is a proportional constant, R is a gas constant, and S is the survival rate for a cell after the heating.

Here, the empirical activation energy Ea can be related to the enthalpy $\Delta H$ of the degeneration according to the following equation (2):

$$Ea = \Delta H + R \times T \tag{2}$$

so that this empirical activation energy Ea can be obtained from the enthalpy of the degeneration reaction characteristic to the target cell.

Alternatively, the activation energy Ea and the proportional constant A for the target cell can be measured by conducting the experiment using the target cell, as these quantities can be different for different types of the cell. From the past experiments, it is believed that the ranges for these quantities are approximately 50 Kcal/mol<Ea<200 Kcal/mol and $10^{90} < A < 10^{780}$.

Thus, by setting the final survival rate S according to the above equation (1) at a sufficiently high level, and controlling the ultrasound irradiation to guarantee this setting level, the damage to the normal tissues due to the generation of the hot spot can be prevented effectively. For example, the setting of over 0.7 for the survival rate S should be sufficient in practice.

Now, the procedure for the generation and the measurement of the hot spot as well as its use in the treatment according to this first embodiment will be described in detail. In this first embodiment, the measurement of a temperature change based on the T1 weighted images is employed.

Before the treatment, the imaging for the positioning purpose is carried out, and the patient is positioned according to a displacement detected by comparing the image obtained by this imaging and the image obtained at a time of the treatment plan set up.

After this positioning, the T1 weighted image is acquired as a reference image for the hot spot measurement to be carried out prior to the intense ultrasound irradiation. The obtained reference image is stored in a memory (not shown). Here, the imaging for the hot spot measurement purpose can be carried out in 2D or 3D. In a case of 2D imaging, the slice plane is set up to include the setting focal point thereon.

Then, the system controller 9 controls the phase control circuits 11 and the driving circuits 12 to irradiate the ultrasound from the ultrasound transducer 2 while controlling the intensity and irradiation time to be in ranges of not causing the degeneration according to the above equation (1).

On the other hand, under the control of the system controller 9, the T1 weighted image is imaged similarly as above, either continuously since a time prior to the ultrasound irradiation, or during the ultrasound irradiation such as after three seconds since the start of the ultrasound irradiation.

Then, the difference between the obtained T1 weighted image and the reference image stored in the memory is calculated to obtain a hot spot image.

Here, there is no need to calculate the difference in a case where the tissues were uniform when the reference image was imaged, or in a case where the temperature change sensitive imaging can be carried out by adjusting the pulse sequence appropriately such that the sufficient temperature change appears on the obtained T1 weighted image itself. It is also possible to calculate the changes of the signal values obtained by the pulse sequence in advance, and identify the hot spot as a portion at which the change exceeds the prescribed threshold.

From this hot spot image, the peak point or a region with change exceeding the prescribed threshold is extracted as an image of the hot spot 6, which is superimposed onto the MR image of FIG. 3A obtained at the beginning, as shown in FIG. 3B.

Then, a displacement of a peak point of the observed hot spot 6 from the original setting focal point 7 is detected. Here, in a case of the 2D imaging, the displacement of the peak point within the slice plane can be detected from one MR image, and the displacement in a direction perpendicular to the slice plane can be detected by carrying out another hot spot imaging on a plane perpendicular to the slice plane which passes through the detected peak point.

Alternatively, when the difference between the temperature change at the peak point and the predicted temperature increase is below a prescribed threshold, it can be judged that the peak point of the hot spot 6 is not contained in the slice plane. Also, even in a case of the 2D imaging, when the multi-slice imaging is possible, a central slice plane is set up to contain the setting focal point such that the peak point on the central slice plane can be detected, and then the peak point in the slicing direction can be obtained from the change of the pixel representing the detected peak point among the slice planes.

In a case the detected displacement exceeds a prescribed tolerable range, the danger is notified to an operator by a warning sound, a screen display of a warning color or text, etc., while a safety circuit (not shown) is activated to stop the irradiation of the intense ultrasound. Alternatively, the setting of the focal point 7 can be adjusted to place the hot spot at the original setting focal point, and then the measurement of the hot spot can be repeated.

In this manner, when the hot spot coincides with the setting focal point position within a prescribed range, the irradiation level of the ultrasound is increased to the treatment level to heat up the treatment target at the hot spot over 80° C. for example, so as to thermally degenerate the treatment target to death.

Thereafter, the position of the setting focal point 7 is moved to subsequent treatment targets sequentially and the similar operation as described above is repeated for each treatment target.

In the above procedure, in a case where the hot spot 6 cannot be generated when the ultrasound at a reduced power is irradiated, it is either a malfunction of the ultrasound generator or the ultrasound transducer, or a dislocation of the coupling, or else an abnormality such as an extreme refraction, de-focusing, etc. of the ultrasound. In either case, the system controller 9 controls the system to output the warning similar to that used in the above procedure.

At an end or in a middle of the original treatment plan, the irradiation of the ultrasound is stopped and the progress of the treatment is observed by taking the MR image in a vicinity of the treatment portion and checking the change in the living body on the MR image in a manner similar to that described above. During this operation, the applicator 1 remains to be attached to the patient 3. At this point, by subtracting the data obtained here from the data of the T2 weighted image stored in the memory before the treatment began, it becomes possible to confirm the thermally degenerated region clearly, so that it becomes possible to judge whether the sufficient treatment had been carried out or the re-treatment is necessary as the treatment was insufficient. This confirmation operation can be incorporated into the treatment table from the beginning, such that the necessary MR imaging takes place automatically at prescribed time intervals.

When it becomes possible to judge that the sufficient treatment had been completed according to the treatment effect check using the MRI, the operator terminates the treatment. At this point, the system controller can call up the record of the treatment conditions from the memory, and output the treatment record from the CRT 10.

Figure 4:
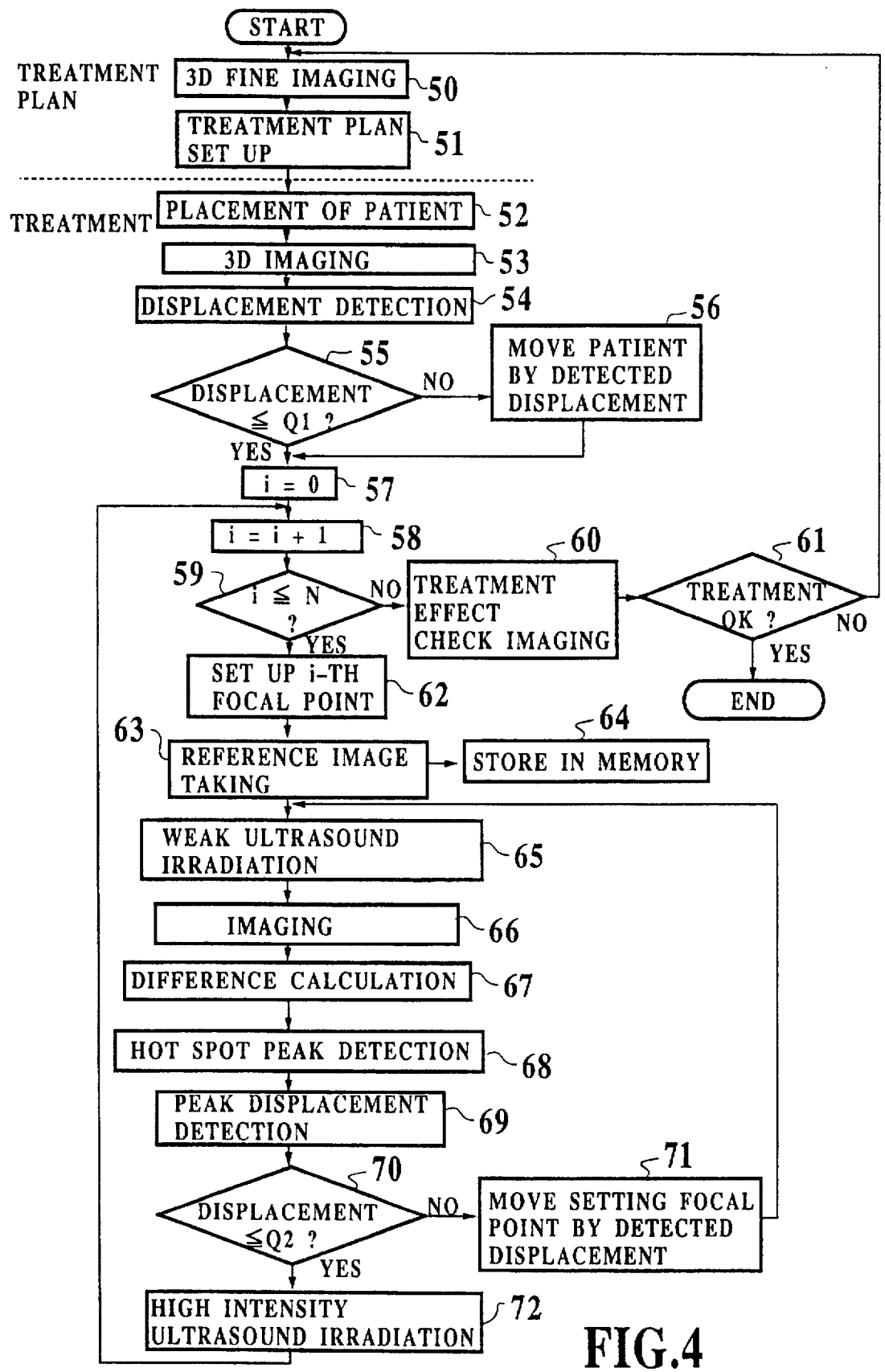
FIG. 4 is a flow chart for one operation of the apparatus of FIG. 1.
Figure 5:
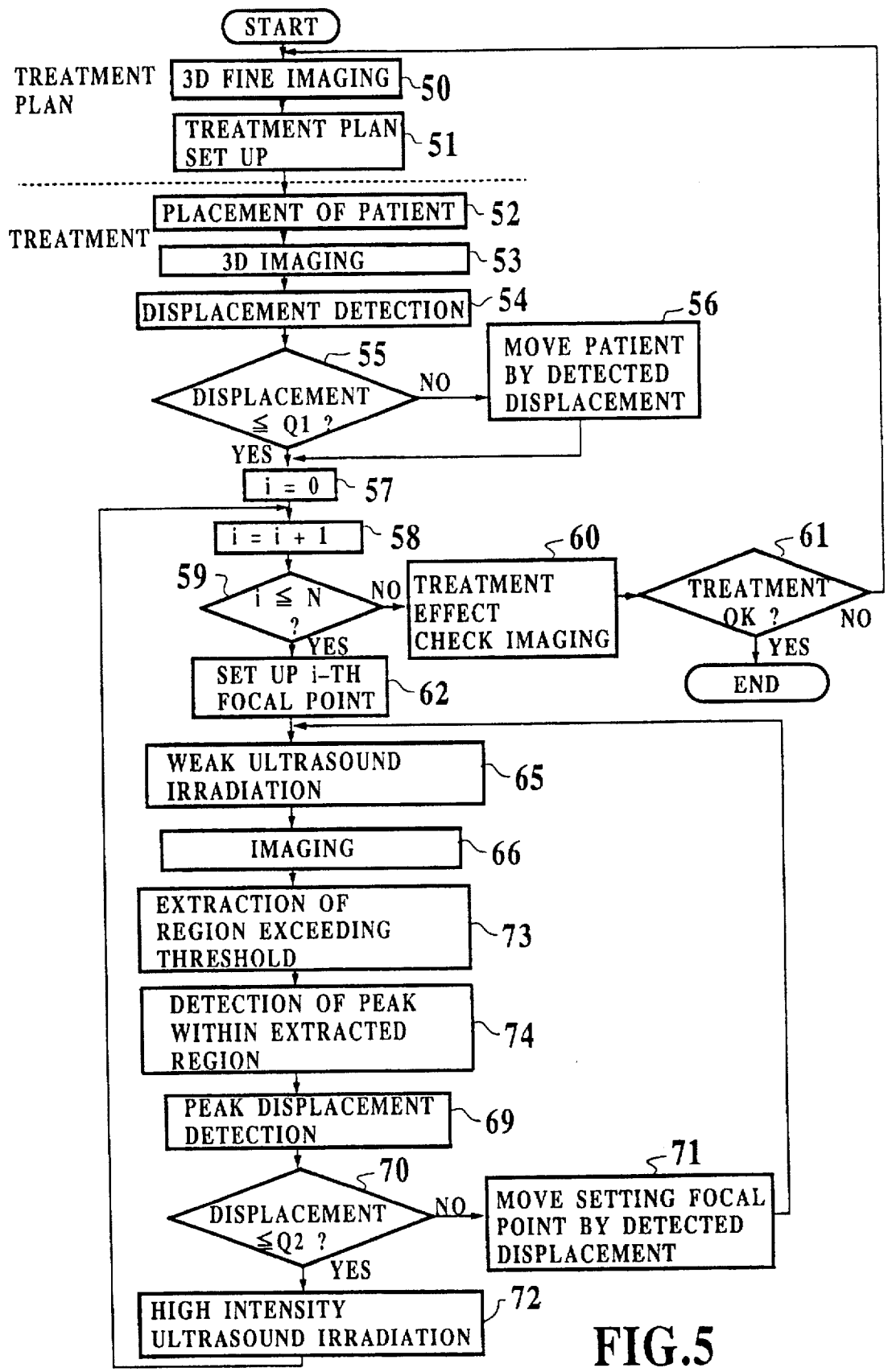
FIG. 5 is a flow chart for alternative operation of the apparatus of FIG. 1.

The above described operation according to this first embodiment can be summarized as the flow charts of FIGS. 4 and 5, where FIG. 4 describes a procedure for measuring the hot spot from the difference with respect to the reference image, while FIG. 5 describes a procedure for measuring the hot spot as that which is smaller than the predicted image signal change due to the temperature.

Namely, the operation according to the flow chart of FIG. 4 proceeds as follows.

First, the 3D fine imaging of the patient is carried out at the step 50, and the treatment plan is set up according to the obtained 3D MR image at the step 51. Here, N focal points of the ultrasound to be used in the treatment are set up. This completes the treatment plan stage.

Next, in the treatment stage, the patient is placed inside the MRI gantry at the step 52, and the 3D imaging of the patient is carried out at the step 53. Then, the displacement between the 3D MR image obtained at the step 53 and the 3D MR image used at the step 51 in setting up the treatment plan is detected at the step 54. In a case where the detected displacement is greater than a prescribed threshold Q1 at the step 55, the patient is moved as much as the detected displacement at the step 56, whereas otherwise this step 56 is skipped.

Then, a counter i is set to 0 initially at the step 57, and this counter is incremented by one at the step 58. If the counter i is greater than the number N of setting focal points at the step 59, the imaging for the treatment effect check is carried out at the step 60, and whether the sufficient treatment had been carried out or not is judged at the step 61. If so, the treatment operation is terminated, whereas otherwise the operation returns to the step 50 to repeat the treatment again.

When the counter i is not greater than N, the i-th focal point is set up at the step 62. Then, the reference image is taken at the step 63 and stored in the memory at the step 64. Meanwhile, the weak ultrasound is irradiated onto the patient at the step 65, and the MR image under the weak ultrasound irradiation is obtained at the step 66.

Next, the difference between the MR image obtained at the step 66 and the reference image obtained at the step 63 and stored at the step 64 is obtained at the step 67, and the hot spot peak is detected from the obtained difference at the step 68, and then the displacement of the detected hot spot peak from the setting focal point is detected at the step 69.

When the detected displacement is greater than a prescribed threshold Q2 at the step 70, the setting focal point is moved as much as the detected displacement at the step 71 and the operation returns to the step 65, whereas otherwise the high intensity ultrasound is irradiated onto the patient to carry out the treatment at the step 72, and then the operation returns to the step 58 to repeat the similar operation for the next setting focal point.

On the other hand, the operation according to the flow chart of FIG. 5 proceeds as follows. Here, those steps which are substantially equivalent to those in the flow chart of FIG. 4 are given the same reference numerals in the figure and will not be described in detail again.

In this case, the steps 50 to 62 are identical to those in the flow chart of FIG. 4.

After the step 62, the operation directly proceeds to the steps 65 and 66 which are also identical to those in the flow chart of FIG. 4.

Next, after the step 66, a region in the MR image obtained at the step 66 which is exceeding a threshold given by the image signal is extracted at the step 73, and a peak within the extracted region is detected at the step 74. Then, the operation proceeds to the steps 69 to 72 which are also identical to those in the flow chart of FIG. 4.

It is to be noted that, in the first embodiment described above, a body cavity coil to be inserted within the patient may be used instead of the RF coil 20. In addition, the phased array type ultrasound transducer 2 may be replaced by the annular array type ultrasound transducer, and the focal point may be moved by mechanically controlling the applicator 1.

Now, various modifications of the first embodiment of an ultrasound medical treatment apparatus according to the present invention will be described in detail.

Figure 6:
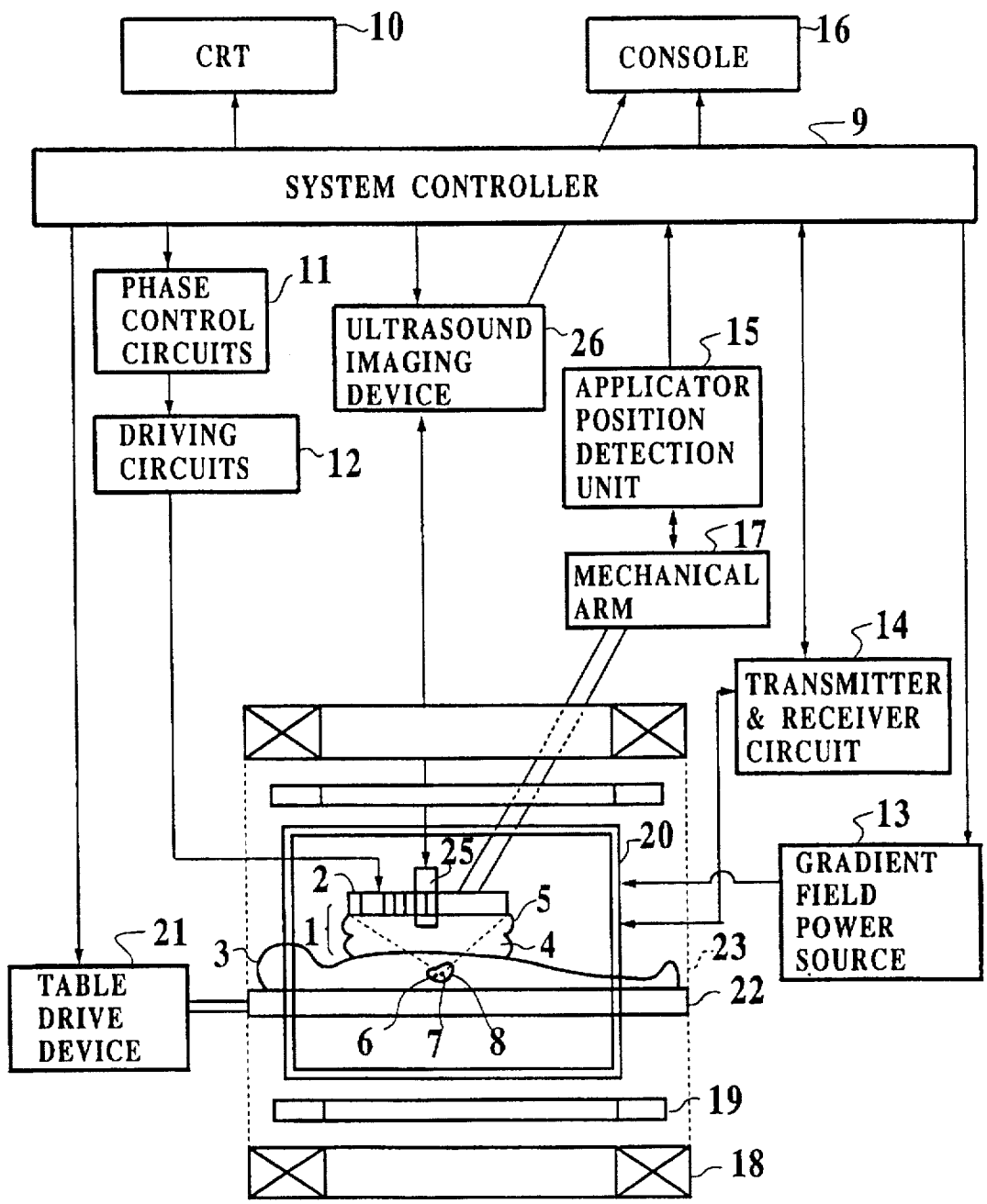
FIG. 6 is a schematic block diagram of a modified configuration for the apparatus of FIG. 1.

First, the ultrasound medical treatment apparatus of the first embodiment of FIG. 1 can be modified to further incorporate the ultrasound imaging device as shown in FIG. 6. Here, those elements which are equivalent to the corresponding elements in the first embodiment will be given the same reference numerals in the figure and their descriptions will be omitted.

In this case, an ultrasound probe 25 is attached at a center of the ultrasound transducer 2 and connected with a ultrasound imaging device 26 controlled from the system controller 9 such that the ultrasound tomographic image of the interior of the patient 3 can be observed in real time. This ultrasound probe 25 is formed to be slidable back and forth as well as rotatable around its axis. By providing means for obtaining the relative position of the ultrasound probe 25 and the focal point 7 of the ultrasound generated from the ultrasound transducer 2, it is possible to indicate the focal point position on the ultrasound tomographic image obtained by the ultrasound imaging device 26. It is also possible to indicate the position of the ultrasound tomographic image on the 2D or 3D MR image obtained by the MRI part, so as to utilize the ultrasound tomographic image along the treatment plan set up in accordance with the MR image.

Here, it is to be noted that the applicator 1 is not necessarily limited to be used as an upper side approaching type as shown in FIG. 6, and can be used as a lower side approaching type by controlling the mechanical arm 17 appropriately.

Now, as the hot spot 6, it suffices to determine a region with a relatively high temperature, so that there is no need to indicate the temperature change quantitatively, and it is only required that the hot spot 6 be clearly identifiable in the image reflecting the temperature change. For example, in the T1 weighted image obtained by the MRI, it is difficult to indicate the relaxation time T1 quantitatively by just one such image, but it exhibits a sufficient change in proportion to the temperature so that a single T1 weighted image can be used for the purpose of the hot spot measurement.

In this case, the intensity and irradiation time for the ultrasound irradiation are set up to be in ranges of not causing the degeneration to obtain the temperature profile satisfying the above equation (1).

For example, the relationships among the intensity, irradiation time, and the temperature profile are obtained experimentally in advance and stored in a memory (not shown), and the survival rate according to the temperature profile is calculated by using the above equation (1), to confirm that the resulting survival rate is within a setting range before the irradiation.

Alternatively, there are experimental results indicating that, in a case of an instantaneous heating (one second or shorter), the product of the ultrasound focal point intensity, irradiation time, and frequency is going to be proportional to the temperature change as can be expressed by the following equation (2):

$$I_p \times t \times f = 50 \Delta T \quad (2)$$

where $I_p$ is the focal point intensity, t is the irradiation time, and f is the frequency, so that the temperature increase $\Delta T$ can be calculated from this equation (2). The actual temperature is expected to be lower than the calculated temperature, and will decrease exponentially with a certain time constant after the irradiation. This time constant depends on the type of the tissue, and can be determined in advance experimentally. Thus, when the temperature profile predicted in this manner is substituted into the above equation (1), is the survival rate is within the setting range, the degeneration is not going to occur.

In a case of the irradiation time over one second, the proportional relationship of the above equation (2) does not hold, but within the range in which the influence of the blood flow is ignorable, the living body heat transport equation can be solved to obtain the distribution of the heat sources, and it is possible to calculate the temperature profile which is in agreement with the experimental results for the irradiation time below twenty seconds.

Instead of obtaining the temperature profile from the calculations as described above, it is also possible to obtain the quantitative temperature change distribution intermittently by utilizing the above described temperature distribution measurement technique such as the temperature measurement using the water proton chemical shift, and the obtained result can be substituted into the above equation (1) to calculate the survival rate distribution every time the image is obtained. Then, the irradiation conditions can be controlled such that the irradiation power is decreased or the irradiation time is shortened when the survival rate becomes lower than the setting range.

In the above, it has been assumed that the setting focal point and the peak point of the hot spot are coinciding, but it has experimentally confirmed that there is a tendency for the hot spot to be displaced toward the ultrasound irradiating side due to the influences of the dissipation within the living body, etc. Also, in a case of causing the degeneration in a region irradiated by the intense ultrasound, due to the degeneration and the cavitation caused at an early stage of the irradiation, the ultrasound is not going to reach beyond them, and it has been experimentally observed that the degenerated region tends to spread toward the ultrasound irradiating side. According to such an observation, it is possible to experimentally determine a region at which the degeneration can be caused when heating is applied at certain irradiation conditions, and after the positional relationship of this region with respect to the setting focal point and the hot spot is comprehended, the treatment region can be set up to be aligned with the predicted degeneration region, such that the degeneration region can be predicted from the measured hot spot.

Also, instead of making the temperature change measurement using the T1 weighted image, it is also possible to use any temperature dependent parameter that can be observed to sense the temperature change according to the change of the observed parameter. For example, any of the above mentioned parameters of the MRI can be utilized. In a case of the temperature measurement utilizing the temperature change obtained by the water proton chemical shift, it is possible to determine the change due to the temperature change quantitatively, so that the temperature change can also be determined quantitatively. The same applied also to the other imaging diagnostic apparatus such as X-ray CT and ultrasound imaging devices. For example, the temperature dependence of the sonic speed of the ultrasound can be utilized to extract the change due to the temperature change as an image.

In order to extract the image change due to the temperature, it is going to be necessary to take a difference between the images before and after the heating, pixel by pixel. However, when the patient moves during the heating, the obtained difference will be that between noncorresponding pixels, and the large error can be caused especially at the tissue boundaries. Such a body movement of the patient can be compensated as follows.

Figure 7:
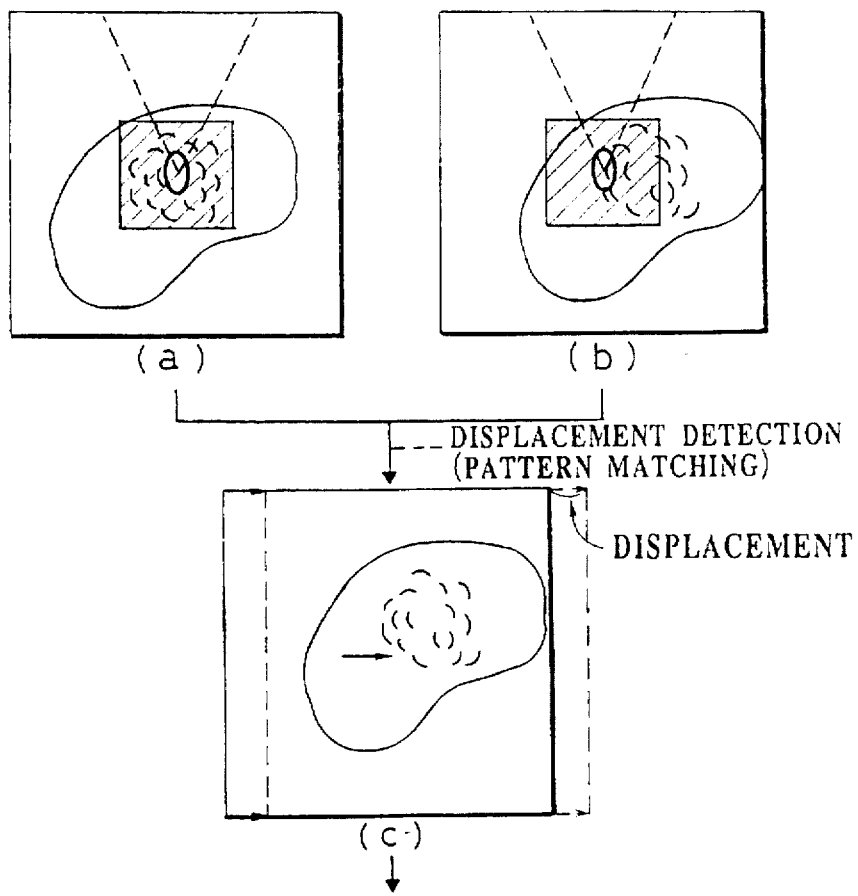
FIG. 7 is sequential illustrations of images used in the apparatus of FIG. 6 in obtaining a hot spot image.

Namely, the heated region within one image is limited in a vicinity of the focal point, so that the image data outside of the region in a vicinity of the focal point can be considered as not receiving the influence of the heating. Consequently, as shown in FIG. 7, the pattern matching of the images before and after the heating shown in (a) and (b) of FIG. 7 can be made according to the image data outside of the shaded region set up in vicinity of the focal point, so as to detect the displacement between these images. Then, these images can be aligned according to the detected displacement as shown in (c) of FIG. 7, and the difference can be taken in this aligned state, to obtain the hot spot 6 without the influence of the body movement as shown in (d) of FIG. 7.

Also, instead of using the image obtained before the ultrasound irradiation as the reference image as described above, it is possible to use the previously taken image as the reference image and to obtain the temperature change from the integrated change in the difference image of the previously taken image and the presently taken image, so as to reduce the influence of the body movement. By applying the pattern matching from time to time to compensate the body movement in such a manner, it becomes possible to follow the large body movement. In particular, when the chemical shift temperature measurement is employed, as the temperature resolution can be set up arbitrarily in a case of measurement using the phase mapping, it becomes possible to make the measurement of the temperature distribution at the fine temperature resolution over a wide range, by obtaining the temperature distribution as the integration of results obtained by setting the measurement temperature width in a narrow range which can only satisfy the temperature change between one imaging interval.

Figure 8:
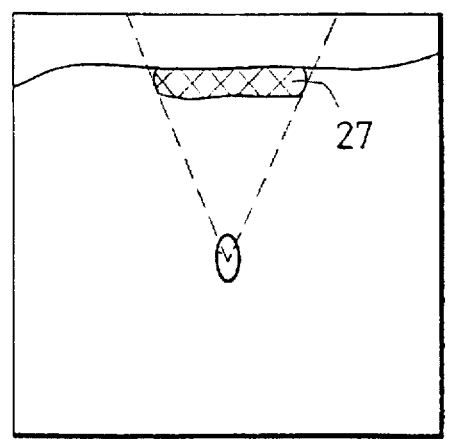
FIG. 8 is an illustration of an exemplary display used by the apparatus of FIG. 6 for indicating a dangerous region.

It is to be noted that the idea of the survival rate according to the above equation (1) can also be utilized in the evaluation of the safety during the entire treatment as follows. Namely, by constantly obtaining the temperature distribution over the wide range including the irradiation route and focal point, the survival rate at each pixel can be calculated according to the past temperature profile. Then, by setting the threshold for the dangerous survival rate in advance, the occurrence of the portion reaching to this threshold can be noticed to the operator by displaying a colored region 27 as shown in FIG. 8 as the dangerous survival rate region, or by means of an alarm sound, while the irradiation is stopped or shifted away from that portion to cool down that dangerous portion. In this manner, it is possible to prevent the hyperthermia type influence from being applied to the normal tissues. At this point, the calculation range can be limited to the particularly interested point such as the body surface, or a portion at which the reflection from the intestinal wall can be expected.

Also, instead of calculating the survival rate according to the above equation (1), it is also possible to set up the threshold for the temperature itself, such that the warning to the operator similar to that described above is given when the temperature reaches to this threshold, while the irradiation is stopped or shifted away from that portion to cool down that dangerous portion.

In addition, the temperature measurement can be utilized not just in a case of using the irradiation energy level below the treatment level as in the hot spot measurement but also in a case of using the irradiation energy level at the treatment level for the purpose of checking the resulting heating.

In such a case, however, the measured parameter can be changed due to the degeneration of the treatment target, and this change is expected to be superposed on the actual temperature change. For this reason, the image can be obtained in the degenerated state in advance, and the change due to the degeneration can be subtracted from the image obtained during the heating so as to reduce the influence due to the degeneration. Alternatively, the correspondence between the image change and the temperature can be obtained in advance for regions including the region to be degenerated, and the temperature distribution can be obtained by the calculation according to this correspondence.

It is to be noted that the schemes described above are equally applicable to the thermal medical treatment other than the ultrasound medical treatment described here. For example, in the heating treatment using the laser, it is also possible to check the heating region by measuring the hot spot while heating at conditions for not causing the degeneration which are determined in advance. Similarly, the heating region can be checked in the heating treatment using the microwave.

Next, the second embodiment of an ultrasound medical treatment apparatus according to the present invention will be described in detail.

In this second embodiment, the configuration of the apparatus is essentially similar to that of the first embodiment described above, so that its description will not be repeated here.

Figure 9:
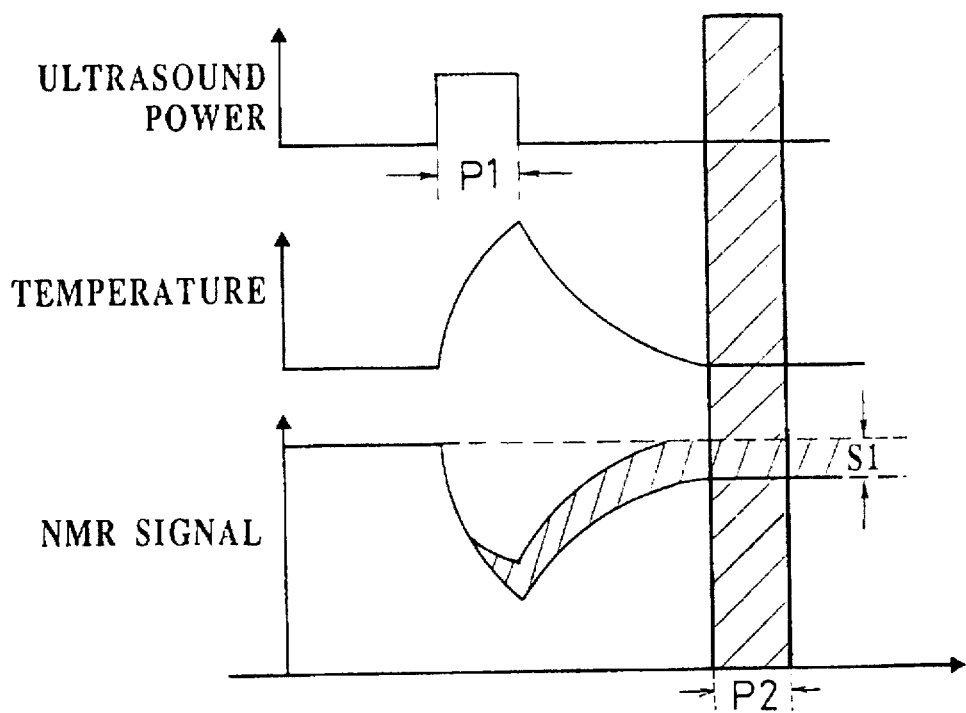
FIG. 9 is a timing chart for explaining an operation of a second embodiment of an ultrasound medical treatment apparatus according to the present invention.

In this second embodiment, in order to obtain the image of the degeneration, the image is taken after the temperature of the heated portion has returned to the normal temperature. Namely, as indicated in FIG. 9, by taking the interval between the irradiation period P1 and the imaging period P2 over a prescribed length of time determined by the heating conditions such as the irradiation energy and the irradiation time, the temperature can return to the normal temperature and the change on the image can be limited to the irreversible change due to the degeneration alone.

According to the animal experiment done by Vallancien et al. (Eur. Urol. 1991; 20; 211–219), the pig's liver heated up to 108° C. by the ultrasound irradiation of 0.25 second returns to the normal temperature within about eight seconds. Thus, by setting the imaging period P2 at a shaded region in FIG. 9 which starts after the sufficient amount of time such as eight seconds for example from the irradiation period P1, it becomes possible to obtain the image resulting from the change S1 in the NMR signals due to the degeneration alone.

Here, however, in the living body, there is a possibility for the edema to appear as the living body reaction after several tens of minutes since the heating treatment, and this edema can make it difficult to take the image of the degeneration, so that in order to obtain the image of the degeneration as purely as possible, the imaging should be carried out after the temperature has returned to the normal temperature, and before the edema appears.

In a case of carrying out the treatment intermittently by sequentially shifting the treatment position over a large tumor, it is timewise inefficient to take the image after each ultrasound irradiation, so that the ultrasound treatment can be carried out while obtaining the MR images sequentially at intervals of several tens of ms by using the ultra high speed pulse sequence and checking the treatment effect (degeneration) on the portion which has returned to the normal temperature within the obtained MR images.

Figure 10:
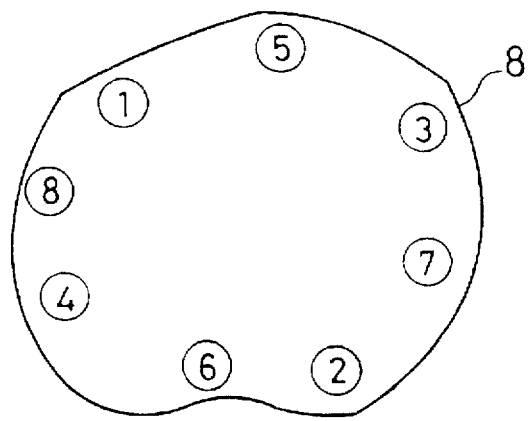
FIG. 10 is an illustration of a treatment target for explaining an operation in the second embodiment.
Figure 11:
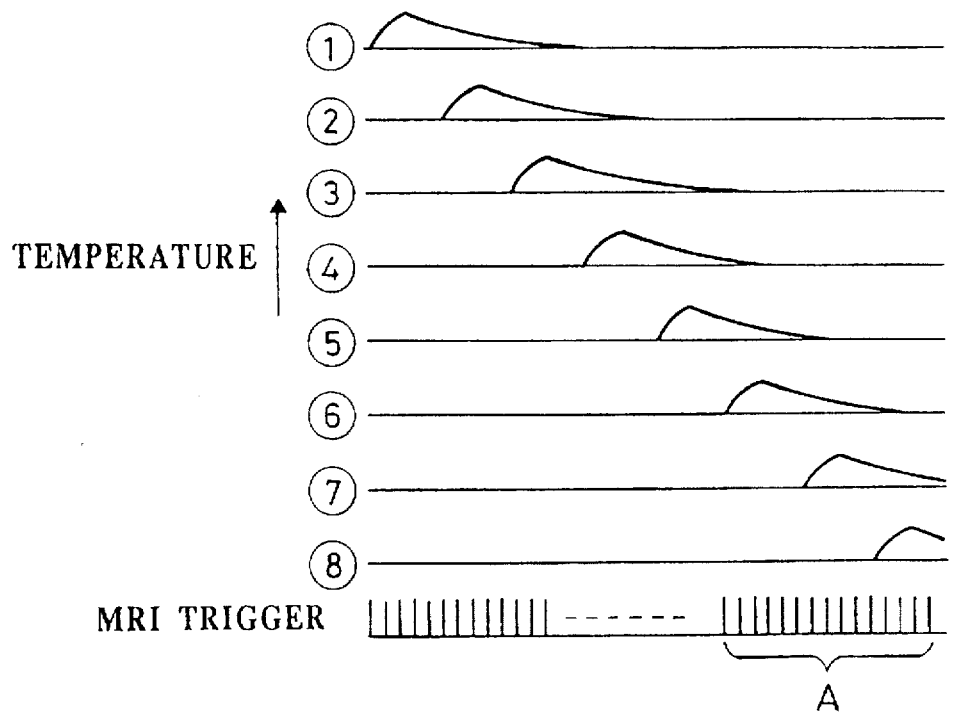
FIG. 11 is a timing chart for explaining an operation of the second embodiment.

For example, in a case of treating the treatment target (tumor) 8 as shown in FIG. 10, the ultrasound treatment can be carried out at the treatment portions shifted in an order indicated by the encircled numbers as shown in FIG. 10. In such a case, the treatment positions can have the temperature characteristics as indicated in FIG. 11. According to this FIG. 11, the temperature of the first treatment position has returned to the normal temperature by the time the eighth treatment position is to be treated, so that the treatment effect on the first treatment position can be checked from the MR image taken at a period A indicated in FIG. 11.

Also, by making the temperature measurement in real time by using the chemical shift temperature measurement, it becomes possible to check the treatment effect without the influence of the temperature from the MR image of the degeneration obtained when the temperature is known to have returned to the normal temperature.

In operating this ultrasound medical treatment apparatus as a whole, the operator can operates the track ball and the mouse by both hands, such that the imaging slice plane is selected by the track ball operated by the left hand, while the selection and determination of the treatment position as well as the start of the ultrasound irradiation can be specified by the mouse operated by the right hand. In this manner, the 3D treatment target can be treated while checking the treatment effect.

Here, it becomes possible to check the treatment effect easily by displaying the already treated portion after a prescribed period determined by the heating conditions in different color, while also changing displayed colors for the presence or absence of the degeneration as well as for different levels of the degeneration.

The image data obtained by the imaging are stored in the memory and can be called up at a time of checking the treatment effect after the treatment is over. Here, it is possible to extract parts of the images containing the position to be treated by one ultrasound irradiation from the images, and synthesize the extracted parts for the purpose of checking the treatment effect.

In a case of carrying out the treatment automatically according to the treatment plan set up in advance, it is possible to carry out the automatic treatment accurately while judging the treatment effect as follows. Namely, for each treatment at one focal point, the occurrence of the degeneration at the treatment portion in the image obtained after the prescribed period determined by the heating conditions is checked with respect to the threshold determined from the past experimental data, and then the feed back for commanding the re-treatment is returned to the system controller in a case the treatment is insufficient.

In the imaging of the degeneration after the temperature has returned to the normal temperature as described above, the treatment effect immediately after the irradiation of the ultrasound cannot be judged. Also, in a case of heating a larger region over a certain period of time, a considerable amount of time is required until the temperature returns to the normal temperature, so that it is necessary to extract the degeneration alone in the high temperature state. In such a case, the degeneration can be judged as follows.

Namely, by utilizing the characteristics of the image signal known from the experiences, the degeneration can be judged from the MR image obtained at the time of the temperature increase. For example, the various characteristics such as the temperature increase characteristic with respect to the irradiation time as shown in FIG. 9, the image signal strength characteristic with respect to the imaging sequence, and the threshold for causing the degeneration for the general heating conditions can be stored in the memory in advance, such that at a time of the ultrasound irradiation, the occurrence of the degeneration and the level of the degeneration can be monitored in terms of the measured image signal strength.

Figure 12:
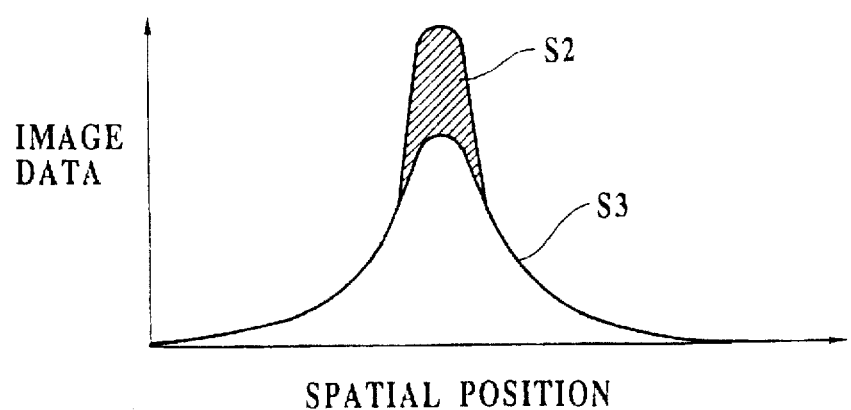
FIG. 12 is a graph of image data used in the second embodiment for explaining another operation in the second embodiment.

Similarly, as shown in FIG. 12, by predicting the change S3 due to the temperature alone in the measured image data, the measured data containing the change S2 due to the degeneration can be corrected.

Figure 13:
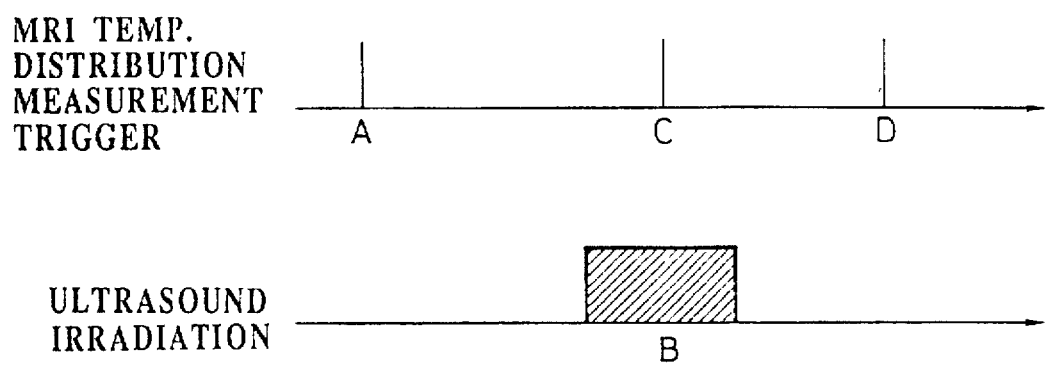
FIG. 13 is a timing chart for explaining another operation in the second embodiment.

Namely, the temperature distribution can be measured by using the temperature distribution measurement by the chemical shift in the procedure shown in FIG. 13, and the relaxation times measured at the high temperature can be corrected by the measured temperature distribution to obtain the change due to the degeneration alone as follows. First, at the point A, the image is obtained while the temperature distribution is measured before the heating treatment. Then, at the point B, the heating treatment is carried out by the ultrasound irradiation. During and after this heating treatment, at the points C and D, the image and the temperature distribution are also obtained. Then, the influence of the temperature is corrected according to the temperature dependency of the image (such as T2 weighted image). In this case, the temperature distribution measurement obtains the absolute temperature calculated from the displacement with respect to the fat spectrum, but in a case the influence of the magnetic field inhomogeneity is not large due to the degeneration, the temperature measurement utilizing the phase data can be used to obtain the relative temperature distribution with respect to the temperature distribution before the heating treatment, in order to reduce the measurement time.

Also, without measuring the temperature distribution as described above, on an assumption that the temperature distribution at a certain amount of time after the ultrasound irradiation has a uniform shape with only amplitude changing with respect to the irradiation intensities, the correction can be made as follows.

First, the ultrasound weak enough not to cause the degeneration is irradiated, while the MR images are obtained continuously. Then, at a time of the actual heating treatment, the image data are also obtained similarly. Then, the image obtained for the weak ultrasound is changed in proportion to the ultrasound irradiation energy to calculate the change of the image due to the influence of the temperature alone, and the change due to the degeneration alone can be extracted from the image obtained at a time of the heating treatment according to the calculated change due to the temperature.

Also, after the ultrasound irradiation, the temperature distribution gradually spread spatially due to the influences of the distribution, etc. Thus, by applying the ultrasound intense enough to cause the degeneration, and the change of the image due to the temperature change for the region near the focal point at which the degeneration is caused is predicted by the fitting of the temperature distribution with respect to the temperature distribution known from experiences, or by the polynomial approximation of the temperature distribution, for the image data in a region slightly distanced from the focal point at which the temperature is changing but the degeneration is not caused. Then, the change due to the degeneration can be extracted by subtracting the predicted change due to the temperature change from the measured image.

Here, the image data for the the qualitative image such as T1weighted image and the T2weighted image are used so that the extracted result concerning the presence or absence of the degeneration can also be displayed qualitatively by the simple subtraction at each picture element.

In order to extract the level of the degeneration quantitatively, the influence due to the temperature change can be corrected as in the above by calculating the relaxation times such as T1 and T2 for each picture element by solving the simultaneous equations from a plurality of images with different repetition times and the echo times obtained by the ultra high speed sequence within a sufficiently short period in which the temperature change can be ignored.

Alternatively, assuming that a sum of the inverse of the relaxation time due to the temperature change and the inverse of the relaxation time due to the degeneration is equal to the inverse of the actually measured relaxation time, the relaxation time due to the degeneration can be calculated from this relationship, and the quantitative image of the degeneration can be obtained.

In the spin echo scheme, the signal strength S can be expressed in terms of the spin density A, the relaxation times T1 and T2, the repetition time TR, and the echo time TE, as in the following equation (3).

$$S = A\,(1-\exp(TR \times T1))\exp(TE \times T2) \qquad (3)$$

Figure 14:
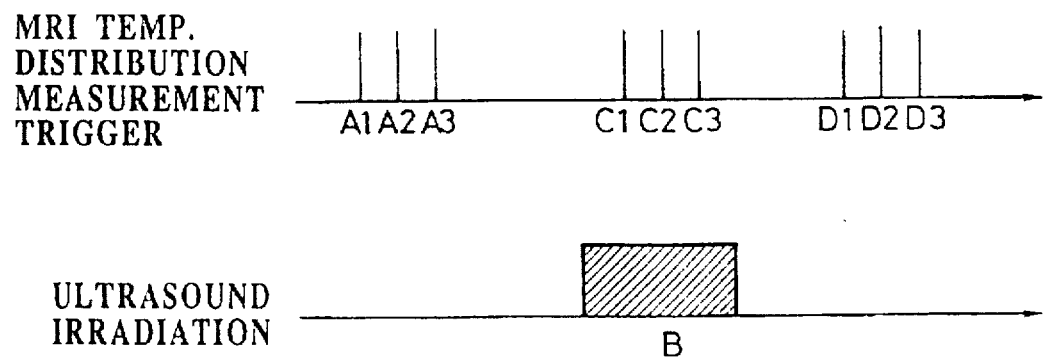
FIG. 14 is another timing chart for explaining still another operation in the second embodiment.
Figure 15:
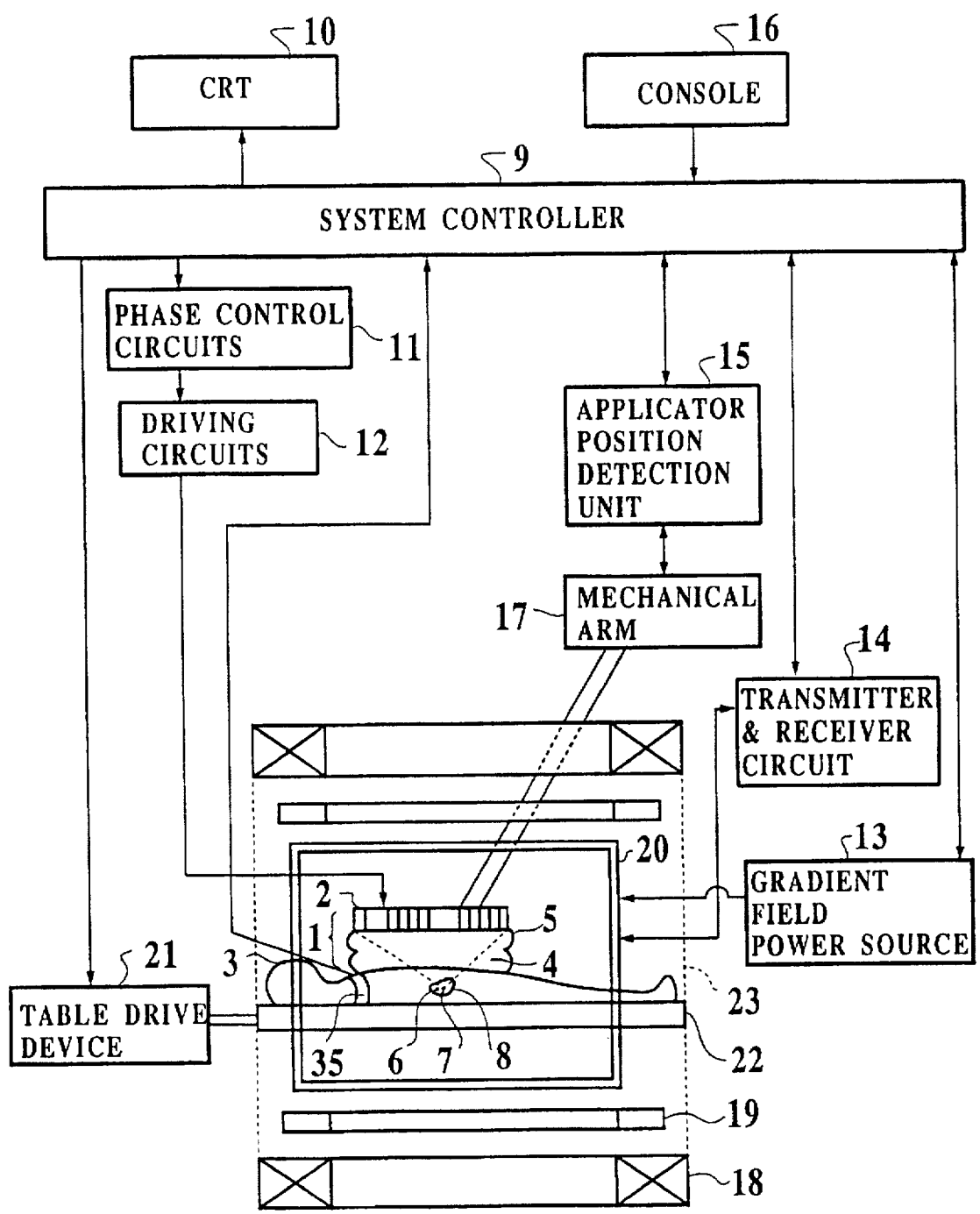
FIG. 15 is a schematic block diagram of a third embodiment of an ultrasound medical treatment apparatus according to the present invention.

Then, for example, as shown in FIG. 14, at each of before, during, and after the treatment, a plurality (three in FIG. 14) of imagings (A1, A2, and A3; C1, C2, and C3; D1, D2, and D3) are carried out in such a manner that for the first and second imagings the echo time TE is fixed while the repetition time TR is changed, and the echo time TE is changed for the third imaging. Then, the echo signal for the first imaging is purely affected by the decaying term of T2 alone, so that by taking the ratio of the first and second image data and substituting it into the expression for it obtained from the above equation (3), it becomes possible to obtain T2. Then, after the third imaging, the obtained T2 is substituted into the above equation (3) and the simultaneous equations for the first and third image data can be solved for the spin density A and the relaxation time T2.

In this manner, the relaxation times are calculated immediately after the imagings of each group (A, C, and D), to obtain the relaxation time images. Here, the calculation can be limited to a region in vicinity of the focal point at which the change can be expected. Meanwhile, the temperature measurement is also carried out for all the groups, and the temperature distribution is determined as the measured result as it is when the temperature change within each group is in an ignorable range, or as the average of the measured results. Then, using these temperature distribution data, the relaxation times measured during the temperature increase are corrected. When the temperature change within each group is large, the measure such as the shortening of the measurement interval is taken. The measurement interval (repetition time) and the echo time within each group are determined by the measurement target and the heating conditions.

It is to be noted that the schemes described above are equally applicable to the heating treatment other than the ultrasound medical treatment described here. For example, they are applicable to the heating treatment using the laser guided by the optical fibers. In particular, the extraction of the degeneration during the temperature increase is applicable to the heating treatment using the microwave.

Also, the change of the parameters such as the relaxation times due to the thermal degeneration has been utilized for the checking of the treatment effect above, but the change of the metabolism activity can be detected by using the spectroscopy for phosphorus in the hyperthermia in which the metabolism activity of cells are changed by the heating and the cells are eventually killed. For example, the change of the peak of ATP can be detected, and when its change is over the prescribed threshold, this information can be fed back as the treatment effect data as in the above, such that the treatment can be carried out while checking the treatment effect as in the above.

Next, the third embodiment of an ultrasound medical treatment apparatus according to the present invention will be described in detail. Here, those elements which are equivalent to the corresponding elements in the first embodiment of FIG. 1 will be given the same reference numerals in the figure and their descriptions will be omitted.

In this third embodiment, the ultrasound medical treatment apparatus of the first embodiment of FIG. 1 is slightly modified to further incorporate a chest belt 35 attached on the chest portion of the patient 3 for detecting the respiration waveform of the patient 3. Namely, in setting up the treatment plan for the treatment target such as the liver cancer at which the motion due to the respiration is considerable, it is preferable to use the image data obtained at the time phase near the expiration end in order to achieve the reproducibility of the images. For this reason, in this third embodiment, the chest belt 35 is provided to detect this time phase, such that the imaging timing can be controlled appropriately by the system controller 9 to which the detected respiration waveform signal is supplied from this chest belt 35.

When the treatment started according to the treatment plan, at the inspiration end, the tagging is made at a predetermined treatment start position, and the focal point 7 of the ultrasound is set to the treatment start position and the intense ultrasound irradiation is started.

Here, the tagging is the magnetic marking technique developed for the MRI (Zerhouni E. A., et al. Radiology 1988;169;59–63), in which the marking is incorporated on the MR image by using a special imaging sequence. More specifically, when a predetermined plane alone is selectively applied with 90° pulse before the imaging and then the normal imaging is carried out, the signal from the predetermined plane disappears and this portion appears as a black line (tag) on the obtained MR image. This line (tag) can be provided at any desired constant intervals in parallel, and the lattice shaped marking is also possible by making the tagging in the perpendicular direction instantaneously. It has also becomes possible recently to make the tagging in any desired 3D shape (C. J. Hardy, et al., J. Magnetic Resonance 1989;82;647–654).

Figure 16A:
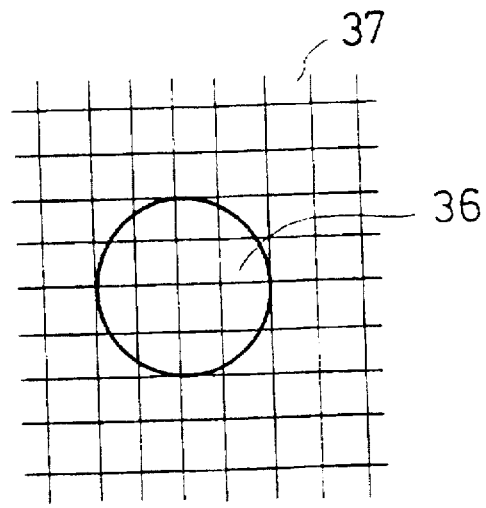
FIGS. 16A and 16B are illustrations of mesh shaped tag that can be used in the apparatus of FIG. 15.
Figure 16B:
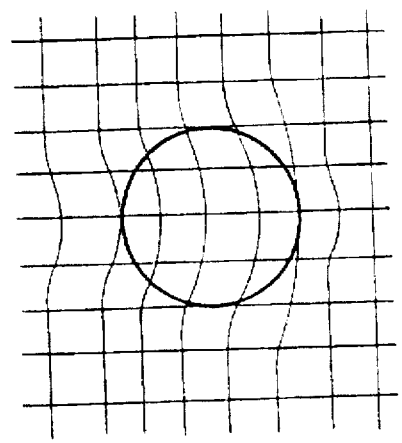

The tag can last for about one second, so that by taking the image within a prescribed time after the tagging, the movement during this period can be recognized from the flow of the tag. For example, in a case the mesh shaped tagging is made as shown in FIG. 16A at a time t0, if the object 36 is moving within the surrounding tissue 37, after an elapse of time t, the distortion on the mesh shaped tag as shown in FIG. 16B can be caused such that the movement of the object can be comprehended two dimensionally. Furthermore, by dividing the moving distance of the tag by the time t, it also becomes possible to obtain the moving speed of the object quantitatively.

Figure 17:
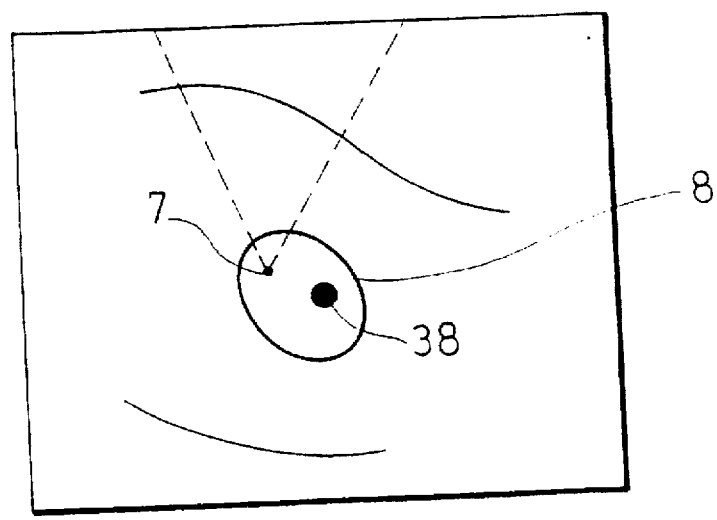
FIG. 17 is an illustration of a treatment region used in the apparatus of FIG. 17.

In this third embodiment, as shown in FIG. 17, the tag 38 in a point like shape is employed in order to make it easier to detect the position of the tag 38 in the MR image. Here, the detection of the position of the tag 38 can be achieved by detecting the lowest signal strength point within the MR image.

Then, after an elapse of time such as 0.8 second during which the tag 38 does not disappear, the system controller 9 carries out another imaging. At this point, if the treatment target (tumor) 8 has moved, a displacement between the tag 38 and the focal point 7 is caused. This displacement is detected by the system controller 9 which subsequently controls the ultrasound applicator to shift the focal point 7 to the position of the tag 38, and then the tagging is made there again. Hereafter, the similar operation is repeated during the treatment of the first treatment position.

After the treatment of the first treatment position is finished, at the timing of the expiration end, according to the treatment plan, the tagging is made at a next treatment position. Then, the same operation as in the case of the first treatment position is repeated.

In a case the displacement between the tag 38 and the focal point 7 becomes greater than a prescribed value, the abrupt body movement of the patient or the malfunction of the apparatus may have occurred, so that the system controller 9 stops the ultrasound irradiation, and notifies the operator by means of the warning display or the alarm sound.

It is to be noted that the chest belt 35 used in this third embodiment for detecting the respiration waveform can be replaced by the other respiration waveform detection means such as the impedance respiration monitor. Also, instead of the motion due to the respiration, this third embodiment can also be applied to the treatment of the heart muscle or the surrounding of the heart, by using the electrocardiogram similarly.

It is also to be noted that the shape of the tag 38 may not necessarily be the point shaped one used above, and the tagging can be made at an intersection of three planes instead, or around the contour of the treatment target tumor in order to assist the operator's comprehension.

Next, the fourth embodiment of an ultrasound medical treatment apparatus according to the present invention will be described in detail. Here, those elements which are equivalent to the corresponding elements in the first embodiment of FIG. 1 will be given the same reference numerals in the figure and their descriptions will be omitted.

Figure 18:
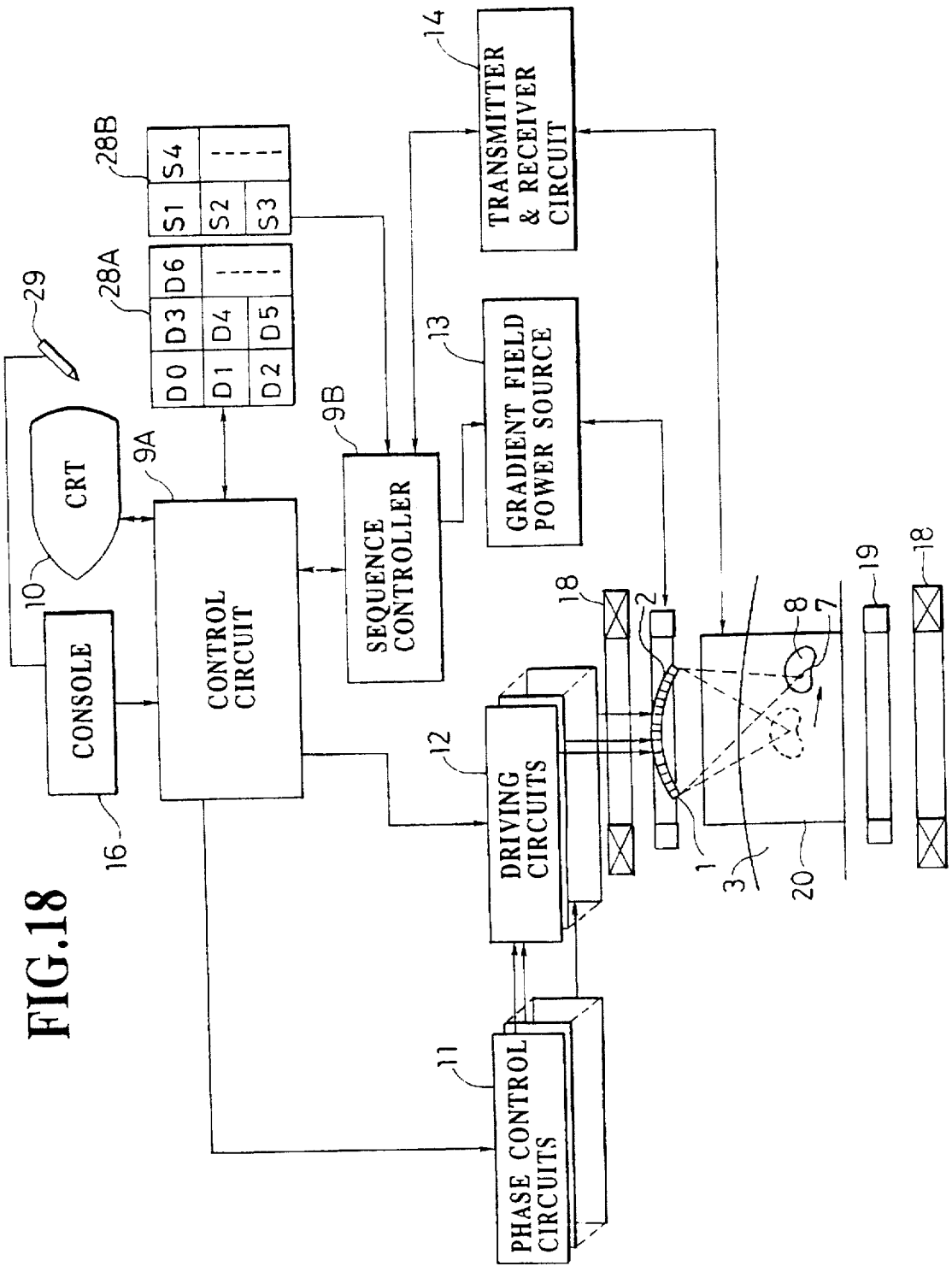
FIG. 18 is a schematic block diagram of a fourth embodiment of an ultrasound medical treatment apparatus according to the present invention.

In this fourth embodiment, as shown in FIG. 18, the system controller is divided into a control circuit 9A and a sequence controller 9B, and there is provided a memory 28A connected with the control circuit 9A for storing the 3D data D0, D1, etc. of the interior of the patient, a memory 28B connected with the sequence controller 9B for storing the sequence data S1, S2, etc., and a light pen 29 provided in conjunction with the CRT 10.

This fourth embodiment realizes the automatic focal point pursuit function as follows.

First, in order to depict the tumor at high resolution and contrast, the sequence data S1 for T2 weighted imaging stored in the memory 28B are used to carry out the T2 weighted imaging sequence according to which the sequence controller 9B controls the gradient field power source 13 and the transmitter and receiver circuit 14. Then, the obtained image data are stored as the 3D data D0 in the memory 28A and while being displayed on the CRT 10.

Then, the sequence data S2 for body temperature distribution measurement stored in the memory 28B is used to carry out the 3D temperature distribution data D1 before the ultrasound irradiation, to be stored in the memory 28A.

Next, the control circuit 9A controls the driving circuits 12 at low output to warm up the patient's body below 45° C. for short period of time at the level of not influencing the living body, to obtain the 3D data D2 to be stored in the memory 28A.

Then, the difference between the data D2 and D1 is taken and superposed onto the display of the data D0, so as to indicate a location at which the temperature has been increased, i.e., the focal point position, on the 3D image of the data D0. (Focal point positioning mode) As a result, the focal point can be set on the tumor accurately and the safe treatment can be carried out.

By utilizing the fact that the current ultrasound irradiation point can be determined by measuring the temperature increase point in this manner, the temperature increasing point can be known in real time such that the intense ultrasound focal point can be made to follow the treatment portion automatically.

Figure 19A:
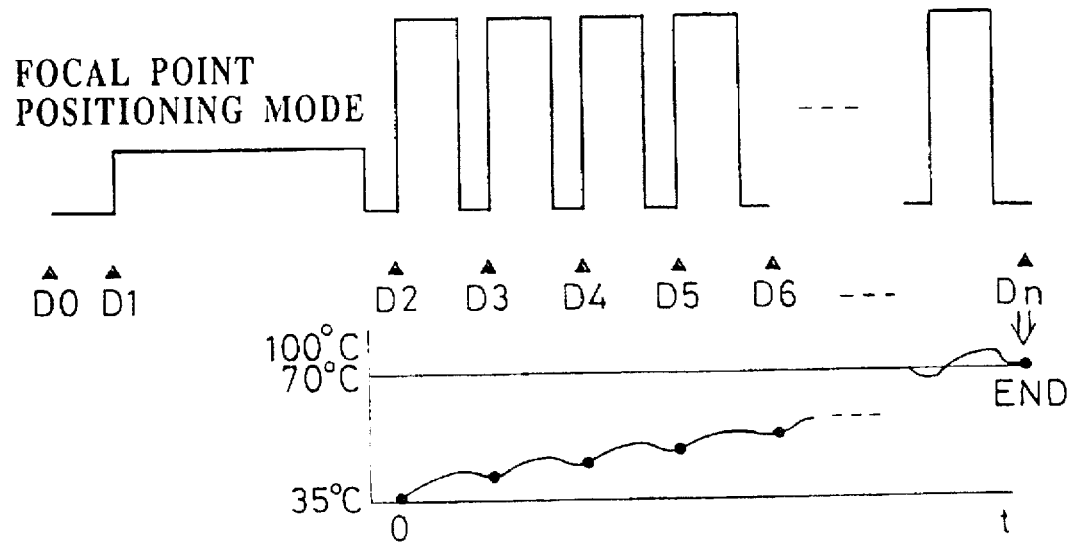
FIGS. 19A and 19B are timing charts for explaining an operation in the fourth embodiment.
Figure 19B:
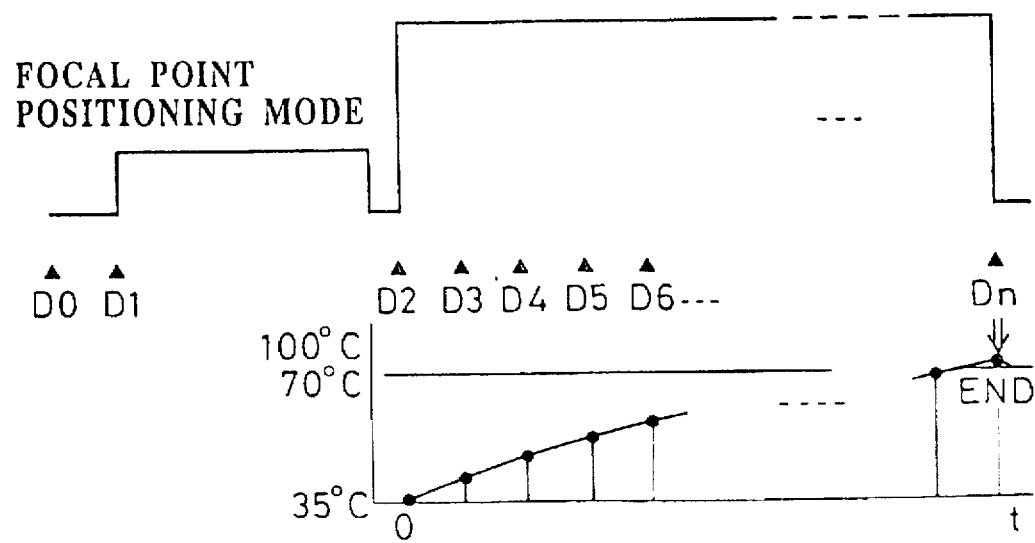

More specifically, the focal point pursuit function is realized according to the sequence shown in FIGS. 19A and 19B. First, FIG. 19A shows a sequence for the short pulse irradiation scheme, in which after the focal point is focused onto the patient according to the focal point positioning mode, the bursty irradiation of the intense ultrasound is started. when one short pulse irradiation is finished and immediately before the next short pulse irradiation starts, the temperature increase distribution data D3 is obtained and stored in the memory 28A. Then, from this data D3, the coordinate of the maximum temperature increase point is calculated. Here, it is also possible to set the center of gravity position of the temperature increase distribution as the focal point coordinate.

Next, this coordinate (indicating the position of the first short pulse application) obtained from the data D3 is subtracted from the first coordinate of the focal point position obtained from the data D2 to calculate the displacement. Then, the control circuit 9A calculates the driving phase of the driving circuits 12 for driving the ultrasound transducer 2, and supplies the phase data to the phase control circuits 11. In response, the driving circuit 12 drives the ultrasound transducer 2 according to the phase data supplied from the phase control circuits 11.

In a similar manner, the temperature increase distribution data D4, D5, etc. are obtained and according to these data, the ultrasound focal point is controlled to be always located at the maximum temperature increase position, such that the focal point can be maintained to be on the treatment portion which is moving because of the respiration motion. As a result, it becomes possible to prevent the failure to obtain the sufficient temperature increase due to the dislocation of the focal point, or the damaging of the not intended portion unintentionally.

In this fourth embodiment, instead of the positioning of the focal point position during the short pulse irradiations, it is also possible to realize the focal point pursuit function during the continuous irradiation as shown FIG. 19B. In this case, the temperature increase distribution data D2, D3, etc. are obtained at prescribed time intervals, and the maximum point of the temperature increase can be measured from these data, such that the focal point is controlled to be always located at the maximum point calculated from these data.

It is to be noted that in the scheme described above, the focal point moving control is carried out discretely, but it becomes possible to carry out the focal point moving control continuously by interpolating between the adjacent data such as D3 and D4 according to the foregoing data such as D2 and D3. It is also possible to realize the focal point pursuit function by predicting and interpolating the focal point moving route to the next point according to three foregoing data.

It is also possible to use the temperature increase distribution measurement of this fourth embodiment in conjunction with the display of the image data, to realize even more accurate treatment.

Also, the NMR parameters utilized for the measurement of the temperature distribution may be replaced by the sonic speed change on the ultrasound image, the temperature change of the tissue CT value on the X-ray CT image, etc.

Figure 20:
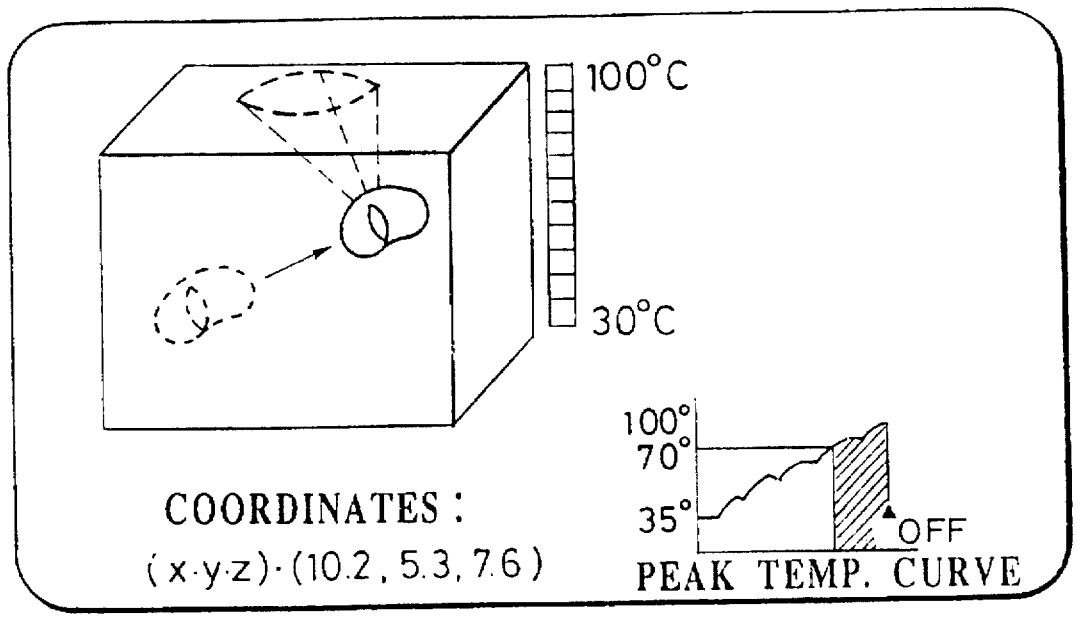
FIG. 20 is an exemplary display used in the apparatus of FIG. 18.
Figure 21:
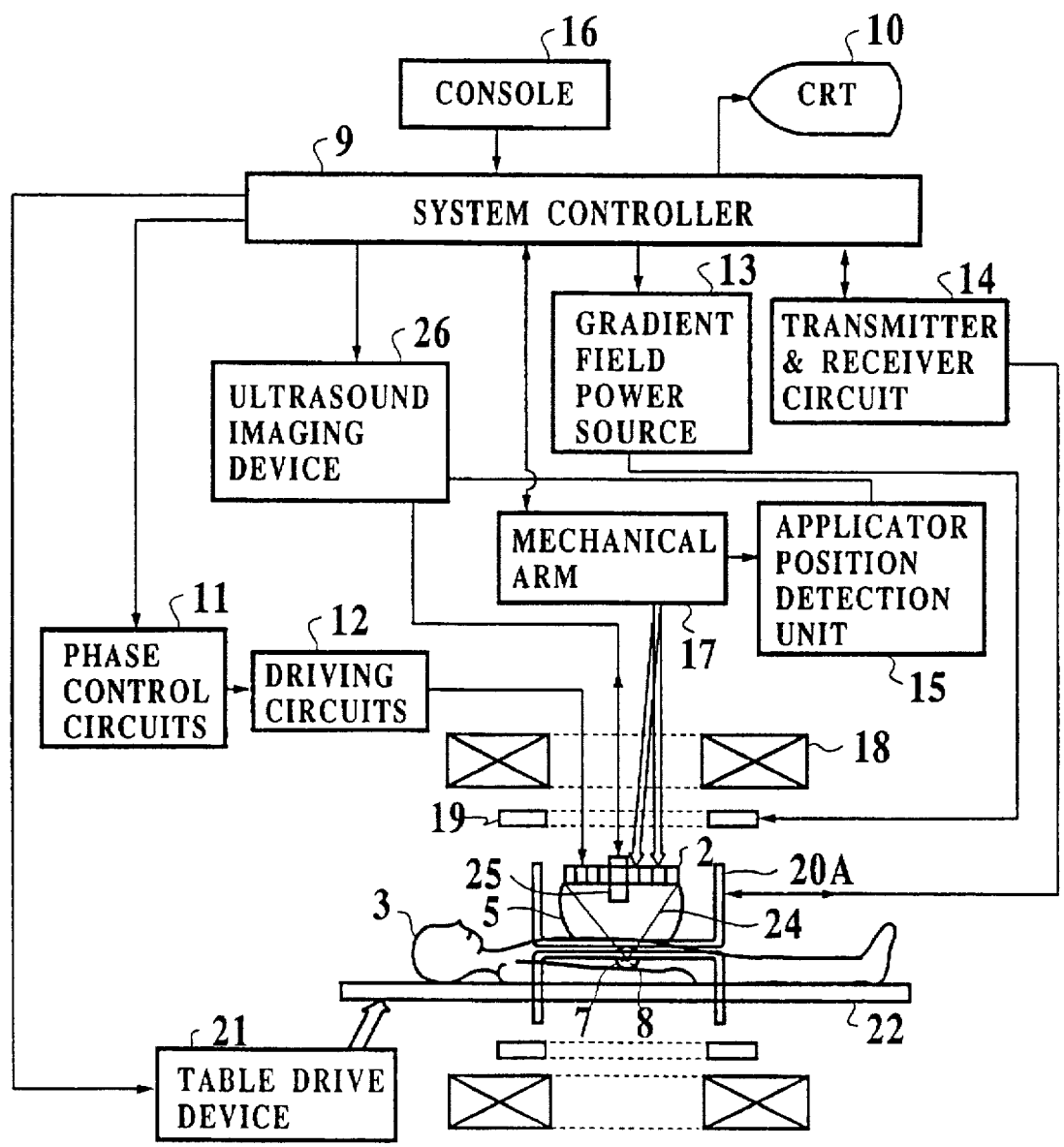
FIG. 21 is a schematic block diagram of a fifth embodiment of an ultrasound medical treatment apparatus according to the present invention.

On the CRT 10, as shown in FIG. 20, the image data and the temperature increase data are displayed together, along with the temperature change of the maximum temperature increase point. Then, when the peak temperature increase reaches to 70° C. for example, the intense ultrasound irradiation is stopped and shifted to the next irradiation point.

It is also possible to calculate the temperature increase distribution by the simulation instead of using the actually measured temperature distribution, which can be displayed along the actual image data.

Next, the fifth embodiment of an ultrasound medical treatment apparatus according to the present invention will be described in detail. Here, those elements which are equivalent to the corresponding elements in the first embodiment of FIGS. 1 and 6 will be given the same reference numerals in the figure and their descriptions will be omitted.

In this fifth embodiment, the saddle type RF coil 20A is used in the MRI part, while the applicator position detection unit 15 is connected with the ultrasound imaging device 26.

Figure 22:
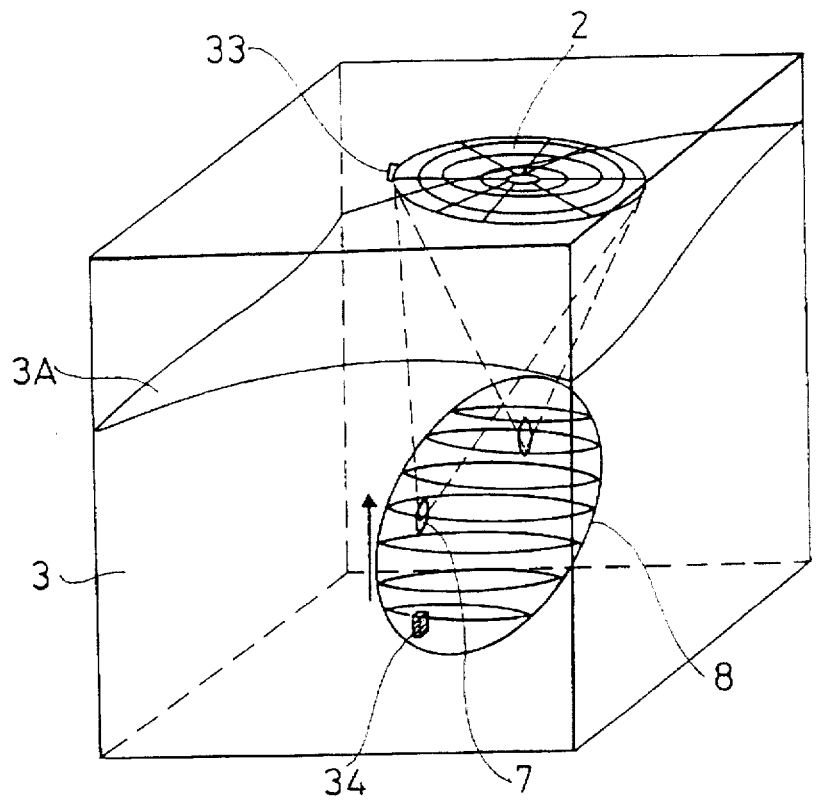
FIG. 22 is an illustration of an exemplary 3D MR image display used in the apparatus of FIG. 21.

Now, in this fifth embodiment, the ultrasound irradiation by the ultrasound applicator can be controlled as shown in FIG. 22. Namely, it has already been confirmed experimentally that the dissipation and the scattering of the ultrasound are larger at the portion which has been thermally degenerated by the ultrasound irradiation compared with the normal tissues. Therefore, when the thermally degenerated portion already exist, it is clinically undesirable to carry out the heating treatment to the tumor located at a position deeper than that of the already existing thermally degenerated portion because:

(1) due to the shielding of the ultrasound by the thermally degenerated portion, the sufficient ultrasound energy cannot reach to the position deeper than that of the thermally degenerated portion; and (2) as the ultrasound dissipation is large at the already existing thermally degenerated portion, the heat generation and the thermal degeneration can be caused at the tissues in front of the already degenerated portion, and there is a danger for the unexpected side effect.

In order to avoid these drawbacks, it is desirable to measure the spatial distribution of the tumor on the image in advance, and start the ultrasound irradiation from the deepest position with respect to the incident direction of the ultrasound, and then proceed to the shallower positions sequentially.

Thus, in FIG. 22, the treatment target 8 is sliced in a direction perpendicular to the central axis of the ultrasound transducer 2, and the treatment is sequentially carried out from the deepest slice along the direction of an arrow toward the body surface 3A, by appropriately controlling the phase control circuits 11 from the system controller 9. As for the order of irradiations within the same slice, it is possible to adopt the scheme disclosed in Japanese Patent Application NO. 4-043603 (1992), in which the irradiation proceeds in an order of the distance between each voxel 34 and the ultrasound transducer 2, so as to suppress the adverse influence of the cavitation.

Figures 23A, 23B:
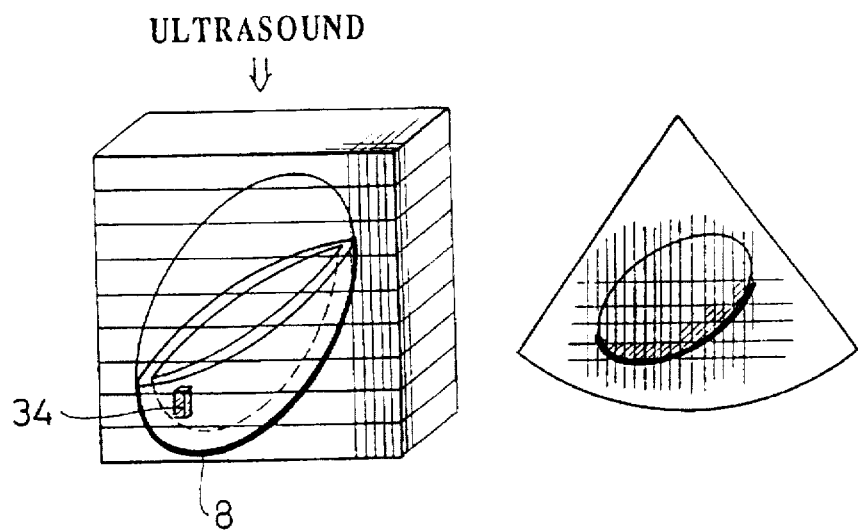
FIGS. 23A and 23B are illustrations of 3D MR image and ultrasound image display in the apparatus of FIG. 21.

Alternatively, in this fifth embodiment, the ultrasound irradiation by the ultrasound applicator can be controlled as shown in FIGS. 23A and 23B, where FIG. 23A shows an MR image while FIG. 23B shows an ultrasound image. In this case, the ultrasound irradiation is carried out for those voxels 34 located on a surface of the tumor but not directly exposed to the ultrasound applicator, in a form of a shell as shown in FIGS. 23A and 23B, in order to realize the safe and accurate treatment. Here, by forming the shell shaped thermally degenerated portion first, it becomes difficult for the ultrasound to reach the normal tissues located at even deeper positions beyond the tumor 8 thereafter such that the undesirable side effect on the normal tissues can be effectively prevented. It is to be noted that this scheme can also be carried out on the 2D image such as that of the ultrasound B mode.

It is also possible in this fifth embodiment to display the focal point position on the 3D image by taking the 3D image in which the ultrasound transducer 2 are included, calculating the geometrical position data of the ultrasound transducer 2 element from the image, and calculating the focal point position from the delays given to each ultrasound transducer element 2 and the geometrical position data. In this case, as shown in FIG. 22, by attaching an applicator reference marker 33 to be a reference point for giving the delays to the ultrasound transducer elements, it becomes possible to judge the the applicator's orientation from the image easily, and the calculation of the focal point position becomes easier. Also in such a case, the applicator position detection unit 15 is unnecessary, and it also suffices for the mechanical arm 17 to simply support the ultrasound applicator, so that the mechanical arm 17 can be operated more freely.

It is also possible to employ the command inputs using the 3D mouse on the virtual 3D space utilizing the virtual reality instead of the command inputs through the console 16 on the displayed 3D image. Moreover, it is also possible to automatically divide the treatment region by extracting the contour of the tumor tissues according to the signal strength difference between the normal tissues and the tumor tissues.

Next, the sixth embodiment of an ultrasound medical treatment apparatus according to the present invention will be described in detail. Here, those elements which are equivalent to the corresponding elements in the first embodiment of FIGS. 1 and 6 will be given the same reference numerals in the figure and their descriptions will be omitted.

Figure 24:
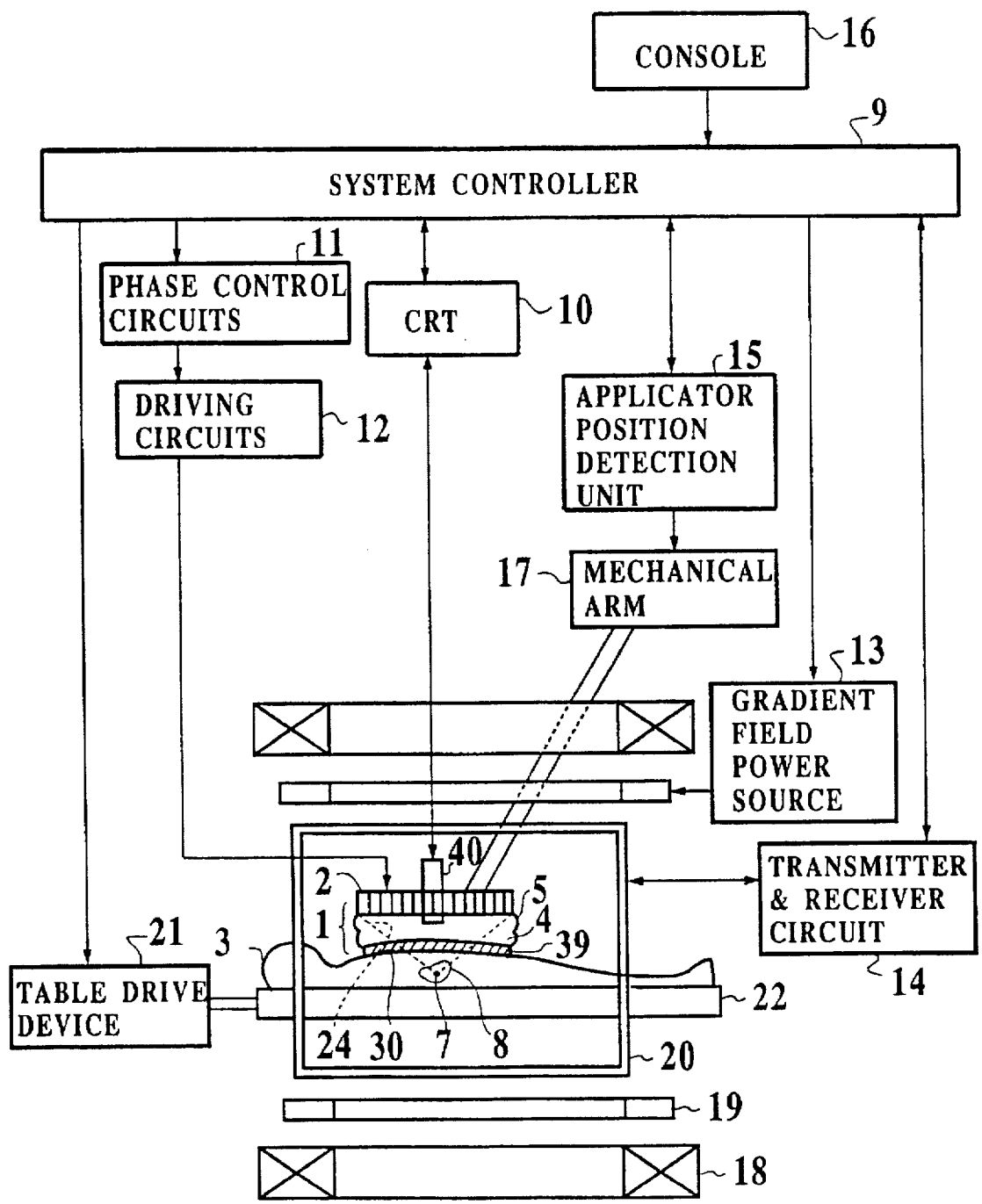
FIG. 24 is a schematic block diagram of a sixth embodiment of an ultrasound medical treatment apparatus according to the present invention.

In this sixth embodiment, as shown in FIG. 24, there is provided an optical camera 40 mounted at a center of the ultrasound transducer 2 and connected with the CRT 10 for taking a real time optical image of the body surface of the patient 3, while the ultrasound applicator 1 is attached on the body surface of the patient 3 through an ultrasound jelly 39 applied between the body surface of the patient 3 and the water bag 5 of the ultrasound applicator 1.

Now, in this sixth embodiment, the abnormal heat generation portion 30 at the coupling section of the body surface of the patient 3 and the ultrasound applicator 1 is detected by means of these ultrasound jelly 39 and the optical camera 40 as follows.

First, the ultrasound jelly 39 is formed from a gel like medium with the acoustic impedance close to that of the living body and crystalline particles made of chemical material having reversible thermochromism. As an example of the material having the reversible thermochromism, an ethylene derivative substituted with condensed aromatic ring such as spiropiran, bianthrone, dixantylene, etc., and it is preferable to use the material among them which shows the color reaction at the temperature of 50° to 60° C. which is lower than that by which the living body can be damaged.

During the heating, when the abnormal heat generation portion 30 is produced on the body surface of the patient 3, the thermochromic particles in the ultrasound jelly 39 are colored in red as their temperature reaches to 60° C. for example. Then, the optical camera 40 monitoring the coupling section between the water bag 5 and the body surface of the patient 3 senses the change of the color of the ultrasound jelly 39.

Then, the real time image obtained by the optical camera 40 is displayed on the CRT 10, and the system controller 9 checks whether there is any picture element showing the red color on the real time image displayed on the CRT 10, and detects a brightness level of the red colored light, in order to detects the occurrence of the abnormal heat generation portion 30. In a case there is a picture element showing the red color, the system controller 9 controls the driving circuits 12 to reduce the intensity of the irradiated ultrasound according to the detected brightness of the red colored light, or stops the ultrasound irradiation.

It is possible to replace the ethylene derivative used above by the other reversible temperature indicative paint materials such as color developing lacquer, vinyl polymer varnish, halides of the mercury or the like and their complex salt and double salt which are pigments showing the discoloration due to the crystalline transition. It is also possible to use the irreversible temperature indicative paint material which is a pigment showing the discoloration due to the dyhydration including complex salts and double salts of Co or Ni such as $CoCl_2.2(CH_2)_6N_4.10H_2O$, $NiBr_2.2(CH_2)_6N_4.10H_2O$. It is also possible to utilize the thermal color reaction used in the heat sensitive paper such as that of the colorless leuco crystal violet or the bisphenol and the like, or the thermal destruction color reaction of the coloring fine particles in the mass chromatography capsule.

Also, instead of mixing these thermochromic materials in the gel like medium, it is also possible to use the film formed by themselves, if such a film can possibly be formed.

In addition, instead of using the thermochromic material, the liquid crystal film having the heat sensitivity may be used.

Figure 25:
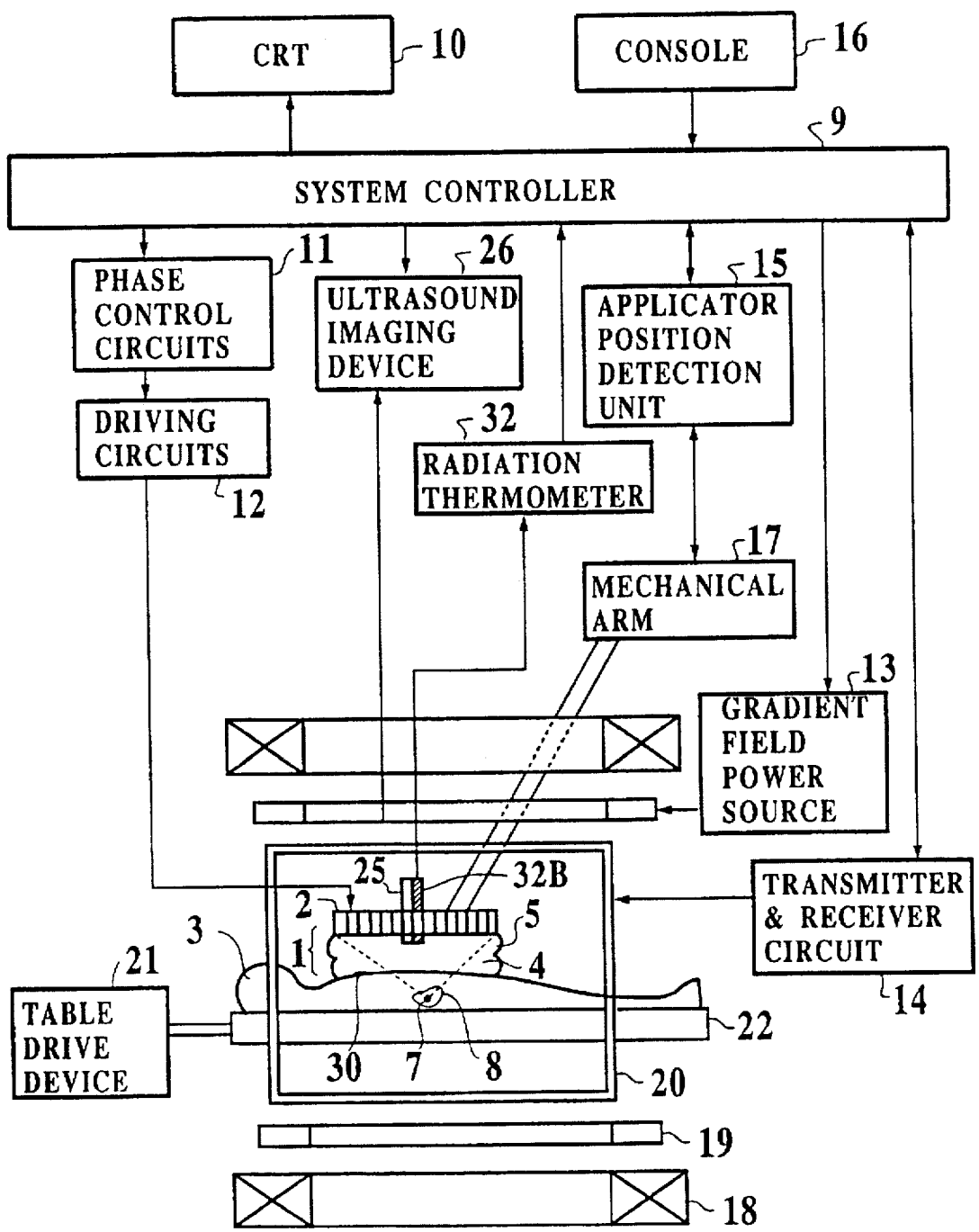
FIG. 25 is a schematic block diagram of a modified configuration for the apparatus of FIG. 24.

Furthermore, it is possible to modify this sixth embodiment into a configuration as shown in FIG. 25, in which the optical camera 40 is replaced by the ultrasound probe 25 connected with the ultrasound imaging device 26, and an emission thermometer 32 with a sensor section 32B, where the ultrasound probe 25 and the sensor section 32B are mounted at a center of the ultrasound transducer 2. In this case, the ultrasound jelly can be of a usual type.

In this modified configuration of FIG. 25, when the emission thermometer 32 indicates a relative temperature increase of over 20° C. with respect to its normal temperature (such as 40° C.), the detected temperature increase is notified to the system controller 9, in response to which the system controller 9 controls the driving circuits 12 to reduce the intensity of the irradiated ultrasound according to the detected temperature increase, or stops the ultrasound irradiation.

It is to be noted that the sixth embodiment described above is not just applicable to the heating treatment of the tumor as described above, but also to the lithotriptic treatment of the calculi using the intense ultrasound as well. In a case of the lithotriptic treatment, however, the occurrence of the high pressure portion on the body surface of the patient is more serious problem than the occurrence of the heat generation portion, so that the pressure sensitive color reaction of the ultrasound jelly can be monitored by the optical camera 40.

Next, the seventh embodiment of an ultrasound medical treatment apparatus according to the present invention will be described in detail.

In this seventh embodiment, the configuration of the apparatus is essentially similar to that of the first embodiment described above, so that its description will not be repeated here.

This seventh embodiment concerns with the treatment incorporating the simulation.

Figure 26A:
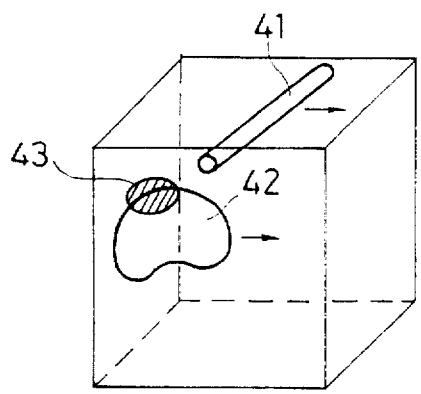
FIGS. 26A, 26B, and 26C are illustrations of 3D MR images of a treatment region used in a seventh embodiment of an ultrasound medical treatment apparatus according to the present invention.
Figure 26B:
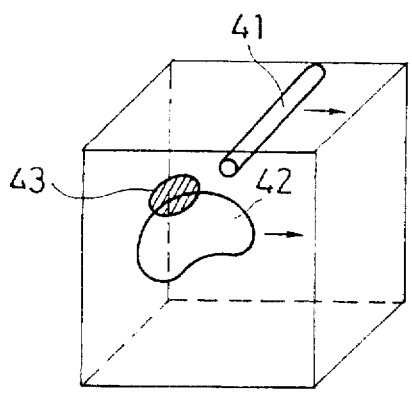
Figure 26C:
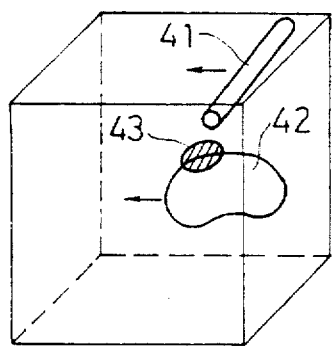

First, as the preliminary examination, the positions and the states of the treatment target tumor and its surrounding are examined. For example, as shown in FIGS. 26A, 26B, and 26C, the size, shape, and property of the treatment target 43, and the time change of the state of its surrounding such as the other organ 42, bone 41, blood vessel, nerve, etc. are 3D imaged at high speed by the MRI part (or other imaging device such as an X-ray CT), and each tissue is distinguished and extracted, while the obtained images are stored in the memory. In particular, as for the periodic motion such as the respiration motion, the images are obtained for over one period. At this point, the spatial resolution is required to be capable of distinguishing the tumor from the other tissues at least, and the temporal resolution is required to have a sufficient minuteness such as less than one second with respect to the respiration period.

Next, the data on the physical characteristics such as the temperature increase characteristic, the acoustic impedance, etc. of each tissue such as organ, bone, etc. are entered from the console 16 on the MR images, so as to produce a 3D dummy living body model including the time change. In displaying this model, each tissue can be displayed independently, or in superposition, which can be selected from the console 16. The CRT 10 can provide the 2D screen display obtained by projecting 3D data, and tis orientation and size can be freely setup from the console 16. Instead, it is also possible to use the 3D display using the holography or the space scan type 3D display.

Figure 27:
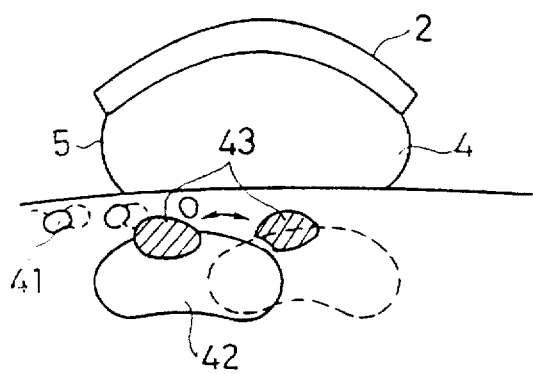
FIGS. 27 and 28 are illustrations of exemplary cases of the ultrasound irradiation route that can be used in the seventh embodiment.

Next, the attaching position of the water bag 5 containing the coupling fluid 4 is determined. For example, when the treatment target 43 is periodically moving because of the respiration as indicated in FIG. 27, the position from which the ultrasound can be irradiated with the least obstacles such as the bone 41 and organ 42 to the treatment target 43 at each phase of the periodic motion is searched in the image.

Then, in this state, the treatable region is calculated. Then, the refraction and reflection due to the differences in the acoustic impedance among the tissues are calculated, and the irradiation route of the ultrasound from the ultrasound applicator with respect to each position in the tumor region are simulated.

Here, the driving conditions of the ultrasound transducer 2 are determined such that, when the obstacles such as bones, cavity organs, or lung field for the ultrasound exist on the route, the transducer element generating the ultrasound which collides the obstacles is stopped being driven so as to avoid the unnecessary heating at the reflection surface, while the other transducer elements are driven to apply the required energy at the focal point region by controlling the driving power appropriately.

Figure 28:
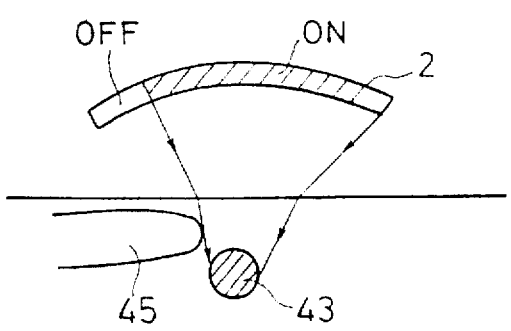

For example, as shown in FIG. 28, when an obstacle 45 exists between the treatment target 43 and the ultrasound transducer 2, the route is calculated as indicated by the arrows in FIG. 28, and the part of the ultrasound transducer 2 with the shading in FIG. 28 is driven while the remaining part is not driven so as to avoid the irradiation onto the obstacle 45. Here, there is a limit to the power source for providing the driving power for the ultrasound transducer 2, and the high power region for the focal point shifted by the phase control is limited to a certain range around the geometrical focal point of the ultrasound transducer 2, so that the treatable region can be limited by these setting of the driving conditions for the ultrasound transducer 2.

Next, at a time of the treatment, from the obtained 3D static image the operator determines the treatment protocol such as a treatment region and a treatment order. At this point, the requirement from the system such as that the treatment must be carried in an order of the distances from the ultrasound applicator 1 is also taken into account.

Then, according to this treatment protocol, the treatment is carried out while sequentially moving the focal point. The phase of the respiration motion from the image obtained before the treatment which corresponds to the positional relationship of the treatment target and its surrounding at that point is judged, and the ultrasound irradiation according to the irradiation condition for this phase is carried out.

Alternatively, the respiration monitor can be used and the correspondence between the image and the respiration monitor output is established in advance, such that the phase of the respiration can be judged from the observation of the respiration monitor output at a time of the treatment.

Here, by using such a dummy living body model, it becomes possible to simulate the displacement of the dummy focal point set by the phase control due to the refraction and reflection between the tissues. In a case the displacement is large, the phases of the phase control circuits 11 are fine controlled to set the actual focal point in agreement with the setting focal point. Also, in a case the lowering of the focal point pressure is occurring due to the displacement, the driving power from the power source is controlled to achieve the sufficient treatment effect.

In the above, the irradiation route has been evaluated from the applicator side by the simulation, bur the optimum irradiation conditions for each focal point may be sequentially determined according to the treatment order (setting of the focal point positions) set up in advance. In this case, the series of the treatment operations can be sequentially simulated in time order, so that the treatment can be virtually executed by providing the animation display, and the re-confirmation of the safety of the treatment procedure and the prediction of the treatment effect become possible, so that the flow of the treatment can be comprehended at a glance, and showing of this to the patient may be helpful in a case of obtaining the informed consent from the patient.

As for a specific procedure, in short, the treatment order is determined, and for each focal point set up, the irradiation conditions at each phase of the respiration is determined as described above by calculating the irradiation route. Then, the optimum phase at which a maximum number of ultrasound transducer elements can be utilized or a minimum number of obstacles and regions dangerous to irradiate are contained is determined among the determined irradiation conditions. This procedure is carried out for each focal point, and at a time of the treatment, the focal points are set up in the determined order, and the ultrasound irradiation is carried out at the determined optimum phase.

Figure 29:
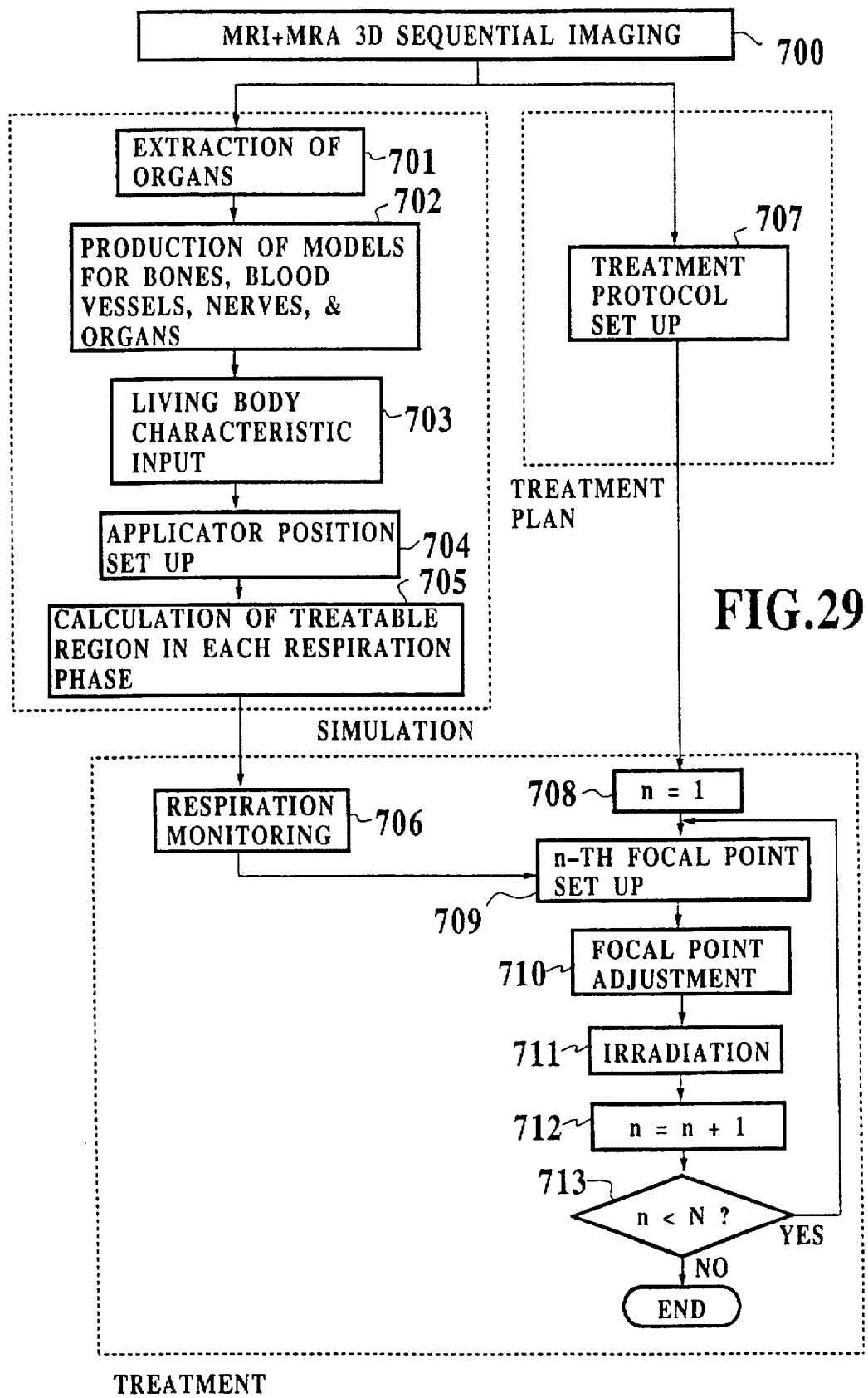
FIG. 29 is a flow chart for one operation of the seventh embodiment.
Figure 30:
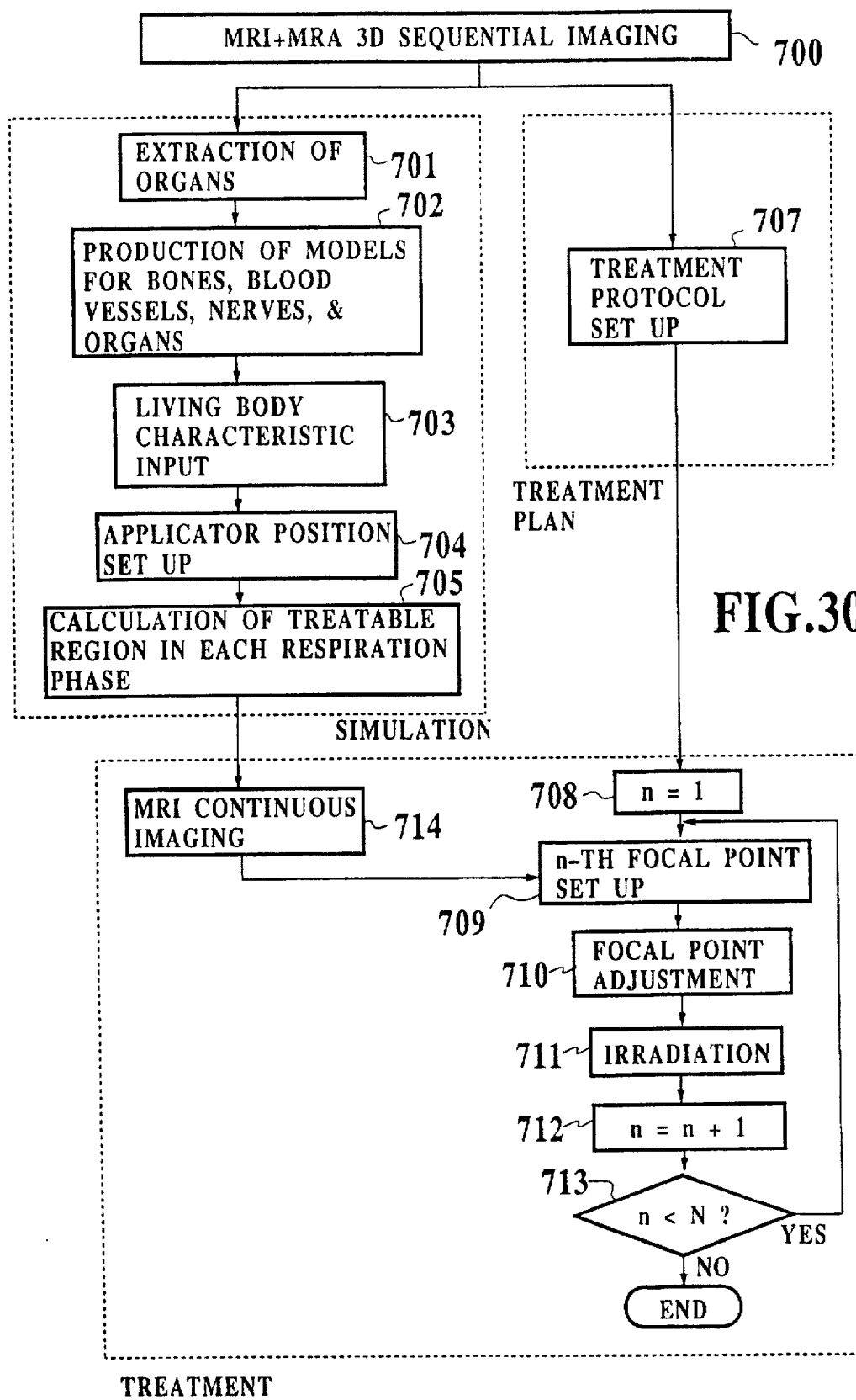
FIG. 30 is a flow chart for another operation of the seventh embodiment.

More specifically, the operation in this seventh embodiment is carried out according to the flow chart of either FIG. 29 or FIG. 30, where FIG. 29 corresponds to a case of using the respiration monitor, while FIG. 30 corresponds to a case of using the MR image for the phase detection.

First, in a case of FIG. 29, the operation proceeds as follows.

First, at the step 700, a number of 3D sequential MR images are taken by using the MRI and the MRA (Magnetic Resonance Angiography), etc. The obtained images are then entered into the simulation processing and the treatment plan processing.

In the simulation processing, the organs and tissues are extracted from the obtained images at the step 701. Then, according to these, the models for the bones, blood vessels, nerves, organs are produced at the step 702, and the living body characteristics for these models are entered at the step 703. Then, the applicator position is determined at the step 704, and the treatable region for each phase of the respiration is calculated at the step 705. The obtained results are then outputted to the respiration monitoring at the step 706 of the treatment processing.

On the other hand, in the treatment plan processing, the treatment protocol is determined by setting N focal points at the step 707.

Then, in the treatment processing, a current focal point number n is set to 1 initially at the step 708. Meanwhile, the phases of the respiration are detected by the respiration monitoring at the step 706, and the n-th focal point is set up while observing the simulation image at the step 709. Next, the focal point is adjusted in agreement with the n-th setting focal point at the step 710. Then, the ultrasound is irradiated to this focal point at the step 711. Next, the current focal point number n is incremented at the step 712, and whether the incremented is less than the total number N of the setting focal points or not is determined at the step 713. If so the operation returns to the step 709, whereas otherwise the operation is ended, so as to carry out the operation for all of the N setting focal points.

In contrast, in a case of FIG. 30, the operation differs from that of FIG. 29 described above in that the respiration monitoring of the step 706 in FIG. 29 is replaced by the MRI continuous imaging for the purpose of the phase detection at the step 714 in this FIG. 30.

Also, after the entire treatment procedure is determined, the treatment is virtually executed according to the treatment order, to synthesize a treatment effect (degenerated region). Then, it is possible to check the undesirable presence of treatment overlook, erroneous irradiation, unnecessary heating, etc.

Here, one irradiation time for the treatment energy is set to be sufficiently short with respect to the respiration period, but in a case of setting the irradiation time to be longer by lowering the irradiation power, the irradiation can be done efficiently by irradiating the same point during the irradiation with respect to the setting focal point within the tumor, so that the driving phases are set to be controlled to move the focal point in accordance with the respiration motion, according to the time change images of the dummy living body model. At this point, the irradiation route is also set up to avoid the obstacles as described above.

Up to this point, the obstacles are those which can be detected by the preliminary examination, but at a time of the actual treatment, there can also be an obstacle such as an intestinal tract gas which appear suddenly during the treatment. With respect to such an unexpected obstacle, the image can be taken before the treatment starts, or immediately before the irradiation starts, and the irradiation route can be set up again to avoid such an unexpected obstacle.

In a case of obtaining the images again before the treatment, either the simulation is carried out once again by using the obtained images, or the changed parts alone are added to the already carried out simulation.

During the actual treatment, in a case on obtaining the images immediately before the irradiation, the dummy living body model is re-constructed according to the obtained images, and the planned irradiation route is re-calculated. Then, the displacement from the focal point set up in the simulation carried out in advance is corrected, and the ultrasound transducer elements are selected again to avoid irradiating onto the obstacles such as the intestinal tract gas contained within the new irradiation route.

In order to carry out such a correction, there is a need to make correspondences between the 3D images of the dummy living body model obtained at a time of the simulation prior to the treatment and the images obtained immediately before the treatment.

To this end, before the treatment starts, the images can be obtained, and the position and posture of the patient, the position and angle of the applicator, etc. are adjusted such that the obtained image can be matched with the images of the simulation. By fixing the patient at the best matching state, the further displacement from that state can be reduced.

Even then, there is a possibility for some displacement to be caused by the body movement, etc. during the treatment, so that the images obtained during the treatment and the simulation images for the corresponding respiration phase are constantly compared to calculate the differences, and when the sum of these differences exceeds a prescribed value, the treatment is stopped, the coordinate transformation is carried out on the simulation images to make the displacement minimum, and the irradiation route is calculated again from the position of the applicator after the transformation. Alternatively, the positions of the patient and the applicator can be adjusted again at this point.

In order to make such a position adjustment for the patient, the position and the angle of the treatment table are made to be adjustable externally, such that the time required for moving the patient out of the gantry for the purpose of the adjustment as well as the further displacement that can be caused by the moving of the patient can be reduced.

Figure 31:
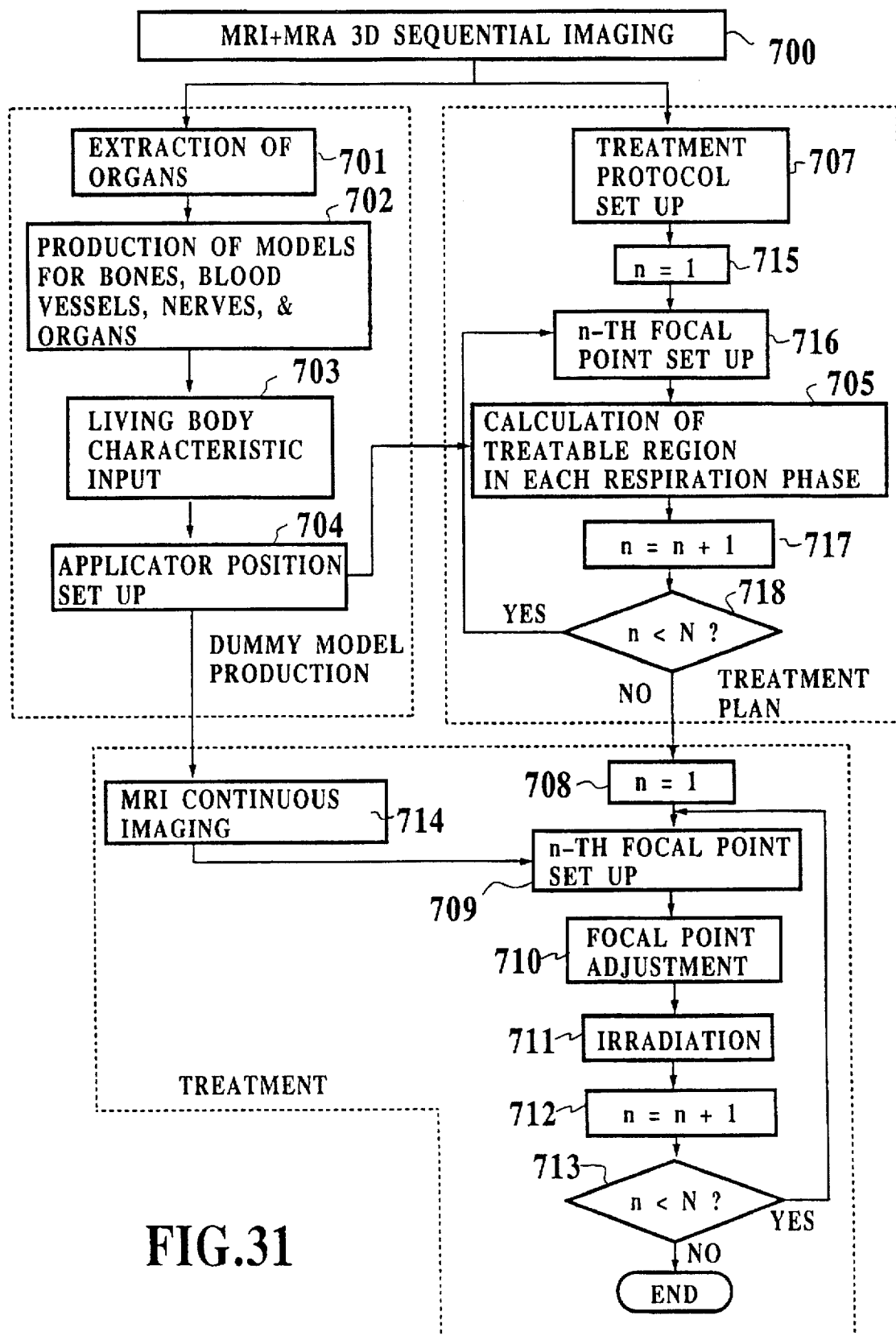
FIG. 31 is a flow chart for still another operation of the seventh embodiment.

More specifically, the above described procedure can be carried out according to the flow chart of FIG. 31 as follows. Here, those steps which are equivalents to the corresponding steps in the flow charts of FIGS. 29 and 30 are given the same reference numerals and their descriptions will be omitted.

Here, the dummy model production processing differs from the simulation processing of FIGS. 29 and 30 in that the calculation of the treatable region at the step 705 is not included. Thus, the applicator position determined at the step 704 is outputted to the treatment plan processing and the treatment processing. The determined applicator position is utilized at the treatment plan processing in order to adjust the positions of the patient and the applicator or to stop the treatment if the displacement of the patient occurs during the treatment.

On the other hand, in the treatment plan processing, after the step 707 for determining the treatment protocol, a current focal point number n is set to 1 initially at the step 715, and the n-th focal point is set up at the step 716. Next, the step 705 similar to that in FIGS. 29 and 30 is carried out for calculating the treatable region for each phase of the respiration in order to determine the driving voltage, the transducer element selection, etc. according to the applicator position entered from the step 704. Next, the current focal point number n is incremented at the step 712, and whether the incremented is less than the total number N of the setting focal points or not is determined at the step 717. If so the operation returns to the step 716, whereas otherwise the operation proceeds to the treatment processing which is essentially the same as that in FIG. 30.

Here, the dummy living body model is obtained by the computer graphics, but a physical model may be actually constructed by using materials having similar physical characteristics as the living tissues.

It is to be noted that the seventh embodiment described above is not just applicable to the heating treatment of the tumor as described above, but also to the lithotriptic treatment of the calculi using the intense ultrasound as well. For example, the lung field is often contained in the irradiation route, so that the unnecessary heating at the lung field can be prevented by selecting the ultrasound transducer elements to avoid the lung field.

Also, it is not necessary to use the imaging device of the gantry type such as the MRI as described above, or the X-ray CT, and the ultrasound probe in a form of the body cavity probe may be used either singly or in combination. It is also possible to the usual X-ray image rather than the CT image. In such a case, it is impossible to image behind the obstacles such as bones contained in the X-ray route. Thus, by simulating the route as in the above, the influence of the obstacles can be avoided effectively.

Next, the eighth embodiment of an ultrasound medical treatment apparatus according to the present invention will be described in detail.

In this eighth embodiment, the configuration of the apparatus is essentially similar to that of the first embodiment described above, so that its description will not be repeated here.

In this eighth embodiment, however, the MRI part also carries out the MRA to obtain the images of the blood vessels. Here, any known imaging scheme such as Time of Flight, Phase Contrast, and MTC can be used for the MRA.

First, in order to set up the treatment plan, the MR images and the MRA images are obtained for the same imaging region, and the treatment target is extracted from the obtained MR images, while the images of the blood vessels contained within the treatment target are also obtained.

Figure 32:
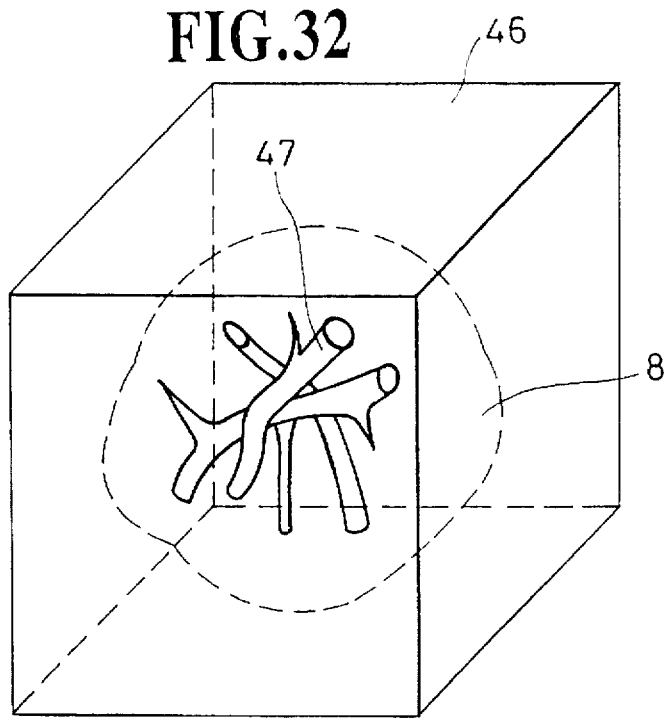
FIG. 32 is an illustration of 3D MR image of a treatment region used in an eighth embodiment of an ultrasound medical treatment apparatus.

Then, as shown in FIG. 32 for example, the 3D imaging region 46 containing the treatment target 8 and the blood vessels 47 in superposition is displayed.

Figure 33:
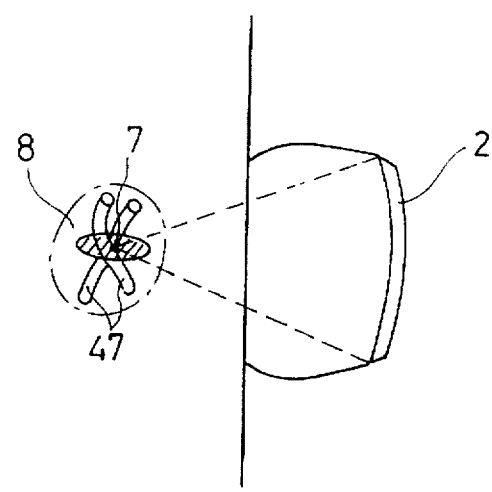
FIG. 33 is an illustration of a positioning of a focal point in the treatment region of FIG. 32.
Figure 34:
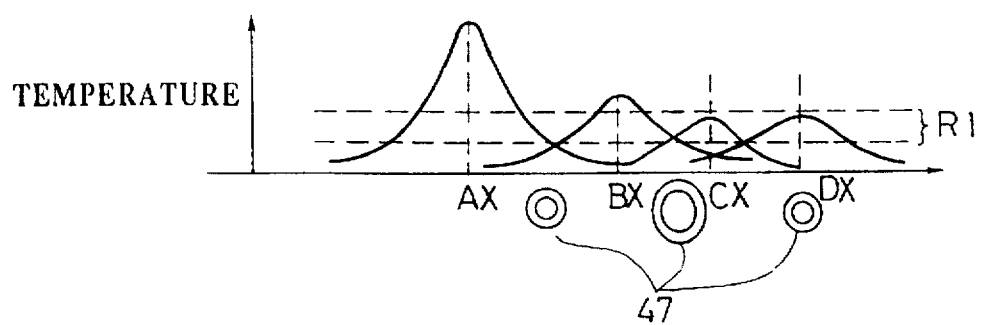
FIG. 34 is a temperature distribution graph for explaining an operation in the eighth embodiment.

Then, as shown in FIG. 33, the focal point 7 of the ultrasound for treatment is set up to carry out the treatment throughout the treatment target 8, and for each setting focal point, when the treatment region (shaded region in FIG. 33) overlaps with the blood vessels, the irradiation power is reduced so as not to cause any damage to the blood vessels, and the irradiation to cause the fibration is carried out for the tumor tissues around the blood vessels. For example, as shown in FIG. 34, when the irradiation positions AX, BX, CX, and DX are set up, the irradiation power is raised for the positions such as the position AX which are located away from the blood vessels 47 in order to raise the treatment effect at the non-blood vessel portion, whereas the irradiation is made to cause the fibration for the positions such as the positions CX and DX which are in a vicinity of the blood vessels 47 and therefore heated only in the fibration range R1. Then, the irradiation power at each focal point is adjusted to make the sufficient treatment more than just the fibration as a whole, while preventing the damaging of the blood vessels.

As a specific treatment procedure, first at a time of determining the irradiation conditions, the temperature distribution is theoretically calculated according to the irradiation conditions, or the experimentally obtained temperature distributions corresponding to the irradiation conditions are stored in the memory and the appropriate temperature distribution is called up in accordance with the irradiation conditions, to obtain the temperature of the blood vessel tissues in a vicinity of the focal point, and the irradiation conditions are determined to raise the irradiation power within a range of not damaging the blood vessels. Then, the irradiation conditions for each focal point are determined in order to treat all the tumor tissues. At this point, it is also possible to optimize the focal point position and the irradiation power such that the excessive power is not going to be applied to the blood vessels.

Then, according to the treatment plan set up in such a manner, the actual treatment is carried out. During the treatment, it is also possible to carry out the non-invasive body temperature distribution measurement based on the temperature dependency of the parameters for the diffusion and the proton chemical shift, in real time by the MRI part, to measure the temperature distribution during the heating. Then, the excessive heating of the blood vessels can be monitored according to this measurement, so as to prevent the damaging of the blood vessels.

More specifically, the operation described above can be carried out according to the flow chart of FIG. 35 as follows.

First, the MR image in a vicinity of the treatment target is obtained at the step 900. Then, the tumor is extracted from the obtained MR image at the step 901, and the blood vessels within the tumor are extracted from the MRA image at the step 902. Next, the irradiation position is set up according to the extracted tumor and the blood vessels at the step 903, and whether the set up of the treatment plan is completed or not is determined at the step 904. When it is not completed yet, whether any blood vessel is contained within the treatment region or not is determined at the step 905. If so, the irradiation time is made longer while the irradiation power level is lowered at the step 906. If not, the irradiation time is shortened while the irradiation power level is raised at the step 907. Then, the operation returns to the step 903 for the next irradiation position.

When the set up of the treatment plan is completed at the step 904, the irradiation position is set up at the step 908, and the ultrasound irradiation is carried out at the step 909, while making the real time temperature distribution measurement.

Also, in a case of utilizing the temperature measurement by the MRI part, without setting up the detailed treatment plan up to the irradiation conditions, the irradiation position can be set up to the tumor portion and the irradiation can be started, while making the real time temperature measurement. Then, the irradiation power is gradually raised within a range of not raising the temperature of the blood vessels beyond the prescribed threshold, and the irradiation for that irradiation position is finished when the temperature reaches to the threshold. Then, the focal point is shifted to the next irradiation position, and the similar operation is repeated for the next irradiation position.

More specifically, this alternative operation described above can be carried out according to the flow chart of FIG. 36 as follows. Here, those steps which are equivalents to the corresponding steps in the flow charts of FIG. 35 are given the same reference numerals and their descriptions will be omitted.

Figure 35:
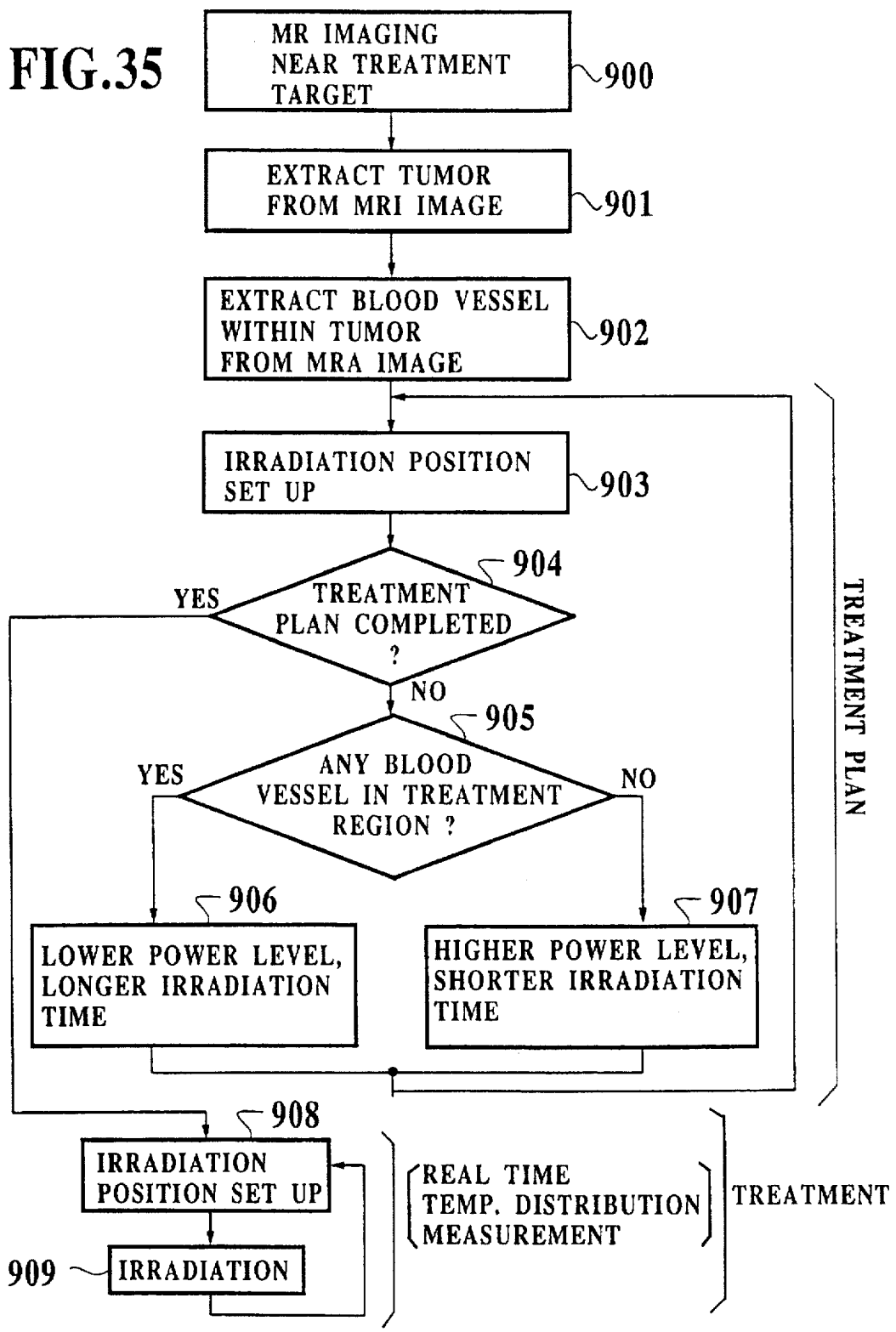
FIG. 35 is a flow chart for one operation of the eighth embodiment.
Figure 36:
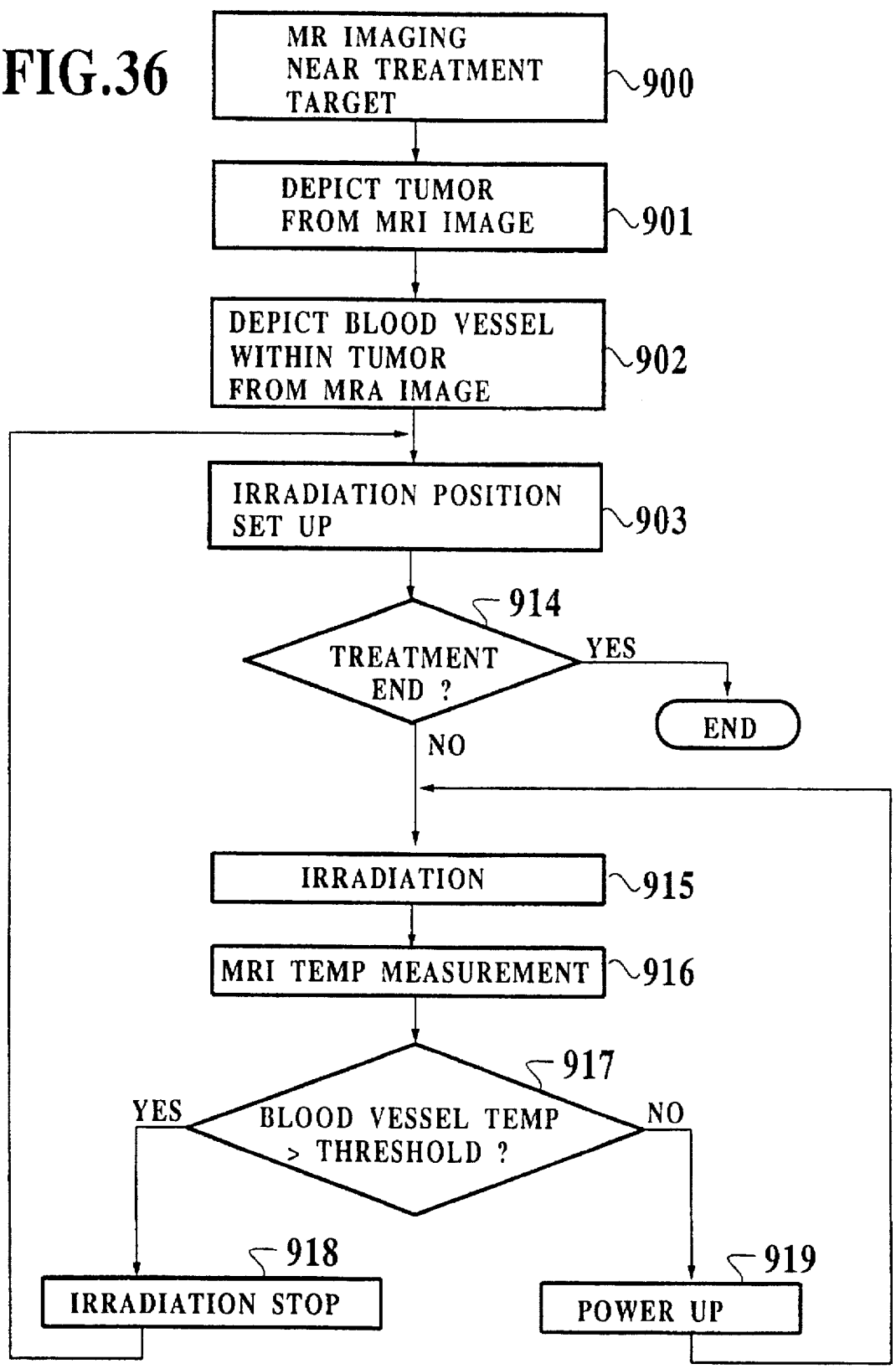
FIG. 36 is a flow chart for another operation of the eighth embodiment.

In this case, the steps 900 to 903 are identical to those in FIG. 35. Then, at the step 914, whether the treatment going to be ended or not is determined. If so, the operation is terminated, whereas otherwise, the ultrasound irradiation is carried out at the step 915, and the temperature measurement by the MRI part is carried out at the step 916. Then, whether the temperature of the blood vessels is greater than the prescribed threshold or not is determined. If so, the irradiation is stopped at the step 918 and the operation returns to the step 903, whereas otherwise the irradiation power is raised at the step 919 and the operation returns to the step 915.

In particular, for the thick major blood vessel, it is possible to set up the treatment plan such that the irradiation to such a major blood vessel is avoided.

In the actual treatment, the usual MR images are obtained continuously, while the relative positional relationship between the images of the blood vessels by the MRA and the MR images is obtained at a time of the treatment plan set up, such that the images of the blood vessels can be superposed onto the continuously obtained usual MR images, so as to correct the position displacement due to the motion. Here, if the MRA can be carried out in real time also, the it becomes possible to irradiate the treatment energy while confirming the blood vessels in the treatment region sequentially before the actual irradiation.

Also, by obtaining the image of the perfusion by using the Gd-DTPA, it is also possible to obtain the images of the blood flows through the capillary blood vessels as well, so that the irradiation power can be controlled to be lower at portion at which the capillary blood vessels are conglomerated, in order to avoid the excessive loss of blood.

Even in the conventional tumor treatment, there has been a treatment method to kill the tumor portion by cutting the nutrition supply to the tumor portion by plugging the nutrition blood vessel. In analogy, for the purpose of preventing the excessive loss of blood, the nutrition blood vessel to the tumor portion can be plugged before the treatment, so as to carry out the heating treatment while preventing the loss of blood, the safety of the treatment can be raised even higher.

It is to be noted that instead of the MRA used above, the blood vessel imaging can be realized by the X-ray angiography or the ultrasound imaging as long as the positions of the blood vessels can be comprehended three dimensionally. Also, as the imaging diagnostic device to be used for the treatment plan set up and the monitoring, instead of the MRI used above, the X-ray CT, the ultrasound imaging, or their combination with the MRI can be used as desired. Also, the treatment means can be provided by any device capable of supplying the concentrated energy to the treatment portion within the living body, and the laser heating treatment device using the optical fiber to be inserted into the tissues, or the microwave heating treatment device may be used instead of the ultrasound treatment described above.

Next, the ninth embodiment of an ultrasound medical treatment apparatus according to the present invention will be described in detail.

Figure 37:
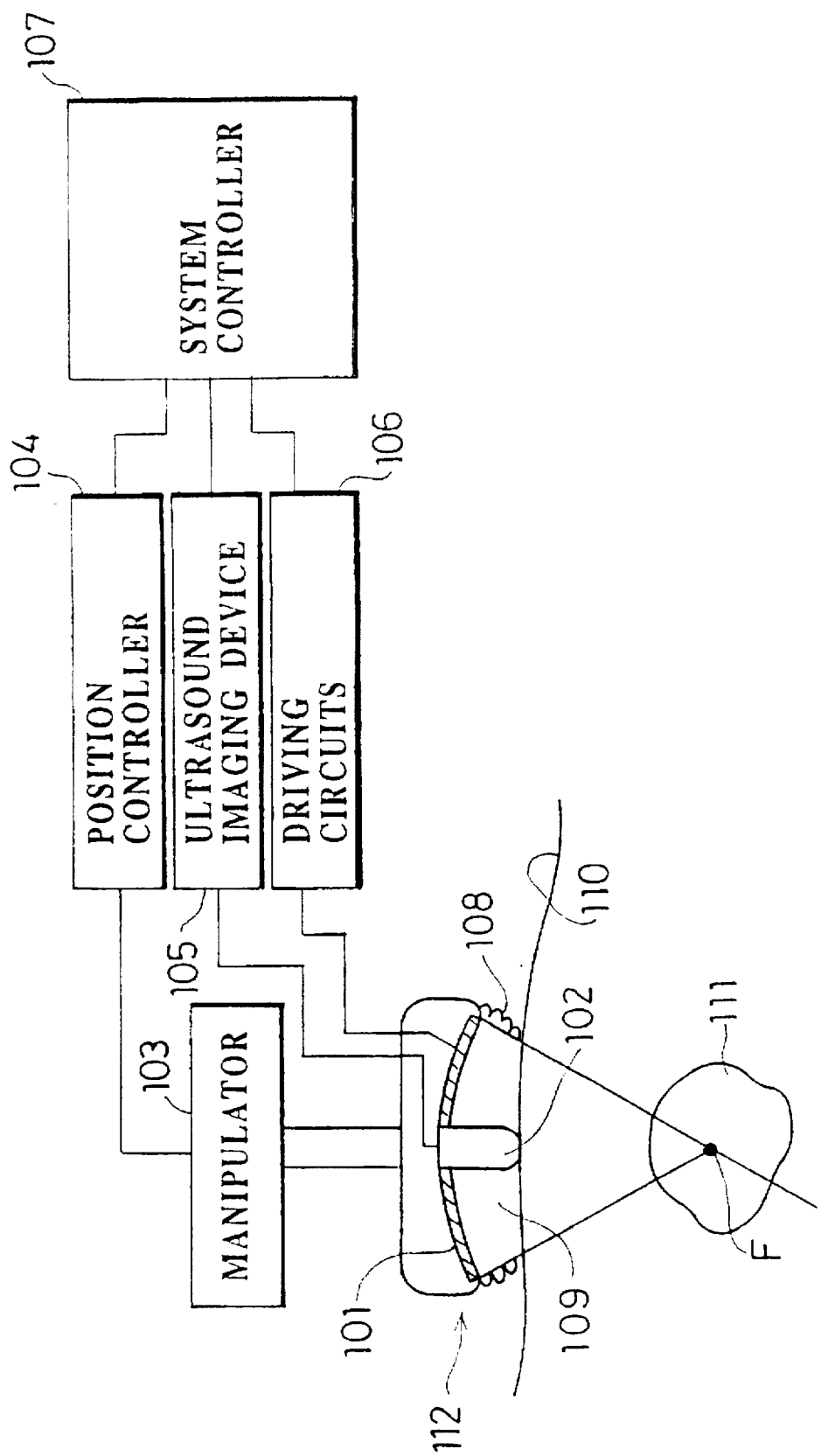
FIG. 37 is a schematic block diagram of a ninth embodiment of an ultrasound medical treatment apparatus according to the present invention.

As shown in FIG. 37, in this ninth embodiment, the ultrasound medical treatment apparatus includes an ultrasound applicator 112 which comprises an ultrasound transducer 101 for irradiating intense ultrasound for treatment, a water bag 108 for containing a coupling fluid 109 for leading the intense ultrasound from the ultrasound transducer 101 to a patient 110, and an ultrasound probe 102 mounted at a center of the ultrasound transducer 101.

Here, the ultrasound transducer 101 is formed by a concaved disk shaped piezoelectric member for generating ultrasound focused, which is connected to driving circuits 106 for driving the ultrasound transducer 101 to irradiate the intense ultrasound at a time of the treatment in order to treat the treatment target located at a focal point F by heating the treatment target 111 such as a tumor at a high temperature of 70° to 90° C.

The ultrasound probe 102 is connected with an ultrasound imaging device 105 for imaging the tomographic image of the interior of the patient 110, which is utilized in positioning of the focal point F with respect to the treatment target 110 and in monitoring the treatment state.

The ultrasound applicator 112 also includes a manipulator 103 for manipulating the ultrasound transducer 101 in order to position the focal point F with respect to the treatment target 111, a position controller 104 connected to the manipulator 103 for controlling the operation of the manipulator 103, and a system controller 107 for controlling the overall operations of the position controller 104, the ultrasound imaging device 105, and the driving circuits 106.

The ultrasound probe 102 transmits the ultrasound pulses and receives the reflected pulses from the structures inside the living body to obtain the display of the tomographic image on the ultrasound imaging device 105. When the ultrasound for treatment generated from the ultrasound transducer 101 is reflected by the structures inside the living body, the ultrasound probe 102 receives the reflected ultrasound as noises for disturbing the ultrasound tomographic image. In some cases, the display of the ultrasound tomographic image during the application of the ultrasound by the ultrasound transducer 102 can be altogether impossible.

Figure 38:
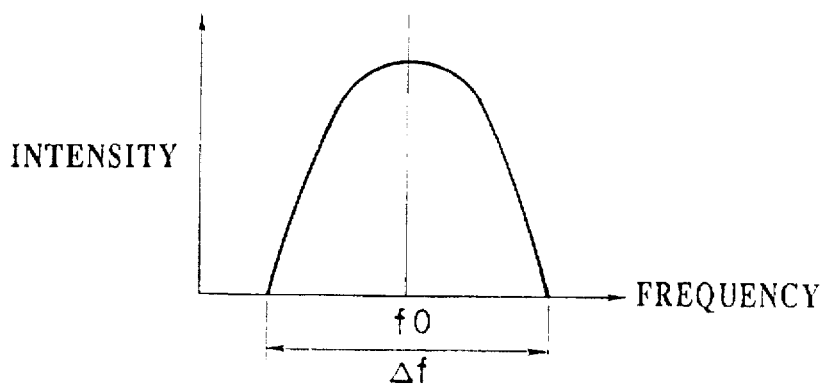
FIG. 38 is a graph showing a frequency characteristic of ultrasound pulse for imaging used in the apparatus of FIG. 37.

This ultrasound probe 102 has a frequency characteristic as shown in FIG. 38. Here, the ratio of the frequency bandwidth Δf and its central frequency f0 depends on the detailed configuration of the ultrasound probe 102, but usually in a range of about 100 to 150%. Assuming that it is 100%, the sensitive frequencies are in a range of about 0.5×f0 to 1.5×f0. Thus, if it can be set up to be such that the frequency components of the reflected ultrasound resulting from the ultrasound irradiation for treatment is not contained within the frequency bandwidth of this ultrasound probe 102, the introduction of the noises into the ultrasound tomographic image can be prevented.

Figure 39:
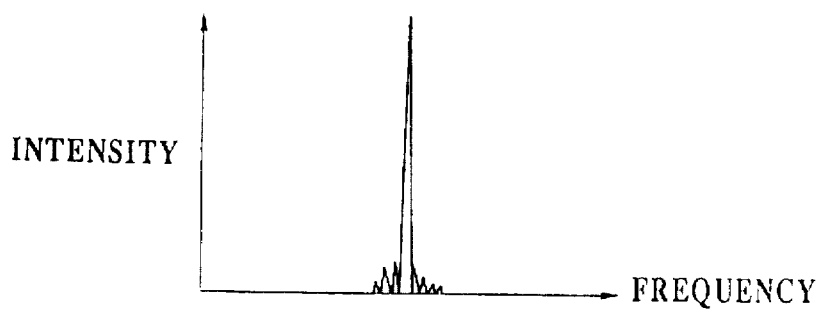
FIG. 39 is a graph showing a frequency characteristic of ultrasound for treatment used in the apparatus of FIG. 37.

On the other hand, the ultrasound transducer 101 is driven to generate the bursty ultrasound for treatment at the frequency of about 1 MHz for about one second, so that the generated ultrasound has a frequency characteristic with a narrow bandwidth as shown in FIG. 39. Thus, by setting the frequency of the ultrasound for treatment to be below ½ of the central frequency of the ultrasound probe 102, the major frequency components of the ultrasound for treatment can be outside of the sensitive frequency bandwidth of the ultrasound probe 102, such that the ultrasound tomographic image without an influence of the noises can be obtained.

However, the ultrasound probe 102 is not totally insensitive for the frequencies outside of the sensitive frequency bandwidth, while the ultrasound for treatment also contains some spread in the frequencies albeit at a low level. Here, as the ultrasound transducer 101 is usually driven by a high power of several hundred W, so that even the low level components may not necessarily be quite ignorable for the ultrasound probe 102, and could affect the ultrasound tomographic image obtained at the ultrasound imaging device 105. Consequently, it is desirable to make the frequency ratio between them to be as large as possible.

In a practical ultrasound medical treatment apparatus, the ultrasound imaging device 105 has the central frequency of 3 to 5 MHz, while the ultrasound for treatment has the frequency of 1 to 2 MHz. Thus, the frequency ratio of the treatment frequency and the imaging frequency is only two to three times, and for such a not so large frequency ratio, there are cases in which the introduction of the noises into the ultrasound tomographic image becomes unignorable because of the high power of the ultrasound for treatment as described above.

In order to deal with this problem, since the noises are going to be introduced only during the ultrasound irradiation, it suffices to provide means for reducing the noises during this period alone on the ultrasound probe 102.

To this end, it is possible to make the ultrasound imaging device 105 to maintain the constant S/N ratio for the ultrasound tomographic image. Namely, the ultrasound imaging device 105 can be equipped with means for increasing the transmission power of the ultrasound imaging device 105 in accordance with the increase of the noises due to the ultrasound irradiation, only during the ultrasound irradiation time, so as to compensate the lowering of the S/N ratio due to the increased noise. Here, it should be obvious that the power of the ultrasound pulse for imaging should be limited within a range of not giving any adverse influence to the normal living body tissues.

Figure 40:
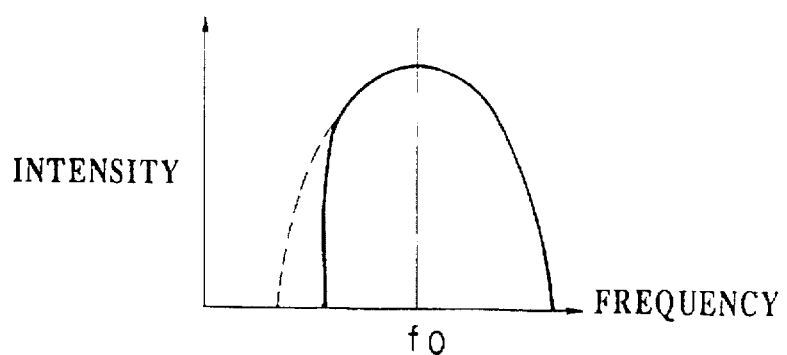
FIG. 40 is a graph showing a frequency characteristic of ultrasound pulse for imaging after the filter processing used in the apparatus of FIG. 37.

Alternatively, it is also possible to apply the high pass filter processing with the cutoff frequency set to be at a level of not significantly affecting the ultrasound tomographic image, to the received signals of the ultrasound probe 102 before the imaging of the received signals. For example, in a case the power of the ultrasound for treatment is so large that the frequency components lower than the frequency bandwidth of the ultrasound probe 102 are introduced as the noises to affect the ultrasound tomographic image, it is possible to remove the noises by applying the high pass filter processing with the cutoff frequency for cutting frequencies below the frequency bandwidth of the ultrasound probe 102. Also, the even when the noise components contains frequencies at the lower part of the frequency bandwidth of the ultrasound probe 102, the cutoff below the frequency at about 70% of the central frequency f0 of the ultrasound probe 102 as shown in FIG. 40 has only small influence to the ultrasound tomographic image, so that the monitoring by the ultrasound tomographic image is still possible.

When the influence of the filter processing on the ultrasound tomographic image is small, the filter processing may be incorporated in the ultrasound imaging device 105 permanently, but when the influence of the filter processing on the ultrasound tomographic image is large, the filter processing can be applied only during the ultrasound irradiation by the ultrasound transducer 101.

Here, as the filter processing, it is possible to use a digital filter in which the FFT (Fast Fourier Transform) is applied to the received signals containing the noises of the ultrasound probe 102, and the digital processing to set the signals to zero for the noise frequency range is applied to the transformed signals, and then the inverse FFT is applied to the noise removed signals. By using such a digital filter, the noises can be removed more sharply compared with a case of using the analog filter, and it is even possible to interpolate the removed image signal components.

Figure 41A:
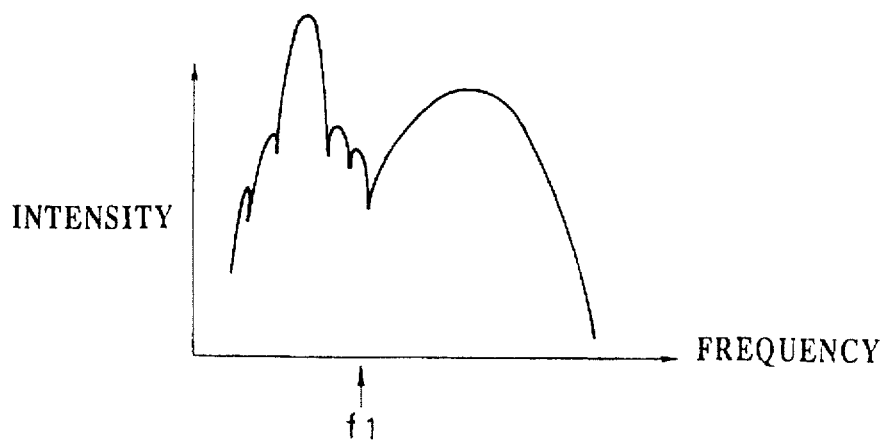
FIGS. 41A, 41B, and 41C are graphs showing frequency characteristics of received, filtered, and interpolated signals in the apparatus of FIG. 37.
Figure 41B:
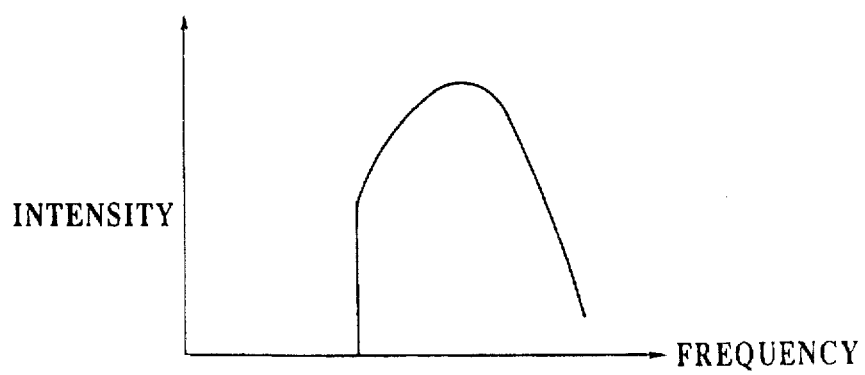
Figure 41C:
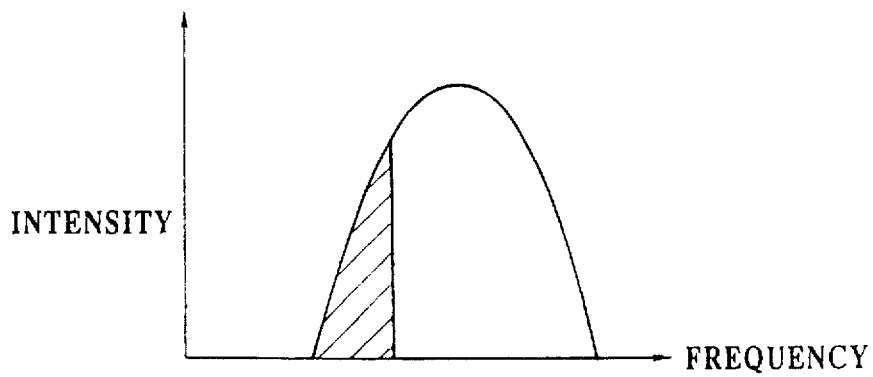

Namely, in a case the frequency components of the transformed image signals containing the noises appear as shown in FIG. 41A, the frequencies below f1 can be cut off by the digital processing as shown in FIG. 41B. The noise removed image signals can be obtained by further applying the inverse FFT. In a case the image signal components that had been cut off together with the noise components are large, the cut off components (shaded region in FIG. 41C) can be interpolated as shown in FIG. 41C by using an appropriate function, to reduce the disturbance of the image signals. When such a digital filter is provided in the ultrasound imaging device 105 permanently, there is no need to control the ultrasound imaging device 105 in synchronization to the ultrasound transducer 102, so that there is no need to provide means for controlling the synchronization between them, and consequently the system configuration can be simplified.

It is also possible to record the pure noise components in advance, and subtract the recorded noise components from the received signals containing the noises, to obtain the noise removed image signals. This scheme is effective when the noise components cover a wide range of the frequency bandwidth of the ultrasound probe 102. This scheme can be realized by providing means for instantaneously recording only the ultrasound components received by the ultrasound probe 102 during the ultrasound irradiation, and removing the recorded noise components from the received signals only during the ultrasound irradiation, in the ultrasound imaging device 105.

Next, the tenth embodiment of an ultrasound medical treatment apparatus according to the present invention will be described in detail. Here, those elements which are equivalent to the corresponding elements in the ninth embodiment of FIG. 37 will be given the same reference numerals in the figure and their descriptions will be omitted.

Figure 42:
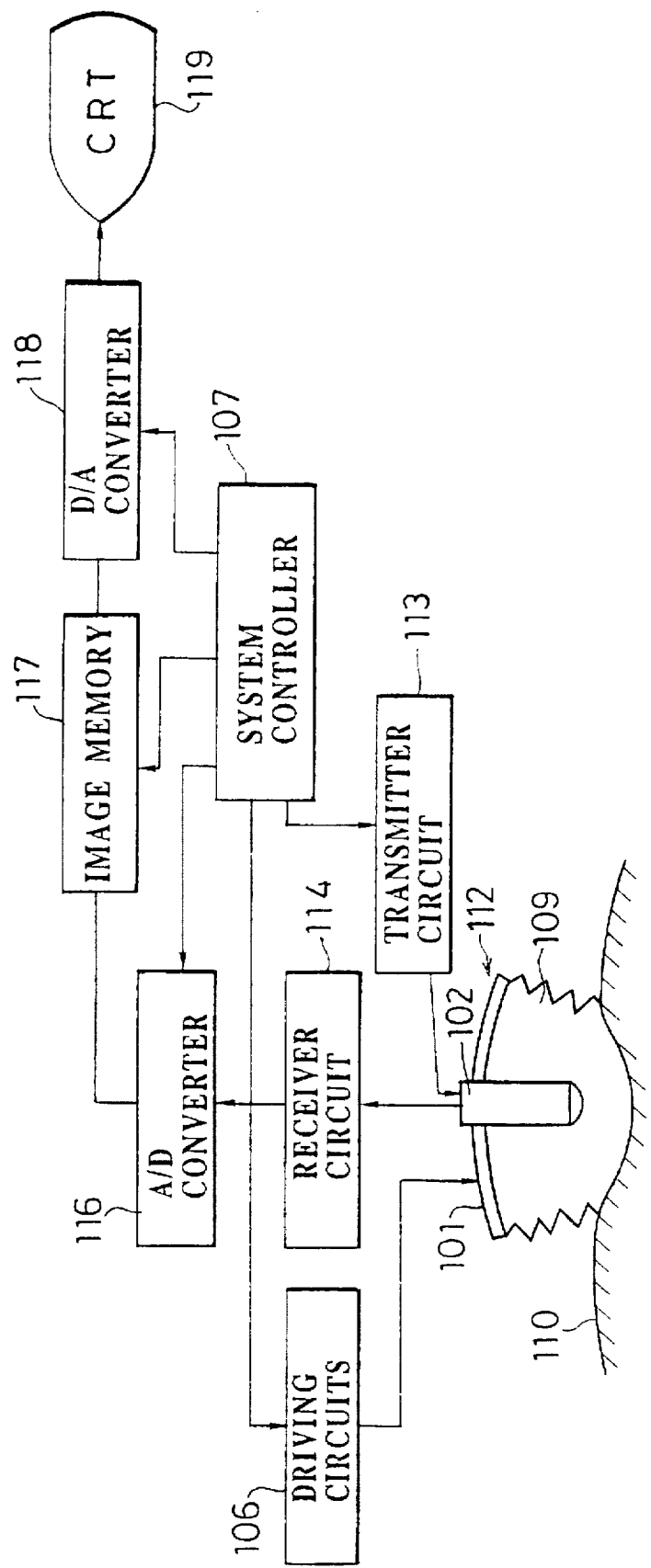
FIG. 42 is a schematic block diagram of a tenth embodiment of an ultrasound medical treatment apparatus according to the present invention.

In this tenth embodiment, as shown in FIG. 42, the ultrasound probe 102 is connected with a transmitter circuit 113 controlled by the system controller 107 for setting an appropriate transmission frequency for the ultrasound pulses to be transmitted, and a receiver circuit 114 for amplifying and detecting the reflected signals received by the ultrasound probe 102. The output of the receiver circuit 114 is then A/D converted by an A/D converter 116 at timings controlled by the system controller 107 to obtain digital image signals, and stored in an image memory 117. The image signals stored in the image memory 117 can be read out with an appropriate data processing for display purpose applied under the control of the system controller 107, and D/A converted by a D/A converter 118 at timings controlled by the system controller 107, and then displayed on the CRT 119.

Now, in this tenth embodiment, one or both of the ultrasound transducer 101 and the ultrasound probe 102 are made to be capable of exciting the secondary harmonic in addition to a fundamental resonance due to the longitudinal oscillation, by being formed from a piezoelectric member in a laminated structure, which is preferably a double lamination structure.

More specifically, the piezoelectric member in a double lamination structure can be constructed in either one of the following two methods.

First, as shown in FIG. 43, on one side of a piezoelectric body 122 having electrodes 121 and 123 on both side, a plate member 125 having a nearly equal acoustic impedance is attached through an adhesive 120, where the driving voltage is applied to the piezoelectric body 122 through the electrodes 121 and 123. Here, the plate member 125 is preferably the same piezoelectric body in the same thickness as the piezoelectric body 122. Also, as shown in FIG. 44, instead of using the adhesive 120, the piezoelectric bodies 127 and 129 and the electrodes 126 and 128 can be formed integrally by the calcination. Here, the influence of the mismatching of the acoustic impedances at a junction section should be lowered as much as possible.

Secondly, two layers of different thicknesses are laminated together such that the relationships between the electric field direction and the polarization direction are opposite in two layers.

Namely, as shown in FIG. 45, two piezoelectric bodies 131 and 133 of different thicknesses are laminated together such that they are connected in series both acoustically and electrically, while they have opposite polarization directions 135, so that the relationships between the electric field direction and the polarization direction are opposite for these piezoelectric bodies 131 and 133. Here, in order to connect them in series electrically, the piezoelectric body 131 is sandwiched between the electrodes 130 and 132 while the piezoelectric body 133 are sandwiched between the electrodes 132 and 134, and the driving voltage is applied between the electrodes 130 and 134, as shown in FIG. 45.

Alternatively, as shown in FIG. 46, two piezoelectric bodies 137 and 139 of different thicknesses are laminated together such that they are connected in series acoustically and in parallel electrically, while they have the same polarization direction 140, so that the relationships between the electric field direction and the polarization direction are opposite in these piezoelectric bodies 137 and 139. Here, in order to connect them in parallel electrically, outer sides of the piezoelectric bodies 137 and 139 are covered by a common electrode 136 connected on side, while inner sides of the piezoelectric bodies 137 and 139 are separated by an inner electrode 138 connected with the electrode 136 on side, and the driving voltage is applied between the electrodes 136 and 138, as shown in FIG. 46.

Here, the principle of secondary harmonic generation will be described for a case of a configuration shown in FIG. 45. This principle equally applies to the other cases so that the other cases will not be described here.

In the configuration of FIG. 45, when the driving voltage is applied between the electrodes 130 and 134, the wave of condensation and rarefaction is propagated through the piezoelectric bodies 131 and 133. Now, when the wave of rarefaction is emitted to outside from the boundary surface XA of the piezoelectric body 131, the wave of condensation (1) is propagated within the piezoelectric body 131 by reaction. Meanwhile, at the boundary surface XB of the piezoelectric bodies 131 and 133, as the relationships between the electric field direction and the polarization direction are opposite in these piezoelectric bodies 131 and 133, when one of them is extended, the other one of them is contracted, so that the wave of condensation and rarefaction can be generated. Thus, the wave of condensation (2) propagates through the piezoelectric body 131 while the wave of rarefaction (3) propagates through the piezoelectric body 132. On the other hand, at the boundary surface XC of the piezoelectric body 133, the relationship of the electric field direction and the polarization direction is opposite of that of the piezoelectric body 131, so that the wave of rarefaction (4) is propagated within the piezoelectric body 133. Therefore, from the boundary surface XA, the waves (1) to (4) are emitted until they are dissipated. Here, when the wave arrives to the boundary surface XC, due to the relationship of the acoustic impedance with respect to outside, the polarity is inverted. Then, considering the fact that these two piezoelectric bodies have different thicknesses, the time interval between the wave of rarefaction and the wave of condensation is not constant. This means that the emitted wave can be expressed by the Fourier series with the fundamental frequency of the half wavelength equal to one half of the thickness of the entire laminated structure, and this implies that the higher harmonics of the even number degrees are present. Thus, it becomes possible to obtain the secondary harmonic in addition to the fundamental harmonic.

In this tenth embodiment, at least one of the ultrasound transducer 101 and the ultrasound probe 102 can generate the secondary harmonic in addition to the fundamental resonance, so that the combination of the treatment frequency and the imagine frequency for which the amount of noises is smallest can be selected from the available frequencies. Here, there are four different combinations available at most, in contrast to the conventional case in which there is only one choice.

In addition, the frequency can be selected according to the depth of the treatment region from the body surface, so that the safe treatment can be carried out more efficiently. More specifically, considering the dissipation of the ultrasound in the living body, the lower frequency should be selected for the deeper region, and the higher frequency should be selected for the shallower region. Here, the frequency is determined from the thickness of the entire double lamination structure, and by changing the ratio of thicknesses of two layers, the relative value of the electro-mechanical conversion efficiency for the fundamental resonance and the secondary harmonic can be controlled.

Figure 50:
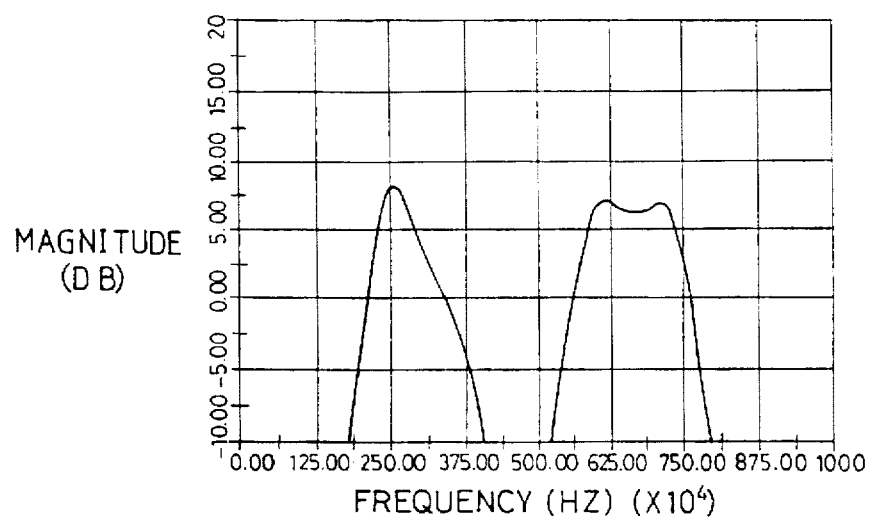
FIG. 50 is a graph showing an exemplary frequency characteristic of ultrasound pulse for imaging in the apparatus of FIG. 42.

Also, as the fundamental resonance and the secondary harmonic can be generated for the ultrasound pulses for imaging as shown in FIG. 50 for example, the transfer function (frequency spectrum of the impulse response) has a abrupt gap between the fundamental resonance and the secondary harmonic. Therefore, by setting the frequency in this gap as the frequency of the ultrasound for treatment, the introduction of noises into the ultrasound tomographic image due to the ultrasound irradiation can be reduced effectively.

Now, an exemplary actual construction of this tenth embodiment will be described. In this case, the treatment frequencies was set to be 1 MHz and 2 MHz, while the imaging frequencies was set to be 2.5 MHz and 5 MHz. Both of the ultrasound transducer 101 and the ultrasound probe 102 were formed by using the piezoelectric bodies made of the piezoelectric ceramic of lead zircon titanic acid (PZT) type, where the piezoelectric bodies for the ultrasound transducer 101 were formed in the configuration of FIG. 43, while the piezoelectric bodies for the ultrasound probe 102 were formed in the configuration of FIG. 45. The ultrasound transducer 101 was formed in a shape of a spherical shell with 15 cm diameter and 15 cm curvature of radius, while the ultrasound probe 102 was formed by an electronic sector probe mounted at a center of the ultrasound transducer 101. The double lamination structure for the ultrasound transducer 101 was formed by adhering the PZT piezoelectric ceramic through the epoxy adhesive over the convex side of the PZT piezoelectric ceramic of 1 mm thickness having the electrode on the concave side. On the other hand, the piezoelectric ceramic for the ultrasound probe 102 was formed by screen printing the platinum paste as an inner electrode over a green sheet, and then laminating another green sheet over it. After the removal of grease, they were integrally calcinated, and after the calcination, the thicknesses of the piezoelectric bodies were adjusted to be 400 µm and 200 µm. Then, the silver paste was printed over it, and the outer electrode was formed by the plating. After that, the polarization treatment was applied to make the polarization directions opposite. In constructing the ultrasound probe 102, the matching layer and the packing member were formed to set the thicker 400 µm piezoelectric body side to the ultrasound irradiation surface.

In this case, considering the dissipation of the ultrasound in the living body, the treatment frequency of 1 MHz and the imaging frequency of 2.5 MHz should preferably selected for regions deeper than 10 cm, while the treatment frequency of 2 MHz and the imaging frequency of 5 MHz should preferably selected for regions shallower than 10 cm, although these selections are not absolutely required. Also, the positioning of the focal point of the ultrasound for treatment to the treatment target can be made by mechanically moving the applicator 112. At this point, the adjustment in the depth direction can be made by adjusting the amount of the coupling fluid in the water bag to maintain the contact with the body surface of the patient.

It is to be noted that the mounting position of the ultrasound probe 102 is not necessarily limited to the center of the ultrasound transducer 101, and can be displaced to the edge side of the ultrasound transducer 101 as shown in FIG. 47.

Figure 48:
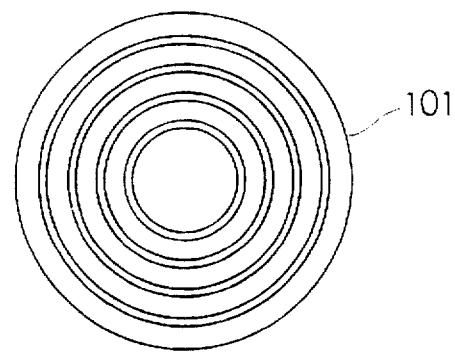
FIGS. 48 and 49 are plan views of transducers that can be used in the apparatus of FIG. 42.
Figure 49:
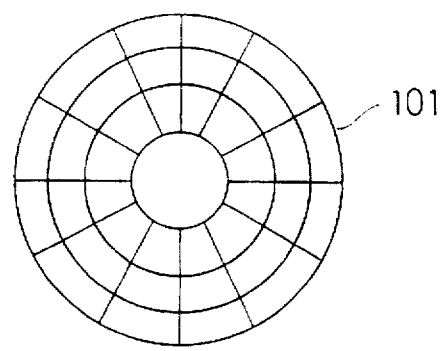

It is also possible to employ the ultrasound transducer 101 of a coaxial type as shown in FIG. 48, or a 2D array type as shown in FIG. 49, in which the focal point position can be changed electronically by controlling the driving phases of the transducer elements.

In addition, it is also possible to use the higher frequencies for the ultrasound for treatment instead of using them for the ultrasound pulses for imaging as described above.

Also, in this case, as shown in FIG. 50, the frequency of the ultrasound for treatment can be set to 3.75 MHz which is between the frequencies 2.5 MHz and 5 MHz for the imaging, so as to reduce the introduction of the noises into the ultrasound tomographic image.

Next, the eleventh embodiment of an ultrasound medical treatment apparatus according to the present invention will be described in detail.

The ultrasound applicator generally contains the ultrasound transducer for generating ultrasound for treatment as well as the ultrasound probe for obtaining the ultrasound tomographic image in a watertight state.

Figure 51:
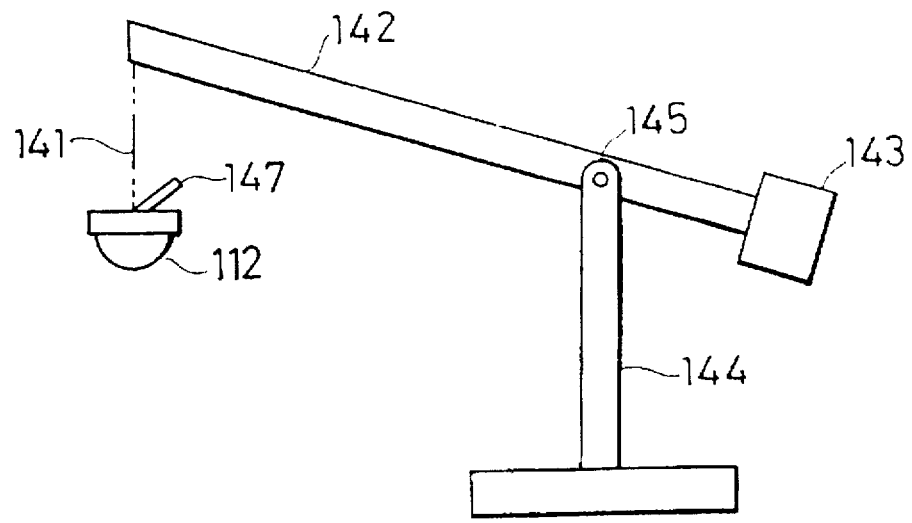
FIG. 51 is a schematic side view of an applicator part of an eleventh embodiment of an ultrasound medical treatment apparatus according to the present invention.

In this eleventh embodiment, as shown in FIG. 51, such an applicator 112 is suspended by two cables 141 and supported by an arm 142. The arm 142 is attached to a stand 144 to be swayable as well as rotatable, and an end of the arm 142 opposite to the applicator 112 has a counter balance 143 of nearly equal but slightly heavier weight than the applicator 112. Here, the joint portion 145 connecting the arm 142 and the stand 144 is not just made to be swayable and rotatable, but also made to provide an ample resistance, so that in a state in which the weights of the parts are nearly balanced, the arm 142 can be moved only when the external force is exerted, and when the external force is removed, the arm 142 maintains the applicator 112 at a slightly raised position as shown in FIG. 51.

Also, a base of the stand 144 is made to be movable in the horizontal direction. For this reason, when the operator holding a handle portion 147 projecting from the applicator 112 tries to move the applicator 112, the operator can position the applicator 112 at any desired position by merely overcoming the inertial force of the applicator 112, the resistive force exerted at the joint portion 145, and the resistive force exerted at the horizontal motion of the stand 144, and after moving the applicator 112, its position can be maintained with a very little force. Also, as the counter balance 143 is made to be slightly heavier than the applicator 112, the applicator 112 tends to move back from the patient unless the operator intentionally attached it to the patient, so that it can provide the fail safe operation environment.

Figure 52A:
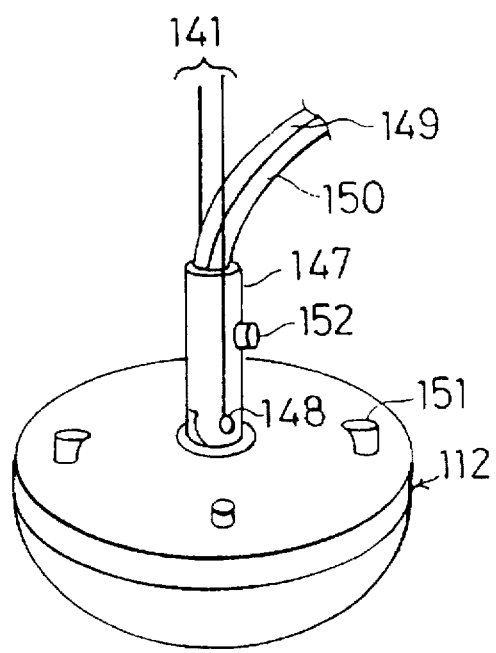
FIGS. 52A and 52B are detailed perspective views of the applicator part of FIG. 51.
Figure 52B:
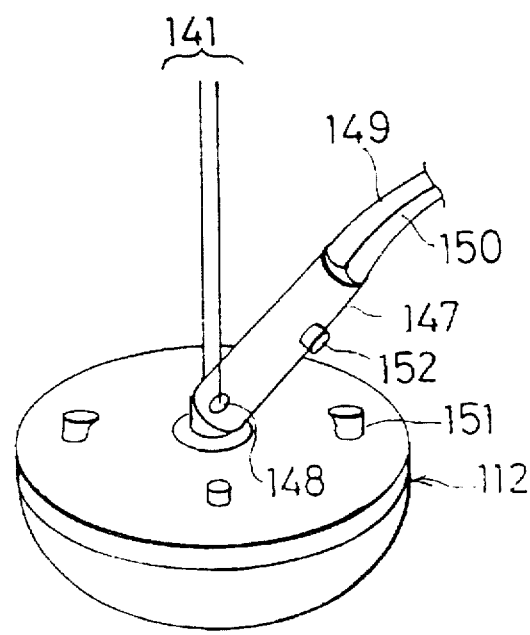

In further detail, the applicator 112 in this eleventh embodiment has a configuration as shown in FIGS. 52A and 52B, where FIG. 52A shows a state in which the handle portion 147 is vertically erected with respect to the applicator 112. This handle portion 147 is pivotable around a shaft 148, at two ends of which the cables 141 are fixedly attached.

Through the interior of this handle portion 147, a cable 149 for supplying electric power for driving the ultrasound transducer, and a hose 150 for supplying or draining the coupling water from the water bag are provided. The applicator 112 also has four hooks 51 for attaching a coupling member to be described below. In addition, the handle portion 147 has a switch 152 for controlling the ultrasound irradiation for treatment.

On the other hand, FIG. 52B shows a state in which the handle portion 147 is inclined with respect to the applicator 112. The joint portion of this handle portion 147 has such a structure that its inclined position at every predetermined angle is lightly held, to be easily movable further. This structure is well known so that its detail will be omitted here.

Figure 53A:
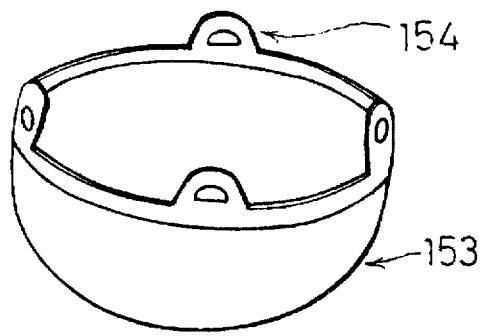
FIGS. 53A, 53B, and 53C are perspective view and cross sectional views in free and attached states, respectively, of the applicator part of FIG. 51.

In this eleventh embodiment, there is also provided a semi-spherical coupling member 153 shown in FIG. 53A, which has four resilient attachment portions 154 with attachment holes to be engaged with the hooks 151 provided on the applicator 112, at its upper open rim.

Figure 53B:
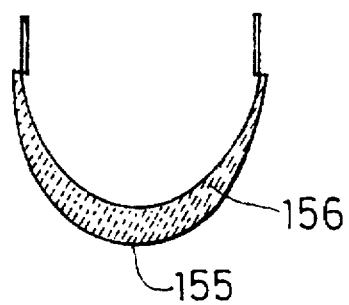
Figure 53C:
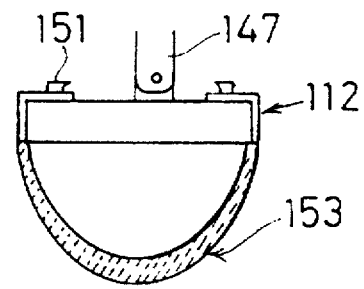

As show in FIG. 53B, the coupling member 153 itself is made of a double layered film member 155 which is made of a thin film capable of transmitting the ultrasound for treatment sufficiently, and within this double layered film member 155, a degassed sterile water 156 is contained. This coupling member 153 can be attached to the applicator 112 in a state show in FIG. 53C. Here, the film on the applicator 112 and the inner side of the coupling member 153 makes the contact portion through which the air cannot enter because of the air removed (not necessarily sterile) water or the ultrasound jelly poured into the cavity formed by the coupling member 153 at a time of attaching the coupling member 153 to the applicator 112.

The attachment portions 154 are hooked to the hooks 151 by being pulled by the operator to be in extended states in which the holes can be hooked to the hooks 151. As a consequence, it is extremely easy to replace this coupling member 153 by a new one.

Recently, the infection through the body fluids and bloods is increasing, so that the coupling member of the applicator 112 is usually disposed after every treatment, and this coupling member 153 is suitable for such a use as it is easily disposable just like the disposable operation gloves.

Figure 54:
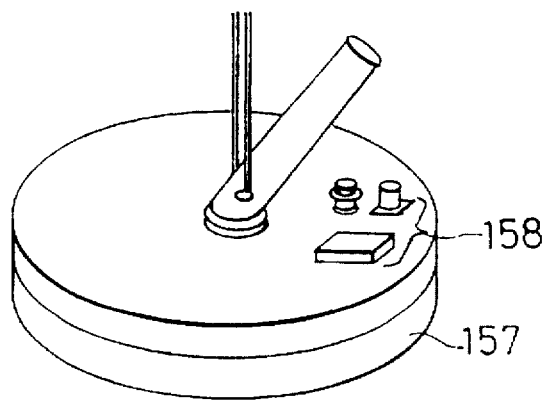
FIG. 54 is a detailed perspective views of the applicator part of FIG. 51.

The applicator 112 of this eleventh embodiment can be modified as shown in FIG. 54 in which the applicator body 157 has connectors 158 for connecting a cable for supplying the driving power for the ultrasound transducer, a hose for supplying and draining the water from the water bag, and a cable for transmitting data between the ultrasound probe and the external ultrasound imaging device, which are collectively arranged on an upper side of the applicator body 157 such that the cables and hose can be detached together easily at a time of sterilizing or exchanging the applicator.

It is to be noted that the applicator 112 of this eleventh embodiment may also be modified such that the counter balance mechanism can be replaced by the other balance mechanism such as that using the multi-joint arm type using springs for balancing, or electrical type using sensors and motors in combination.

Thus, according to this eleventh embodiment, the weight of the applicator can be nearly cancelled out by the counter balance, so that the operator can control the position of the applicator manually, without relying on a mechanical force. At this point, by holding the handle portion projecting from the applicator, the operator can control the applicator position more accurately.

With such a configuration, the applicator of this eleventh embodiment can be handled as if it is an ultrasound probe, so that the treatment target can be imaged at the same image quality as in the confirmation of the treatment target done by using the ultrasound probe before the treatment, and the ultrasound focal point can be placed on the treatment target accurately.

Also, because of the counter balance, the weight of the applicator itself is not going to be exerted entirely onto the patient, so that the uncomfortableness of the patient can be reduced.

Moreover, as the handle portion can be inclined at different angles, so that even in a case of treating the tumor on the upper liver, it becomes possible to attach the applicator to the treatment target by inclining the handle can be largely from the irradiation axis, and inserting the applicator into the narrow opened intestinal cavity from below the rib.

Also as the handle portion is rotatable, the tomographic plane angle of the ultrasound probe in the applicator can be changed without changing the angle of the handle portion.

Also, the power supply and water supply/drain cables and hose can be detachably attached to the applicator, so that in a case of sterilizing the exterior of the applicator, there is no need to sterilize the long cables and hose as well, and the sterilizing operation can be made simpler.

Also, as the coupling member is formed to be detachable from the applicator, the exchange of the coupling member for each patient can be done easily, and it becomes unnecessary to sterilizing the applicator which is difficult to sterilize after each treatment.

Also the coupling member has the sterile water contained therein, so that even if the small hole is created on the outer film of the coupling member during the ultrasound irradiation, there is no danger for the infection to the patient.

Consequently, there is need to sterilize the coupling fluid within the applicator, also, the bloods or body fluids of the patient are not going to reach to the applicator, so that there is no need to sterilize the applicator.

Next, the twelfth embodiment of an ultrasound medical treatment apparatus according to the present invention will be described in detail. Here, those elements which are equivalent to the corresponding elements in the ninth embodiment of FIG. 37 will be given the same reference numerals in the figure and their descriptions will be omitted.

Figure 55:
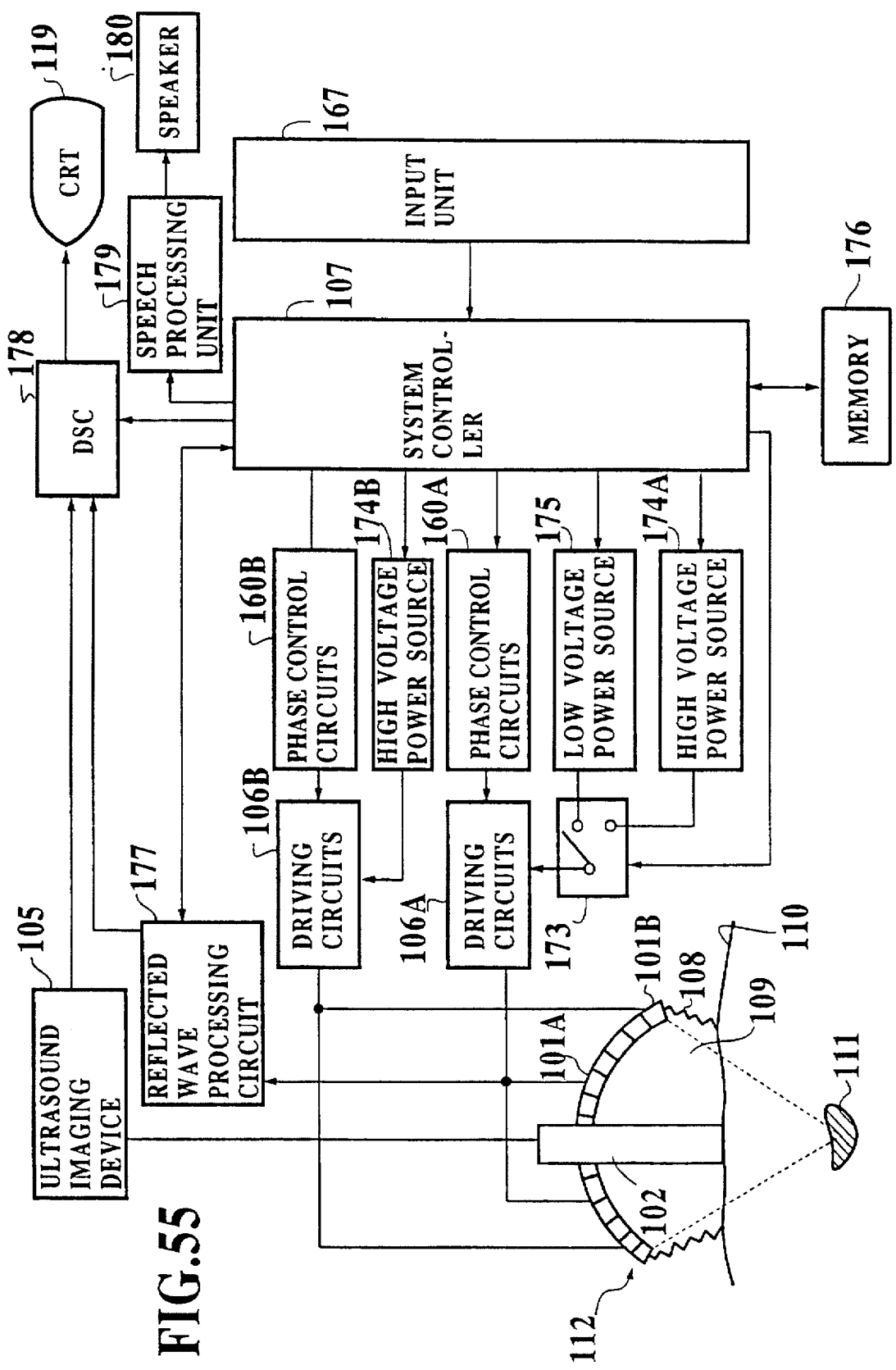
FIG. 55 is a schematic block diagram of a twelfth embodiment of an ultrasound medical treatment apparatus according to the present invention.

In this twelfth embodiment, the apparatus has a configuration as shown in FIG. 55, in which the ultrasound transducer comprises a number of piezoelectric elements 101A arranged near a center of a spherical shell and a number of piezoelectric elements 101B arranged around an edge of the spherical shell, which are driven independently by a driving circuits 106A and a driving circuits 106B, respectively, where each piezoelectric element 101A is driven at the resonant frequency of 250 KHz and used for the lithotriptic treatment, while each piezoelectric element 101B is driven at the resonant frequency of 1.5 MHz and used for the heating treatment. Here, the piezoelectric elements 101B for the heating treatment are arranged on outer side of the piezoelectric elements 101A for the lithotriptic treatment, in order to realize the smaller focal point size to which the intense ultrasound can be focused.

The driving circuits 106A is selectively connected with a high voltage power source 174A and a low voltage power source 175 through a switch 173. Here, the high voltage power source 174A is a power source for the heating treatment by the intense ultrasound irradiation, while a low voltage power source 175 is a power source for generating weak ultrasound pulses for scanning the treatment target 111. On the other hand, the driving circuits 106B is connected with a high voltage power source 174B similar to the high voltage power source 174A.

In addition, the driving circuits 106A is connected with a phase control circuits 160A, while the driving circuits 106B is connected with a phase control circuits 160B, and the switch 173, the high voltage power source 174A, the low voltage power source 175, the phase control circuits 160A, the high voltage power source 174B, and the phase control circuits 160B are all controlled by the system controller 107.

Moreover, the apparatus further includes a reflected wave processing circuit 177 connected with the piezoelectric elements 101A, and a digital scan converter (DSC) 178 connected with the reflected wave processing circuit 177, the ultrasound imagine device 105, and the CRT 119. The apparatus also includes a speech processing unit 179 and a speaker 180 for outputting audio messages for mode selection confirmation and warning, an input unit 167 including keyboard, mouse, light pen, etc., and a memory 176 for storing data.

Here, as disclosed in Japanese Patent Application Laid Open No. 63-5736 (1988), the piezoelectric elements 101A generates the weak ultrasound pulses toward the treatment target 111, and when the treatment target is a high reflector of the ultrasound such as a calculus, the scanning wave will be reflected at high efficiency only when the focal point coincides with the treatment target 111, so that the reflected wave can be received by the piezoelectric elements 101A, the obtained reflection signals can be processed by the reflected wave processing unit 177, and the obtained result can be transmitted to the system controller 107 as well as the DSC 178. The DSC 178 processes the reflected signals supplied from the piezoelectric elements 101A and the ultrasound image data supplied from the ultrasound imaging device 105, and displays the obtained result on the CRT 119.

Next, the operation of the apparatus of this twelfth embodiment will be described in detail.

First, a case of treating the treatment target 111 which is a kidney calculus or a biliary calculus will be described.

Figure 56:
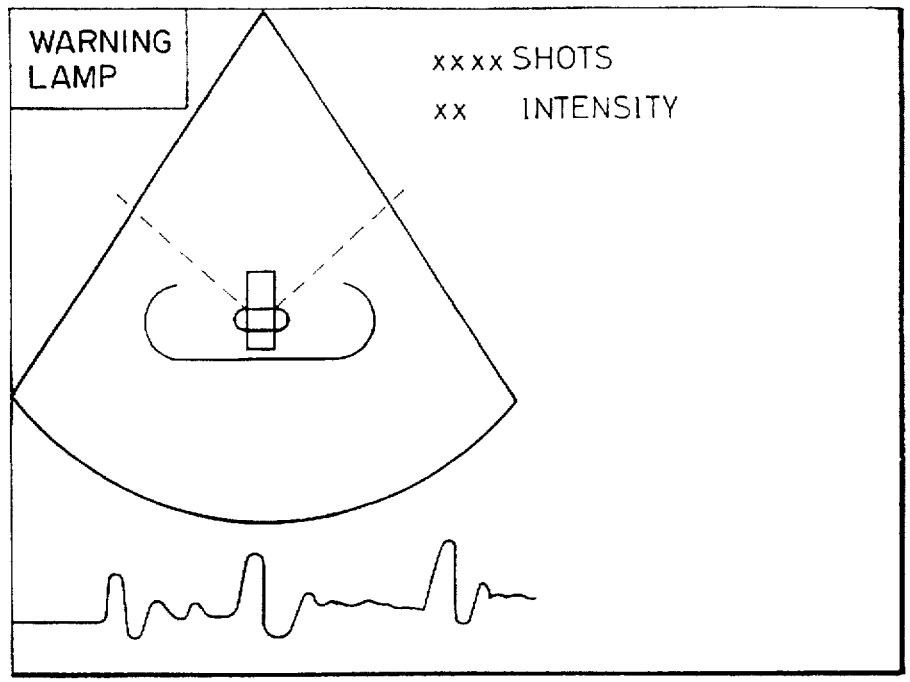
FIGS. 56 and 57 are illustrations of exemplary displays used in the apparatus of FIG. 55.

In this case, the operator selects the desired treatment mode by utilizing the input unit 167 according to the screen display as shown in FIG. 56. The selected treatment mode is transmitted to the system controller 107 and then displayed on the screen display through the DSC 178, while the audio message for the mode selection confirmation is outputted from the speaker 180 through the speech processing unit 179.

Next, the operator enters the irradiation mode and the irradiation energy, to complete the treatment preparation. In this lithotriptic treatment mode, the piezoelectric elements 101 A alone are usually operated, but the piezoelectric elements 101B may also be operated in a case the focal point pressure is to be increased.

When the intense ultrasound is irradiated from the piezoelectric elements 101A and 101B toward the focal point, the shock waves are formed near the focal point, and their peak pressure and focal point size can be changed by changing the rate of the ultrasound from the piezoelectric elements 101A and 101B. The operator enters the desired focal point peak pressure and the focal point size by using the input unit 167, and in response the system controller controls the outputs and output timings of the high voltage power sources 174A and 174B, according to the data stored in the memory 176.

Next, a case of heating treatment by the ultrasound irradiation will be described.

Figure 57:
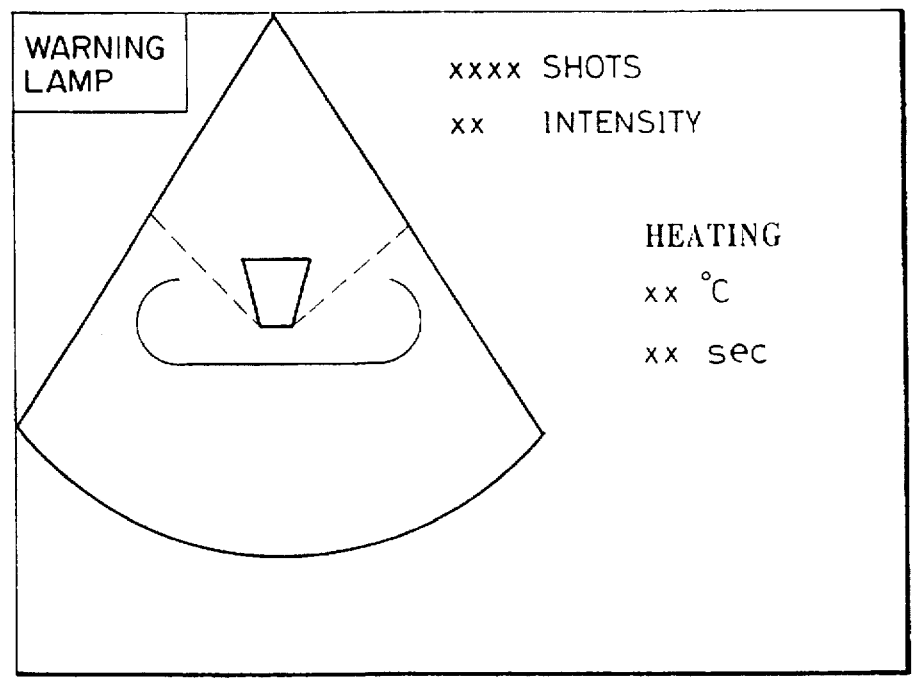

In this case, the operator selects the desired treatment mode by utilizing the input unit 167. Then, the selected treatment mode is transmitted to the system controller 107 and then displayed on the screen display as shown in FIG. 57 through the DSC 178, while the audio message for the mode selection confirmation is outputted from the speaker 180 through the speech processing unit 179.

Next, the operator enters the irradiation energy, burst length, and the repetition frequency, to complete the treatment preparation. In this heating treatment mode, the piezoelectric elements 101B are primarily used, but the piezoelectric elements 101A may also be used in order to set up the desired focal point pressure and focal point size, just as in a case of the lithotriptic treatment described above. Also, the burst length can be changed by controlling the time gate width of the phase control circuits 160A and 160B.

Now, when the piezoelectric elements 101B alone are used for the generation of the ultrasound for treatment, the piezoelectric elements 101A can be utilized for the ultrasound source for scanning.

Here, the frequency of the ultrasound for the heating treatment is usually about several MHz (1.5 MHz in this example), which is fairly close to the frequency (3.75 MHz) of the ultrasound for imaging by the ultrasound probe 102. Therefore, it is difficult to monitor the treatment in real time by using the ultrasound tomographic image obtained by the ultrasound probe 102 and the ultrasound imaging device 105 as the ultrasound tomographic image are likely to be affected by the noises due to the ultrasound irradiation for treatment. For this reason, the ultrasound for scanning at the frequency of 250 KHz can be used to monitor the treatment.

For example, as the heating treatment progresses and the degeneration of the tissues near the focal point is generated, the acoustic impedance at that portion can be changed largely. Therefore, the by irradiating the ultrasound for scanning toward the focal point during the heating treatment, by analyzing the size of the resulting reflected wave, it becomes possible to detect the change of the acoustic impedance due to the thermal degeneration of the tissues in real time, and this information can be utilized in controlling the irradiation of the ultrasound for treatment.

It is also possible to utilize the ultrasound for scanning to obtain information concerning the cavitations caused near the focal point. Namely, it is known that the cavitations can be caused in the water when the intense ultrasound is propagated through the water. The cavitations are filed with lower pressure gases, so that the ultrasound can be absorbed, scattered, or reflected by the cavitations. When the intense ultrasound is focused onto the focal point, the cavitations can be caused in front of the focal point and the focal point.

For this reason, the ultrasound energy is affected by the cavitations in front of the focal point, and the portion in front of the focal point can also cause the thermal degeneration. In order to avoid this, the ultrasound pulses for the scanning from the piezoelectric elements 101A can be utilized to detect the generation of the cavitations in front of the focal point as the receiving interval for the reflected waves from the cavitations becomes shorter, such that the heating treatment can be stopped.

It is also possible to obtain information concerning the change in the body surface. Namely, in the heating treatment, the temperature increase at the body surface can cause the problem. In a case of irradiating the intense ultrasound toward the living body, the temperature of the body surface increases when the transmission energy density at the body surface is large, and it could even cause the thermal degeneration in some cases.

In order to avoid this, the ultrasound for scanning generated from the piezoelectric elements 101A can be utilized as follows. First, the distance between the ultrasound transducer and the body surface and the reflection intensity of the scanning ultrasound at the body surface are measured in advance. Then, as the body surface starts to change because of the heating, the change on the body surface can be detected as the reflection intensity of the scanning ultrasound become larger.

More specifically, by adjusting the receiving gate time for the reflected wave processing circuit 177 such that the signals from the body surface can be received, it becomes possible to selectively obtain the reflected waves from the body surface, so that as the size of the reflected wave becomes larger than a certain threshold, the ultrasound irradiation is stopped, and the warning is outputted.

It is to be noted that the operations using the piezoelectric elements 101A can also be achieved by the ultrasound for imaging from the ultrasound probe, such that the warning can be issued or the ultrasound irradiation is stopped when the echo at the body surface becomes large.

Figure 58:
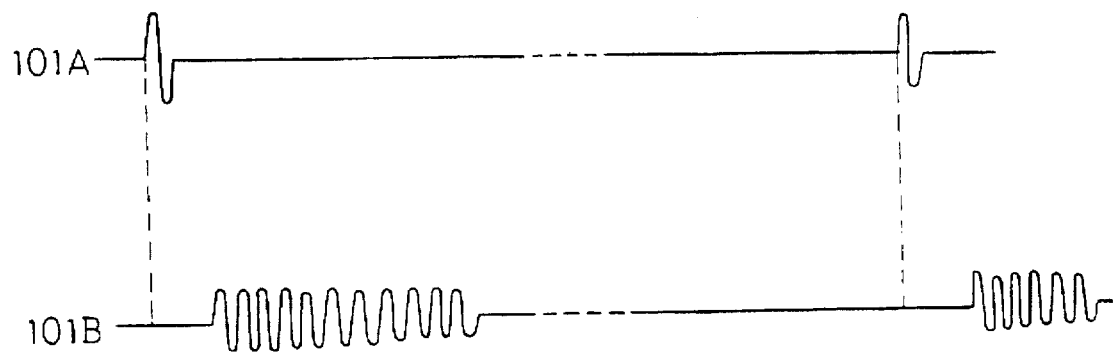
FIG. 58 is a timing chart for explaining one operation in the apparatus of FIG. 55.

It is also possible to consider the active utilization of the cavitations as follows. Namely, the piezoelectric elements 101A and 101B are connected to the high voltage power sources 174A and 174B, respectively. Then, as shown in FIG. 58, the shock waves are focused to the focal point by applying the high voltage pulses to the piezoelectric elements 101A. Then, after an appropriate delay, the piezoelectric elements 101B are operated such that the intense ultrasound from the piezoelectric elements 101B reach to the focal point when the cavitations are generated in a vicinity of the focal point by the shock waves due to the piezoelectric elements 101A.

At this point, as reported in K. Hynynen, Ultra. Med. Biol., 17, (1991), pp. 157–169, the energy of the ultrasound for treatment is absorbed by the cavitations, and that region can be heated higher than a case without the cavitations, so that the treatment efficiency can be improved.

Next, the thirteenth embodiment of an ultrasound medical treatment apparatus according to the present invention will be described in detail. Here, those elements which are equivalent to the corresponding elements in the ninth and twelfth embodiments of FIGS. 37 and 55 will be given the same reference numerals in the figure and their descriptions will be omitted.

Figure 59:
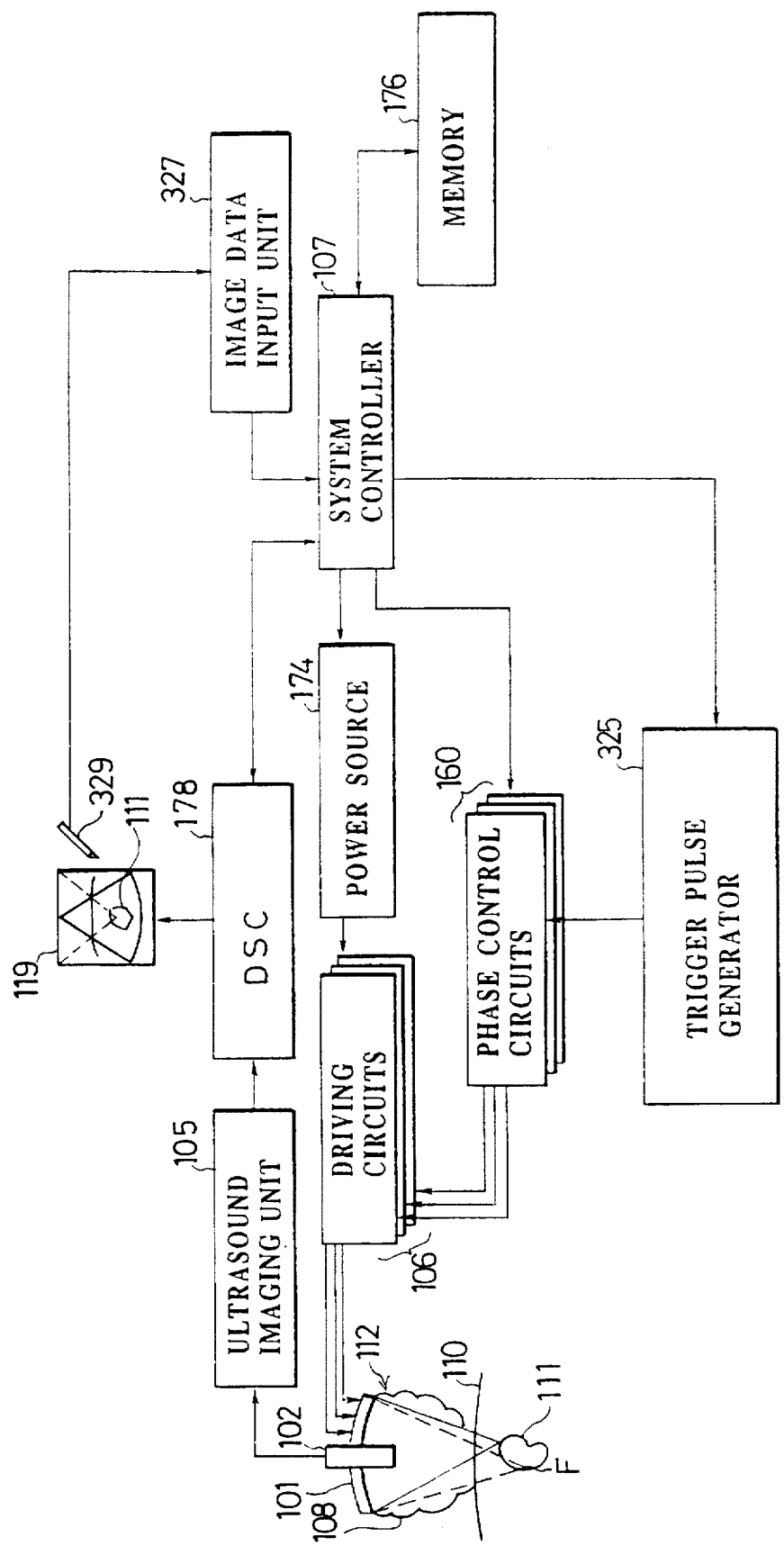
FIG. 59 is a schematic block diagram of a thirteenth embodiment of an ultrasound medical treatment apparatus according to the present invention.
Figure 61:
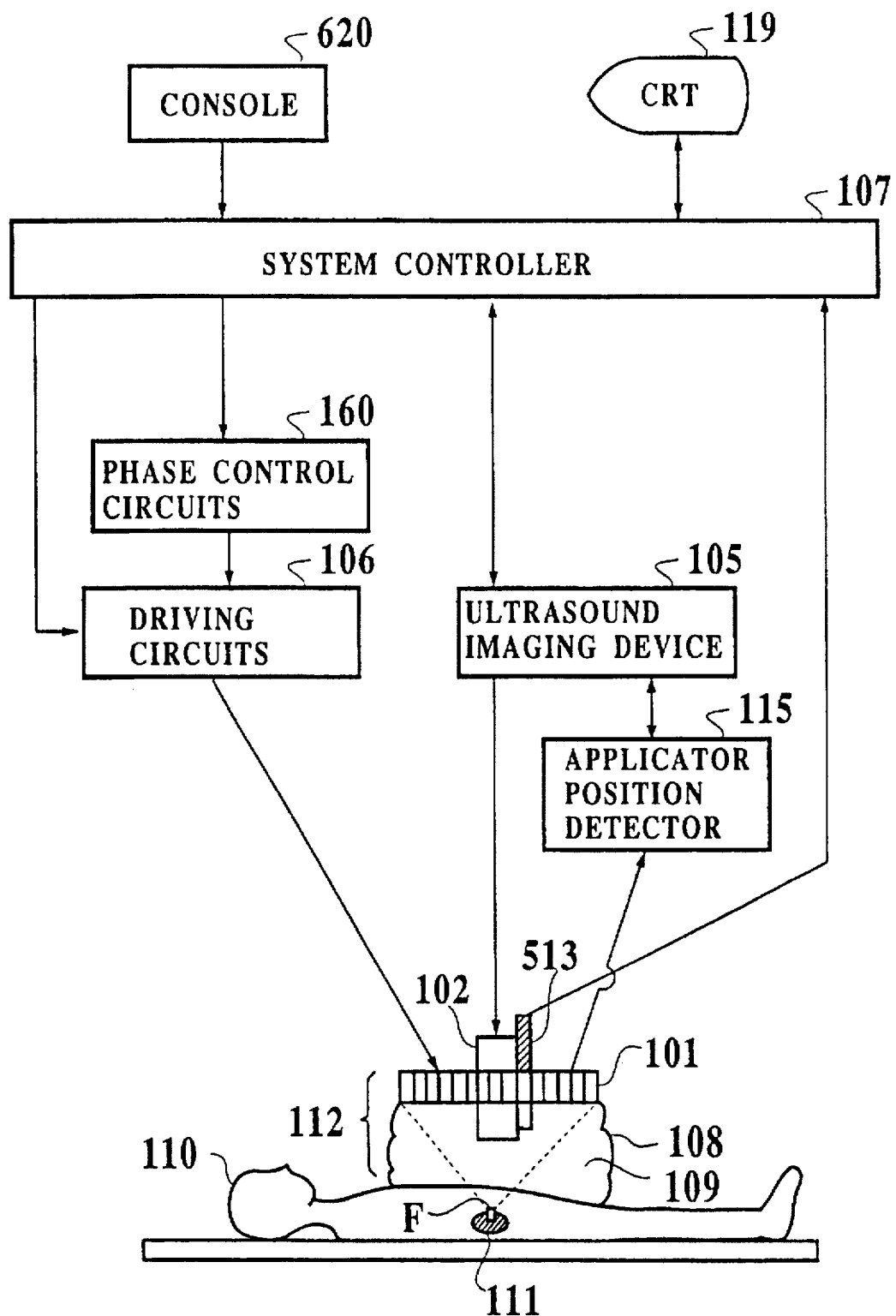
FIG. 61 is a schematic block diagram of a fourteenth embodiment of an ultrasound medical treatment apparatus according to the present invention.

In this thirteenth embodiment, as shown in FIG. 59, a power source 174 and a phase control circuits 160 for controlling the driving circuits 106 are provided between the driving circuits 106 and the system controller 107, and a trigger pulse generator 325 is provided between the phase control circuits 160 and the system controller 107. In addition, an image data input unit 327 for allowing an input on the image data displayed on the CRT 119 by using a light pen 329 is incorporated.

In this thirteenth embodiment, the focal point ultrasound intensity is controlled as follows.

The ultrasound propagating through a medium has the lowering pressure and intensity due to the dissipation by the medium. In general, it is known that the dissipation is proportional to the frequency of the ultrasound and the propagation distance of the ultrasound within the medium.

In the water, the dissipation is nearly ignorable, but the dissipation in the living body is unignorable, so that the dissipation becomes larger for the treatment target 111 located deeper from the body surface, and for the ultrasound of the higher frequency generated by the piezoelectric elements, and consequently the intensity of the ultrasound becomes lower.

In addition, in a case of changing the focal point position by controlling the driving phase timings of the piezoelectric elements, if the driving voltage is to be maintained constant, the intensity of the ultrasound will be changed depending on the position of the focal point.

Figure 60A:
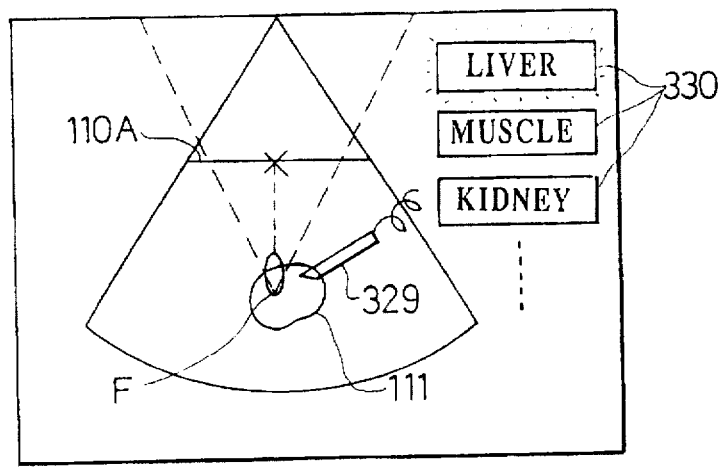
FIGS. 60A and 60B are illustrations of exemplary display and memory content, respectively, used in the apparatus of FIG. 59.

In view of these, in this thirteenth embodiment, the the body surface 110A and the treatment target 111 are marked by the light pen 329 on the screen display of the CRT 119 as shown in FIG. 60A, and the distance between them is calculated by the system controller 107 according to the corresponding dot numbers on the memory 176. Also, at a time of controlling the focal position through the phase control circuits 160, the dissipation due to the propagation distance is calculated by the system controller 107, according to the delay value specified for each piezoelectric element by the system controller 107. The dissipation factors vary for different treatment portion, so that the appropriate values for each treatment portion are stored in advance in the memory 176 as a table. The selection from the stored table is made by displaying the treatment portion selection switches 330 on the screen display as shown in FIG. 60A and selecting an appropriate switch by the light pen 329.

Then, according to these calculated values and the driving frequency, the focal point intensity curve with respect to the input powers of the power source 174 is calculated by the system controller 107 and the calculated value is stored in the memory 176. Then, according to this curve, the system controller 107 controls the driving power from the power source 174 such that the focal point ultrasound intensity can be maintained at the setting value.

Here, instead of controlling the driving power to maintain the focal pint ultrasound intensity to be constant, it is also possible to calculate the temperature increase curve as a function of time at the focal point with respect to the ultrasound intensity, frequency, dissipation, and thermal conductivity, such that the temperature increase can be controlled by controlling the driving time. In this case, however, for the temperature increase, it is also possible to use the calculated values stored in advance in the memory 176 instead.

Also, in the experiments, there has been the observation of the phenomenon in which the heat generation region is spreading and the thermally degenerated portion is enlarging in front of the focal point during the long time irradiation.

Thus, by storing the maximum irradiation allowable time (safe irradiation time, i.e., the irradiation time by which the focal point region alone can be thermally degenerated at a certain ultrasound intensity) with respect to the focal point intensity, and controlling the driving time of the trigger pulse generator 325 from the control circuit 107 according to the stored value, the safe treatment can be secured.

In addition, as for the driving power, there may be cases in which the temperature increase of 50° C. within a reference time for example cannot be obtained, so that in such a case, the the maximum temperature increase obtainable within a prescribed time can be displayed on the CRT 119, and the warning for the insufficient focal point intensity is outputted, or the trigger pulse generator is disabled by the system controller 107 to stop the ultrasound irradiation.

Figure 60B:
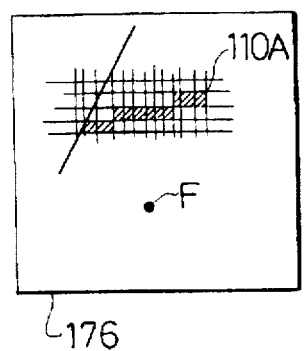

It is also possible to extract the high echo portion of the body surface on the image memory as shown in FIG. 60B, and the depth to the focal point can be calculated automatically, instead of obtaining the depth according to the body surface and the treatment portion specified by the light pen, since the signal intensity is different within the water in the water bag and within the living body.

Next, the fourteenth embodiment of an ultrasound medical treatment apparatus according to the present invention will be described in detail. Here, those elements which are equivalent to the corresponding elements in the previous embodiments will be given the same reference numerals in the figure and their description will be omitted.

In this fourteenth embodiment, the apparatus includes a pressure sensor 513 located at a center of the ultrasound transducer 101 along the ultrasound probe 102, which measures the inner pressure of the coupling fluid 109 within the water bag 108. The apparatus also includes the applicator position detector 115 for detecting the position of the applicator 112 and the console 620 for entering inputs.

During the treatment, when the patient 110 abruptly moves by sensing an intense pain or heat, or for some other reason, the focal point F of the intense ultrasound can be displaced from the prescribed position, and there is a danger for the erroneous irradiation onto the normal tissues. For this reason, in a case the sudden pressure change is caused in the coupling fluid 109 within the water bag 108 by the movement of the patient 110, the pressure sensor 513 senses this, and notifies the system controller 107. In response, the system controller 107 directly controls the driving circuits 106 to stop the ultrasound irradiation immediately.

Also, in a case of the highly intensive ultrasound irradiation, there are cases in which the patient senses the pain. In such a case, the pressure change of the coupling fluid 109 due to the reflective motion of the patient 110 caused by the pain is detected by the pressure sensor 513 and notified to the system controller 107. In response, the system controller 107 controls the driving circuits 106 to lower the irradiation intensity by one or more steps for the next irradiation.

As the patient 110 gets used to the intense ultrasound irradiation, the patient 110 stops sensing the pain even for the highly intensive irradiation. For this reason, the system controller 107 controls the driving circuits 106 to make the low intensity irradiations for a prescribed number of times, and then increase the irradiation intensity one step or more steps. Here, i a case the reflective motion of the patient 110 is sensed by the pressure sensor 513 again, the irradiation intensity is lowered by one step. These settings can be entered from the console 620 by the operator.

Instead of sensing the patient's movement by measuring the pressure change of the coupling fluid 109, it is also possible for the system controller 107 to sense the patient's movement according to the large change in the image displayed on the CRT 119 during the treatment.

In this case, before the treatment, the ultrasound tomographic image is displayed on the CRT 119 in real time, and the system controller 107 memorizes the position of the treatment portion and the periodic motion (such as the respiration motion) as the basic form from the displayed ultrasound tomographic image. Then, during the treatment, when the ultrasound tomographic image has changed from the memorized state in excess of the prescribed tolerable range due to the abrupt movement of the patient 110, the system controller 107 controls the driving circuits 106 to stop the irradiation as in the above. Also, from the displacement between the basic form obtained from ultrasound tomographic image and the real time image, the reflective motion of the patient 110 caused by the pain can be sensed, and the irradiation intensity can be controlled as described above.

It is also possible to sense the shock caused to the patient 110 by the pain or heat from the electroencephalogram, or the electrocardiogram, or the internal current, and stops the ultrasound irradiation or control the irradiation intensity as in the above.

Also, in order to avoid the possibility for the operator to fail to notice the pain or heat sensed by the patient 110 or the danger caused by the apparatus malfunction, it is also possible to provide the patient 110 means for calling up the operator or for causing the emergency stop of the treatment.

It is to be noted that this fourteenth embodiment is equally applicable to the heating treatment of the tumor described above, as well as the lithotriptic treatment of the calculus within the body.

Next, the fifteenth embodiment of an ultrasound medical treatment apparatus according to the present invention will be described in detail. Here, those elements which are equivalent to the corresponding elements in the previous embodiments will be given the same reference numerals in the figure and their descriptions will be omitted.

In this fifteenth embodiment, the apparatus includes a target size measurement unit 612 for monitoring the progress of the lithotriptic treatment for the calculus as disclosed in Japanese Patent Application No. 3-199695 (1991), which measures the size of the calculus before the treatment as well as the size and spread of the calculus fragments during and after the treatment, and outputs the measurement result to the system controller 107.

In response, the system controller 107 determines the output of the power source 174 and the delay values of the phase control circuits 176 according to the data from the target size measurement unit 612, the input from the console 620, and the stored data in the memory 176, and changes the size of the focal point mark displayed on the ultrasound imaging device 105. These controls can be made in real time during the treatment. The memory 176 stores the data on the focal point pressure, the focal point size, and the focal point energy value for various settings of the driving energy and the driving timing of the piezoelectric elements.

The apparatus also includes an ultrasound power switching unit 616 connected with the power source 174 and the system controller 107 for switching the ultrasound power setting.

Next, the operation of this fifteenth embodiment will be described in detail for an exemplary case of the lithotriptic treatment.

Here, the calculus 111 within the patient110 is to be treated by irradiating the intense ultrasound for treatment. The normal procedure for such a treatment is that, until the patient 110 gets used to and stops sensing the pain, the lower energy ultrasound is irradiated, and then gradually the energy of the ultrasound is increased.

In increasing the ultrasound intensity, the if the driving power of the ultrasound transducer is increased linearly, the peak pressure at the focal point increases to an unnecessarily high level, such that the irradiated energy would not be effectively directed to the treatment of the calculus.

Namely, in FIGS. 63A and 63B, a dashed line indicates the necessary pressure threshold for crushing, indicating that the crushing occurs at the pressure level above this line. FIG. 63A shows a case in which the input energy is insufficient so that the effective pressure region is a region a1 alone. When the driving power is increased from there, the focal point pressure distribution increases its level while keeping an approximately similar overall shape, and as shown in FIG. 63B, the effective pressure region becomes a region b1. Normally, the size of the calculus is in a range of few mm to ten and few mm, but the region b1 has 2 to 3 mm, so that the crushing does not takes place very effectively, despite of the high focal point pressure.

Here, however, it is known that the amount of crushing also depends on the energy, so that the crushing can be achieved efficiently with respect to the input energy by increasing the focal point energy by elongating the waveform timewise as in a region c1 in FIG. 63B or by enlarging the focal point size while maintaining the pressure above the threshold. In this fifteenth embodiment, this control is carried out by the system controller 107 automatically.

Namely, every time the driving energy of the ultrasound irradiation is set up, the output of the power source 174 and the delay values of the phase circuits 160are controlled to adjust the focal point energy and the focal point peak pressure, according to the data from the target size measurement unit 612 and the ultrasound imaging device 105, and the stored data in the memory 176, while paying attention to that the focal point size should not exceed the size of the calculus itself. At this point, the size of the focal point mark displayed on the ultrasound imaging device 105 is also changed in correspondence to the actual focal point size. Here, instead of using the data stored in the memory 176, the calculation by the system controller 107 or the input data from the console 620 may be used.

As for the method for controlling the focal point pressure and size, it is possible to adopt the scheme such as that disclosed in Japanese Patent Application No. 4-253553, in which the zero-cross frequency of the waveform is lowered by lowering the spherical surface precision electronically.

By utilizing this fifteenth embodiment, even when the ultrasound output is set to be high immediately after the start of the treatment for example, it is possible to construct the system in which the ultrasound energy immediately after the irradiation is kept low, and as the numbers of irradiations increases, the ultrasound energy is also increased, and the driving timings of the piezoelectric elements are controlled such that the focal point size is automatically enlarged, while the focal point pressure is maintained constant.

Now, the fifteenth embodiment described above can be modified as follows. In this modified embodiment, the applicator 112 uses the phased array type ultrasound transducer. In this case, when the focal point position is shifted from the geometrical center electronically, it is known that the peak pressure and the focal point size are going to be changed as well.

In particular, in a case of shifting the focal point from the geometrical center toward the applicator side, the focal point pressure increases and there exist the focal point position at which the focal point size becomes smaller. In such a case, it is also possible that the pressure becomes so large that the influence can be given to the living body.

In this fifteenth embodiment, the data on the focal point pressure and the focal point size with respect to the input energy and the focal point position are stored in advance in the memory 176, and the system controller 107 outputs the driving energy data and the delay data appropriate for each focal point according to these data. The power source 174 and the phase control circuits 160 then outputs the appropriate driving energy and the delay pulses according to the signals from the system controller 107.

On the ultrasound tomographic image, the focal point mark at the position and the size corresponding to the actual focal point position and the actual focal point size are displayed. Here, the focal point position data, and the data the driving power and the delay values may be obtained by the calculation instead of reading from the memory 176. It is also possible to change these data from the console 620 whenever necessary.

Thus, the focal point energy and the focal point pressure can be controlled in real time during the treatment.

Also, in a case of detecting the coincidence or non-coincidence of the focal point and the treatment target by using the erroneous irradiation prevention mechanism as disclosed in Japanese Patent Application Laid Open No. 62-49843 (1987), by utilizing this fifteenth embodiment, the pressure or the size of the focal point position can be maintained constant, so that the stable reflected signals can be obtained, while the erroneous irradiation prevention mechanism can be used stably even in a case shifting the focal point.

It is to be noted here that, besides those already mentioned above, many modifications and variations of the above embodiments may be made without departing from the novel and advantageous features of the present invention. Accordingly, all such modifications and variations are intended to be included within the scope of the appended claims.

What is claimed is:

1. An ultrasound medical treatment apparatus, comprising:

an ultrasound applicator for applying ultrasound irradiation to a treatment target; and an ultrasound imaging device for imaging the treatment target by transmitting ultrasound pulses and receiving the ultrasound pulses reflected by the treatment target, said ultrasound imaging device increasing a transmission power of the ultrasound pulses during the ultrasound irradiation by the ultrasound applicator so as to reduce noise due to the ultrasound irradiation by the ultrasound applicator.

* * * * *